US006498019B1

(12) United States Patent
Taniyama

(10) Patent No.: US 6,498,019 B1
(45) Date of Patent: Dec. 24, 2002

(54) LECITHIN-CHOLESTEROL ACYLTRANSFERASE PROTEIN

(75) Inventor: Yoshio Taniyama, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/402,532

(22) PCT Filed: Apr. 9, 1998

(86) PCT No.: PCT/JP98/01643

§ 371 (c)(1),
(2), (4) Date: Oct. 4, 1999

(87) PCT Pub. No.: WO98/46767

PCT Pub. Date: Oct. 22, 1998

(30) Foreign Application Priority Data

Apr. 11, 1997 (JP) .............................................. 9-093355
Jul. 10, 1997 (JP) .............................................. 9-184885
Jan. 22, 1998 (JP) ........................................... 10-010289

(51) Int. Cl.$^7$ ........................... C12P 12/06; C12P 1/60; C12P 1/00; G01H 31/00; C07K 14/00
(52) U.S. Cl. ..................... 435/69.1; 435/4; 435/11; 436/13; 530/300; 530/350
(58) Field of Search ................... 424/94.1, 139.1; 435/4, 11, 69.1, 70.1; 436/13; 530/300, 350

(56) References Cited

U.S. PATENT DOCUMENTS 4,007,091 A * 2/1977 Nagasaki et al. .............. 195/99
4,163,011 A * 7/1979 Orts ........................ 260/112.5

FOREIGN PATENT DOCUMENTS

| EP | 0 222 591 A | | 5/1987 |
| EP | 0 222 591 | * | 5/1987 |
| WO | WO 96 20004 A | | 7/1996 |
| WO | WO 96 28553 A | | 9/1996 |
| WO | WO-97/17434 A | * | 5/1997 |

OTHER PUBLICATIONS

Marra et al. 1996. EMBL Database Accession No. W65635.*
Varma et al. 1977. Characterization of antibody to human phosphatidylcholine: cholesterol transferase. Biochemica et Biophysica Acta. vol. 486 (2); 378–84. Abstract only.*

Rader et al. Curr. Artheroscler. Rep. 1999; 1 (1): 58–69.*

F. Tata et al., "The isolation and characterisation of cDNA . . . " *Biochimica et Biophisica Acta* 910 (1987) p. 142–148.

D. Chawla and J. Owen, "Secretion of active human lecithin–cholesterol . . . " *Biochem. J.* (1995) 309, p. 249–253.

Y. Harada et al., "Lecithin: cholesterol acyltransferase" *Japanese J. of Clinical Medicine* 52, 12, (Dec. 1, 1994) p. 92–97 (English translation is also submitted).

M. Marra et al., "The WashU–HHMI–Mouse EST Project, AC W65635" *EMBL Database*, Jun. 12, 1996, XP002073272.

B. Vaisman et al, "Overexpression of Human Lecithin Cholesterol . . . " *J. of Biological Chemistry*, vol. 270, No. 20, May 19, 1995, pp. 12269–275.

Y. Taniyama et al., "Cloning and Expression of a Novel Lysophospholipase . . . " *Biochemical and Biophysical Research Communications* 257, 50–56 (Apr. 2, 1999).

* cited by examiner

*Primary Examiner*—James Housel
*Assistant Examiner*—Shannon A. Foley
(74) *Attorney, Agent, or Firm*—Mark Chao; Elaine M. Ramesh

(57) ABSTRACT

This invention relates to a novel protein having a lecithin-cholesterol acyltransferase-like activity, etc. or its salt, a precursor protein of the protein or its salt, a partial peptide of the protein or its salt; a DNA coding for the protein; a recombinant vector; a transformant; a method for producing the protein, a pharmaceutical composition comprising the protein, the partial peptide or its salt; and an antibody to the protein or the partial peptide. The protein, the partial peptide or its salt, and the DNA are useful as an agent for treating or preventing arteriosclerosis, atherosclerosis, hyperlipidemia, hypercalorism, obesity or hypertriglyceridemia. The antibody can be used in assay of the protein, the partial peptide or its salt. The protein, the partial peptide or its salt is useful as a reagent for the screening for candidate medical compounds.

12 Claims, 18 Drawing Sheets

Figure 1

```
                                                  gcatcccgga cctgcggcga ccgtcgtaca cc atg ggc ctc cac ctc cgc ccc tac cgt gtg ggg ctc gat ggc  80
                                                                                     Met Gly Leu His Leu Arg Pro Tyr Arg Val Gly Leu Pro Asp Gly ctc ctg ttc ctc ttg ctg cta atg ctg ctc gcg gac ctc ccg gcc gga cgt cac ccc gtg gtg ctg gtc 161
Leu Leu Phe Leu Leu Leu Met Leu Leu Ala Asp Leu Leu Pro Ala Gly Arg His Pro Val Val Leu Val cct ggt gat ttg ggt aac caa ctg gaa gcc aag ctg gac aca gtg gtg cac tac ctc tgc aag aag acc gaa 242
Pro Gly Asp Leu Gly Asn Gln Leu Glu Ala Lys Leu Asp Thr Val Val His Tyr Leu Cys Ser Lys Thr Glu agc tac ttc aca atc tgg ctg aac ctg gaa ctg ctg cct gtc att gac tgc tgg att gac aat atc agg ctg gtt 323
Ser Tyr Phe Thr Ile Trp Leu Asn Leu Glu Leu Leu Pro Val Ile Asp Cys Trp Ile Asp Asn Ile Arg Leu Val tac aac aaa aca tcc agg gcc acc cag ttt cct gat ggt gta cgt gat gta ttc cac acc ttc tca ctg 404
Tyr Asn Lys Thr Ser Arg Ala Thr Gln Phe Pro Asp Gly Val Arg Asp Val Phe His Thr Phe Ser Leu gag ttc ctg gac ccc agc aaa agc agc ctg ggt gtg gag agc ctt gtg ggc tgg ggc tac aca 485
Glu Phe Leu Asp Pro Ser Lys Ser Ser Val Gly Val Glu Ser Leu Val Gly Trp Gly Tyr Thr cgg ggt gag gat gtc cga ggt gct ccc tat ccc cga aat gaa gcc cca aac ggg ccc ttc ctg gcc ctc cgc 566
Arg Gly Glu Asp Val Arg Gly Ala Pro Tyr Pro Arg Arg Asn Glu Ala Pro Asn Gly Pro Phe Leu Ala Arg gag atg atc gag gag atg tac cag ctg tat ggg ggc gtt gcc cac agt atg ggc aac atg tac acg ctc 647
Glu Met Ile Glu Glu Met Tyr Gln Leu Tyr Gly Gly Val Ala His Ser Met Gly Asn Met Tyr Thr Leu tac ttt ctg cag cgg cag ccg cag gcc ttc atc gtg tca ctg gcg ccc tgg ggg ggc 728
Tyr Phe Leu Gln Arg Gln Pro Gln Ala Phe Ile Val Ser Leu Gly Ala Pro Trp Gly Gly gtg gcc aag acc gct gtc cgc gtc gct ctg gcc tgg atc cca gtc atc ggg ccc ctg aag atc gtg ttc gtg gag cag 809
Val Ala Lys Thr Ala Val Arg Val Ala Leu Ala Trp Ile Pro Val Ile Gly Pro Leu Lys Ile Val Phe Val Glu Gln cag cgg tca gct gtc acc agc tgg gga gac gcc atg tgg tca cct gaa gat ggc tat ggc gtc ccc aca cca gac 890
Gln Arg Ser Ala Val Thr Ser Trp Gly Asp Ala Met Trp Ser Pro Glu Asp Gly Tyr Gly Val Pro Thr Pro Asp aca atc aac tac aca ctg cgg gac acg gac atc ttc cag cag ctg cac ctc ttt gtg ctc atg cgg cag gac 971
Thr Ile Asn Tyr Thr Leu Arg Asp Thr Asp Ile Phe Gln Gln Leu His Leu Phe Val Leu Met Arg Gln Asp aca gaa ggg ctg gtg gaa gcc acg gcc atg cca cct ggc gtg cag gtc ccc aca cca gac 1052
Thr Glu Gly Leu Val Glu Ala Thr Ala Met Pro Pro Gly Val Gln Val Pro Thr Pro Asp tcc ttc tac tat gag agc ttc cct gac cgt gac cct aaa atc tgc ttt ggt gac ggc gat ggt act gtg aac ttg aag agt 1133
Ser Phe Tyr Tyr Glu Ser Phe Pro Asp Arg Asp Pro Lys Ile Cys Phe Gly Asp Gly Asp Gly Thr Val Asn Leu Lys Ser gcc ctg cag tgc cag gcc tgg gcc caa gtg cac cag agc cga gag gag ctg cca ggc gag cac atc gag 1214
Ala Leu Gln Cys Gln Ala Trp Ala Gln Val His Gln Ser Arg Glu Glu Leu Pro Gly Ser Glu Ile Glu atg ctg gcc aac gcc acc ctg gcc tat ctg aaa cgt gtg ctc ctt ggg ccc tga                                   1271
Met Leu Ala Asn Ala Thr Leu Ala Tyr Leu Lys Arg Val Leu Leu Gly Pro *
```

Figure 2

```
atg ggc ctc cac ctc cgc ccc tac cgt gtg ggg ctg ccc gat ggc ctc ttc ctg ctg cta atg ctg ctc    81
Met Gly Leu His Leu Arg Pro Tyr Arg Val Gly Leu Pro Asp Gly Leu Phe Leu Leu Leu Met Leu Leu gcg gac cca gcg ctc ccg gcc cga cgt cac ccc cca gtg gtg ctg gtt ggt aac caa ctg gaa gcc aag   162
Ala Asp Pro Ala Leu Pro Ala Arg Arg His Pro Pro Val Val Leu Val Gly Asn Gln Leu Glu Ala Lys ctg gac aag ccg aca gtg gtg cac tac ctc tgc ctc aag aag acc gaa agc tac ttc aca atc tgg ctg aac ctg gaa ctg   243
Leu Asp Lys Pro Thr Val Val His Tyr Leu Cys Ser Lys Lys Thr Glu Ser Tyr Phe Thr Ile Trp Leu Asn Leu Glu Leu ctg ctg cct gtc atc att gac tgc tgg att gac atc agg ctg tgc agt gca atc tcg gct cac tac tct   324
Leu Leu Pro Val Ile Ile Asp Cys Trp Ile Asp Ile Arg Leu Cys Ser Gly Ala Ile Ser Ala His Tyr Ser gcc tcc cag gct caa gca ctt ctc gtg cct cag act ccg gat aac tgg gat tac agg ctg gtt aac aaa aca tcc agg   404
Ala Ser Gln Ala Gln Ala Leu Leu Val Pro Gln Thr Pro Asp Asn Trp Asp Tyr Arg Leu Val Tyr Asn Lys Thr Ser Arg gcc acc cag ttt cct gat gta cgt gtc gct gcc cct ggc ttt ggg phe gly lys aag acc ttc tca ctg gag ttc ctg gac ccc agc   485
Ala Thr Gln Phe Pro Asp Val Arg Val Ala Pro Gly Phe Gly Lys Thr Phe Ser Leu Glu Phe Leu Asp Pro Ser aaa agc gtg ggt tcc tat ttc cac acc atg gtg gag agc ctt ggc tgg ggc tac aca cgg ggt gag gat gtc cga   566
Lys Ser Val Gly Ser Tyr Phe His Thr Met Val Glu Ser Leu Gly Trp Gly Tyr Thr Arg Gly Glu Asp Val Arg ggg gct ccc tat gac tgg cgc cga gcc cga gcc aat gaa aac ggg ccc tac ttc ctg gcc ctc gag atc gag gag atg   647
Gly Ala Pro Tyr Asp Trp Arg Arg Ala Pro Ala Asn Glu Asn Gly Pro Tyr Phe Leu Ala Leu Arg Ile Glu Glu Met tac cag ctg tat ggg ggc ccc gtg gtg ctg gtt gcc cac agt atg ggc aac atg tac ctc tac ttt ctg cag cgg cag   728
Tyr Gln Leu Tyr Gly Gly Pro Val Val Leu Val Ala His Ser Met Gly Asn Met Tyr Thr Leu Tyr Phe Leu Gln Arg Gln ccg cag gcc aag gac gac aag tat atc cgg gcc gcc ttc gtg tca ctg ggt gcg ccc ccc tgg ggg ggc gtg gcc aag acc ctg cgc   809
Pro Gln Ala Lys Asp Asp Lys Tyr Ile Arg Ala Ala Phe Val Ser Leu Gly Ala Pro Trp Gly Gly Val Ala Lys Thr Leu Arg gtc gct gga gac gac aag aac atc gga gtc atc ggg aag cgg gag cag cag ccc aca atc aac tac gct gtc tcc   890
Val Leu Ala Ser Gly Asp Asp Lys Asn Asn Ile Gly Val Ile Gly Lys Leu Arg Gln Gln Pro Thr Ile Asn Tyr Ala Val Ser acc agc tgg ctg ccc cgt ctg cct tac aac tgg acg tca cct gag aag gtg ttc gtg cag aca aca ccc aca atc tac aca ctg   971
Thr Ser Trp Leu Pro Arg Leu Pro Tyr Asn Trp Thr Ser Pro Glu Lys Val Phe Val Gln Thr Pro Thr Ile Asn Tyr Thr Leu cgg gac tac aag cgc aag ttc tcc cag gtg ctg cag atc ggc atc ggc ttt gaa ggc atc cgg cag gac aca gaa aca ggg ctg gtg gaa  1052
Arg Asp Tyr Lys Arg Lys Phe Ser Gln Val Leu Gln Ile Gly Ile Gly Phe Glu Gly Ile Arg Gln Asp Thr Leu Met Arg Gly Leu Val Glu gcc acg atg cca cct ggc gtg gtg cag cct ggg cac cag gct ggc cgg gtc act gtg ccc aca cca gac tcc ttc tac tat gag agc   1133
Ala Thr Met Pro Pro Gly Val Val Gln Pro Gly His Gln Ala Gly Arg Val Thr Val Pro Thr Pro Asp Ser Phe Tyr Tyr Glu Ser ttc cct gac cgt gac cct aaa atc tgc ttt ggt gac gat ggt aag gcc atc gag aac ttg aag gcc cag tgc gcc  1214
Phe Pro Asp Arg Asp Pro Lys Ile Cys Phe Gly Asp Asp Gly Lys Ala Ile Glu Asn Leu Lys Ala Gln Cys Ala tgg cag agc cgc cag gag cag gag caa gtt gtg ctg ctg cag gag cag ctg cca ggc cga atc gag cac atc gag atg gcc aac gcc acc  1295
Trp Gln Ser Arg Gln Glu Gln Glu Gln Val Leu Leu Gln Glu Gln Leu Pro Gly Arg Ile Glu His Ile Glu Met Ala Asn Ala Thr acc ctg gcc tat ctg aaa cgt gtg ctc ctt ggg ccc tga                                             1335
Thr Leu Ala Tyr Leu Lys Arg Val Leu Leu Gly Pro *
```

Figure 3

```
atg gat cgc cat ctc tgc acc tgt cgc gag acc cag ctc cgg agt ggc ctc ctg cct ctg ttt cta atg atg ctg gca gac ctc        96
Met Asp Arg His Leu Cys Thr Cys Arg Glu Thr Gln Leu Arg Ser Gly Leu Leu Pro Leu Phe Leu Met Met Leu Ala Asp Leu ccg gcc caa cgt cac ccc ccg gtg gtg ctg gtg cct ggt gat ttg ggt gaa gca aag ctg gat aag cca aag gtt gta cac tac ctt    192
Pro Ala Gln Arg His Pro Pro Val Val Leu Val Pro Gly Asp Leu Gly Glu Ala Lys Leu Asp Lys Pro Lys Val His Tyr Leu tgc tcc aag aag acg gac agc tac ttc aca ctc tgg ctg aat ctg gaa ctt ctg cct gtt atc att gac aat atc agg ctg            288
Cys Ser Lys Lys Thr Asp Ser Tyr Phe Thr Leu Trp Leu Asn Leu Glu Leu Leu Pro Val Ile Ile Asp Asn Ile Arg Leu gtt tac aac aga aca tct cgg gcc acc cag ttt ccc gat ggt gtc gac gtg gtg cgt gtg gac ttt tct atg gaa ttc cta gac        384
Val Tyr Asn Arg Thr Ser Arg Ala Thr Gln Phe Pro Asp Gly Val Asp Val Val Arg Val Asp Phe Ser Met Glu Phe Leu Asp ccc agc agg aat gtg ggt tcc tat atg act atg gtg gag agc ctt gtg tgg ggc aca cgg ggt gaa gac gtt cga ggt gct ccc        480
Pro Ser Arg Asn Val Gly Ser Tyr Met Thr Met Val Glu Ser Leu Val Trp Gly Thr Arg Gly Glu Asp Val Arg Gly Ala Pro tat gat tgg cgg cga gcc aat gaa aac cca cgg gcc ttg tac ctg cga gag atg atc gag atg ctg tat ggg ggc ccc gtg            576
Tyr Asp Trp Arg Arg Ala Asn Glu Asn Pro Arg Ala Leu Tyr Leu Arg Glu Met Ile Glu Met Leu Tyr Gly Gly Pro Val gtg ctg gtc gcc cac agc atg ggc aac gtg tac atg ggt ctg cag cgg caa caa ttt aag gac tgg aaa tat atc cat gcc ttc gtc    672624
Val Leu Val Ala His Ser Met Gly Asn Val Tyr Met Gly Leu Gln Arg Gln Gln Phe Lys Asp Trp Lys Tyr Ile His Ala Phe Val tca ctg ggg gcg ccc tgg ccc cga gcg gtg gcc gtg ctg ctc acg aat aat cgc gtc att ccc att ggg cca ctg aag atc            768
Ser Leu Gly Ala Pro Trp Pro Arg Ala Val Ala Val Leu Leu Thr Asn Asn Arg Val Ile Pro Ile Gly Pro Leu Lys Ile cgg gaa cag cag cga tct gcc gtc gcc cgt gcc act acc agc tgg tca cat gaa aag gta ttt gta tac aca ccc acg act            864
Arg Glu Gln Gln Arg Ser Ala Val Ala Arg Ala Thr Thr Ser Trp Ser His Glu Lys Val Phe Val Tyr Thr Pro Thr Thr aac tac acg ctc cgg gac tat cac cgg ttc ttc gaa gat ggc atc ggt ttc ctg atg cgg gag aca ggg ctg gtt gaa gcc            960
Asn Tyr Thr Leu Arg Asp Tyr His Arg Phe Phe Glu Asp Gly Ile Gly Phe Leu Met Arg Glu Thr Gly Leu Val Glu Ala atg acg cca ccc ggg gtg gag cac ctg tgc cac ctg cat ggc act ggt tat ccc acg aac tct ttc gag agc ttt cct gat cgg gac    1056
Met Thr Pro Pro Gly Val Glu His Leu Cys His Leu His Gly Thr Pro Asn Ser Phe Tyr Glu Ser Phe Pro Asp Arg Asp aaa atc tgc ttc gat gca acg ggc gtg aac ctg gag agc acg cag tgc caa agc cgc caa gag cgc cag cgc aga gta tca ttg         1152
Lys Ile Cys Phe Asp Ala Thr Gly Val Asn Leu Glu Ser Thr Gln Cys Gln Ser Arg Gln Glu Arg Gln Arg Arg Val Ser Leu cag gag ctg ccg gga agc gag cac att gag cac gcc aat gag cta gcc acc ttg gct ctg aaa cgt gtg ctt ctg gaa cct tga        1239
Gln Glu Leu Pro Gly Ser Glu His Ile Glu His Ala Asn Glu Leu Ala Thr Leu Ala Thr Leu Ala Tyr Leu Lys Arg Val Leu Leu Glu Pro *
```

Figure 4

```
                     10            20            30            40
mCLP    M D R H L C T C R E T Q L L P L F L L L M L A D L T L P A Q R H P P V
hCLP    M G L H L R P Y R R V G L L P D G L L F L L M L L A D P A L P A G R H P P V 50            60            70            80
mCLP    V L V P P G D L G N Q L E A K L D K P K V V H Y L C S K K T D S Y F T L W L N L E
hCLP    V L V P P G D L G N Q L E A K L D K P T V V H H Y L C S K K T E S Y F T H W L N L E 90           100           110           120
mCLP    L L L P V H I D D C W I D N I H R L V Y N R T S R A T Q F P D D G V D V R R V P G F G E
hCLP    L L L P V H I D D C W I D N I H R L V Y N K T S R A T Q F P D D G V D V R R V P G F G K 130           140           150           160
mCLP    T F S M E F L D P S K R N V G S Y F Y T M V E S L V G W G Y T R G E D V R G A P
hCLP    T F S L E F L D P S K S S V G S Y F H T M V E S L V G W G Y T R G E D V R G A P 170           180           190           200
mCLP    Y D W R R A P N E N G P Y F L A L R E M I E E M Y Q M Y G G P V V L V A H S M G
hCLP    Y D W R R A P N E N G P Y F L A L R E M I E E M Y Q L Y G G P V V L V A H S M G 210           220           230           240
mCLP    N V Y M L Y F L Q R Q P Q Q R Q K Y I H R A A F V H A P W G G V A K T L R V L
hCLP    N M Y T L Y F L Q R Q P Q Q R Q K Y I H R L A F V H A P W G G V A K T L R V L 250           260           270           280
mCLP    A S G D N N R I P V I G P L K K I R E Q Q R S A V S T S W L L P Y N H T W S H E K
hCLP    A S G D N N R I P V I G P L K K I R E Q Q R S A V S T S W L L P Y N Y T W S P E K 290           300           310           320
mCLP    V F V Y T P T T H N Y T L R D Y H R F F R D I G F E D D G W F M R Q D T E G L V E A
hCLP    V F V Q T P T T I N Y T L R D Y R K F F Q D I G F E D D G W L M R Q D T E G L V E A 330           340           350           360
mCLP    M T P P G V E L H C L L Y G T G V P T P N S F Y Y E S F P D R D P K I C F G D G D
hCLP    T M P P G V Q L H C L L Y G T G V P T P D S F Y Y E S F P D R D P K I C F G D G D 370           380           390           400
mCLP    G T V N L E S V L Q C Q A W Q S R Q E H R V S L Q E L P G S E H I E M L A N A T
hCLP    G T V N L K S A L Q C Q A W Q S R Q E H Q V L L Q E L P G S E H I E M L A N A T 410
mCLP    T L A Y L K R V L L E P    *                                                    413
hCLP    T L A Y L K R V L L G P    *
```

Underlined Residues differ from the consensus

Figure 5

```
cgcgtcgcca ccgcccccgc ctaggcgaga gcccagagag ctgaacctgc atcccggacc tgcggcgacc gtcgtacacc atgggcctcc acctccgccc 100
ctaccgtgtg gggctgctcc cggatggcct cctgttcctc ttgctgctgc taatgctgct cgcggaccca gcgctcccgg ccggacgtca cccccagtg 200
gtgctggtcc ctggtgattt gggtaaccaa ctggaagcca gccgacagtg gtgcactacc tctgctccaa gaagaccgaa agctacttca 300
caatctggct gaacctggaa ctgctgctgc ctgta ---> 335
```

Figure 6

```
ACTATAGGGCACGCGTGGTCGACGGGCCCGGGCTGGTATTAAAAAAAAATCAGGGCCGGGTGTGATGGCTCATACCTGTAATCCCAGCACTTTGGGAGA 100
▬▬▬▬▬▬▬▬ Adaptor ▬▬▬▬▬▬▬
CCTAGGTGGGTGGATCACCTGAGGTCAGGAGTTCAAGACCAGCCTGGCCAACATGGCGAAATCCCGTCTCTACTAAAAATACAAAAATCAGCTGGGCGT 200
                    [LXR/RXR]       [AP-2]          [NF-IL6]           [TFIID]    [Sp1]
GGTGGCGGGTGCCTGTAATCCCAGCTATTCAGGAGGCTGAGGCAGGAGAATCGCTTGAACCCAGGAGGCAGAGGTTGCAGTGAGCCGGGATCACGCCACT 300
                                                                                      [SRE]
GCTCTCCAGCCTGGGTGACAGAGCAAAACTCTGTCTCAAAAAAAAAGGTGTCAGCCTGGCATGTGGGAGAACGACCCACAGGAACGAGGGCGTGCA 400
[S]           [NF-S]
TTGGGACATCAGTGACGAGGCTGTTGTGGGAATAGGGTAGTGTGGTTTGGGGAGTGGTAGAGCTGGCAAGCCCTTATGACCACCTGAGTGTGGTTCTGAG 500
[NF-][NF-IL6]
AAGCATGGAAGCATCCAGAGCTCAGGATGATGCCAAGTCTGCAGCCTGGGGATCAGGTGGATGCAGAGTCATTGTGAAAAGGAGGACCCTCACTTTC 600
TGACCCTTCTCCACAGTGCCAGCATGGGTCATTGCTGACCAAGGCCTTGCCATCCTGCCCTAATGGCTGTGGTTCCTAACACATGCAGGGCCTGTGGGT 700
TGAAGCACCAAGGAACCCCTCTTGAGGACAGGGCTACCCTTCCAGGGGCCATGGTCACCGGATGCTGCTTGGGCCGGCAAGACATTTAGACTGTGGCCAG 800
AGTCCAAGGTGGCCCAGCACCTCTTGATCCTCTTCTTCCCACATAACCTTTGACTTCTGCCCGGGTGAAGGTGGGGGAGGCAGGGGCTTTGGGAGTGGGAGTTCTGAGCC 900
CCCACGCTGGGTTTCACCAGATGGGTCTTCACAGTGGCCTGTCACAGTGCCACCACATCTGTAATCTCAAAAAAAAACTAGCTGCCTTGAGCCAGGTGG 1000
AGGGCCTTAAGCGGGAGATGGCTGGACCTTAAGAGAGGGTGGGGCTTGGGCCAACATAGTGAGACCCCAACTCTACAAAAAAAAAATACAAAATTAGCCAGGTGG 1100
ATCACTTAAGGCCAGGAGTTCAAGACCAGCTGGGCCAACATAGTGAGACCCCAACTCTACAAAAAAACTAGCCGTGAGCCTGGAGGTGTACACTTGTA 1200
                                             [TFIID]
GTCCCAGCTACTCAGGAGGCTGAGGTGGGAGGATTGCTTGAGCCTGAGAGGTCAGGATGCAGTGAGCCGTGATTGCCGTACTGCCACTTGGGTGACAGA 1300
GAGACCCTTTCTCAAAAAAAAAAAGGAAAAAGGAAAGAAAAAGGGGCCGGGCACAGTAGCTCACGCCTGTAATCCCAGCACTTTGGGAGGCCG 1400
                                                                                        [AP-2]
AGGCAGGTGGATCACCTGAGGTTGCGAGTTCAAGACCAGCCTGACTAACATGGAGAAACCCGTCTCTACTAAAAATACAAAATTAGCCAGGTGGTGGC 1500
       [AP-1]                                               [TFIID]
```

Figure 7

```
GCATGCCTGCAATCCCAGCTACTCGGGAGGCTGAGGCAGGAGAATTGCTTGAATCCAGGAGACGGAGGTTACGGTGAGCCAAGATTGCACCATTGCACTC 1600
CAGCCTGGGCAACAACAAGAGCGAAACTCTGTCTCAAAAAGAAAAAGAAAAAGAAAAAGAGGAGGTGGTGTAGCCCAGTCACCAACAT 1700
GTTTCACTATAAGAACTCGAGAAGGGCAGGGCAAGATAGTGGCTTCATAGCCAGGTCAGCTCTTACCAAGAAGAAGAAGGAAGGGCAGGACAAATTT 1800
CTTGGGACCAGGTGGGATGACCAGGGTGCAGCTGCCCCTTCGAAGGGGTGGGTGTGTGGAGGATCAAGACCTCTATTTCCCAATACTCTCGTCCCTCTA 1900
TCCCACAGTGACCTATGCTGCGCATATAACCAGCTGTCAGGTCTTTGCCCACTCTGTTCGCCCCTGCTTCCTGCGGCAGGGAGTCCATGTCCTCTCTG 2000
GTTCCCCAGGTTTGCGAGAGTGAGGGGACCACCACGAGCTCCCGATGCCTCCTCTGCTCCTCTGCAGGGGAACTTGCAGATGCCCATGGCAGGGTCGAGAC 2100
TCAAGCCCACTCCCAACCCGCCCGAACTGCCCGCTCTCCCGGTTCCCCCGCATCTGTAACCCGGGCAGAGTTACAGGGGCTGACGCACCCAGGTGCCCTCGGGCA 2300
CTGAACATGCTGACCTGGCCTCTCCCGGTTCCCCCGCATCTGTAACCCGGGCAGAGTTACAGGGGCTGACGCACCCAGGTGCCCTCGGGCA 2300
GGGTGTGCTAAGAATTGGTGTGGGGCTGCACAAAGTCCTCAGCTCCTGTCACCTGAGGCCCAAGAACTGTCCGGGACTCACTTCCTCTCTTCTT 2400
GCTTTAACCGGGGTCGCTCAGCAGCGGCCAGCGCTGCACCCCTTATCCTCTCCCGGTCTGTTCCGTTCCAGATCCTCCAGTTCAGGGGTCGCCAAGTGA 2500
GAGCTGCGCAGCGTGGATTTCGGTACCCAGGGCTGGGCGGGGTACAGCAGCGGCGAGCTGGGTTCCCGGGTGGGCGACTGACAGCCCGAGCCAGGCGA 2600
TACCTCGATCCATCGATGCGCTCGGCGCTCAGCGTGTTCCAGGAAGCAGGGGTTGGGCAAGGCGGGGCCGACCTCCGACTGGGAGGGGCGTATATG 2700
GCGGGCGAGTCCCTATTGGCCAGCCATTTGCGGAGGCGGGCCCTGATTGGCCGGGGGATGCGGGGATGCGGGCGGGGTTAAGCGCGTCGCCACCG 2800
CCCCCGCCTAGGCGAGAGCCCAGAGAGCTGAACCTGCGGCGACCGTCGTACACCATG 2870
```

Figure 14
Phenyl Sepharose profile
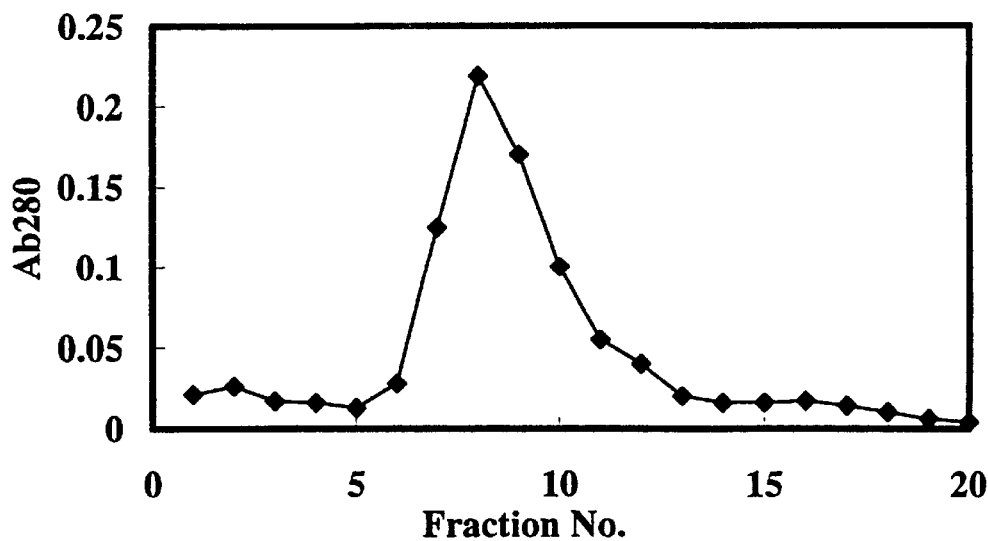
Western blot analysis
12.5% polyacrylamide gel(reducing)
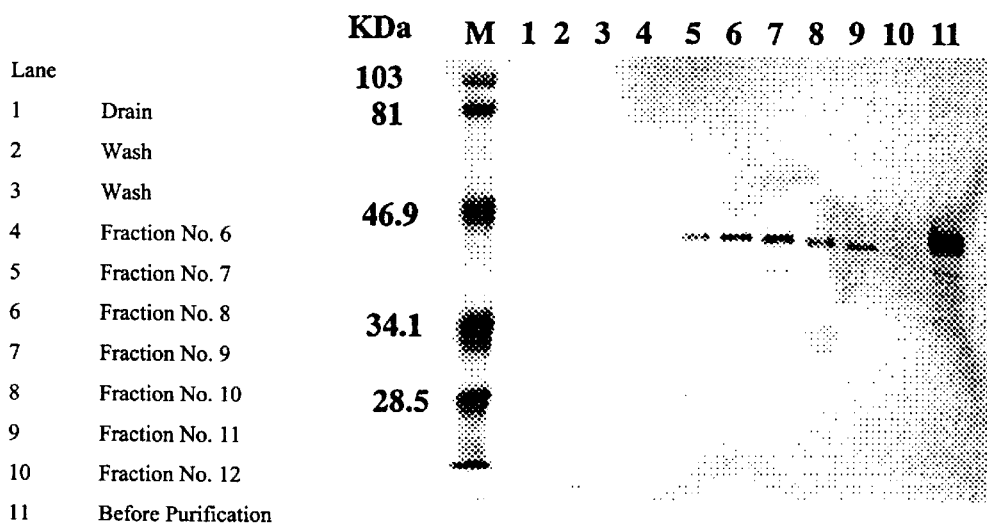
| Lane | |
|---|---|
| 1 | Drain |
| 2 | Wash |
| 3 | Wash |
| 4 | Fraction No. 6 |
| 5 | Fraction No. 7 |
| 6 | Fraction No. 8 |
| 7 | Fraction No. 9 |
| 8 | Fraction No. 10 |
| 9 | Fraction No. 11 |
| 10 | Fraction No. 12 |
| 11 | Before Purification |

SEQUENCE LISTING

<160> NUMBER OF SEQ ID NOS: 43

<210> SEQ ID NO 1
<211> LENGTH: 379
<212> TYPE: PRT
<213> ORGANISM: Human

<400> SEQUENCE: 1

Ala Gly Arg His Pro Pro Val Val Leu Val Pro Gly Asp Leu Gly Asn
 1               5                  10                  15

Gln Leu Glu Ala Lys Leu Asp Lys Pro Thr Val Val His Tyr Leu Cys
            20                  25                  30

Ser Lys Lys Thr Glu Ser Tyr Phe Thr Ile Trp Leu Asn Leu Glu Leu
        35                  40                  45

Leu Leu Pro Val Ile Ile Asp Cys Trp Ile Asp Asn Ile Arg Leu Val
    50                  55                  60

Tyr Asn Lys Thr Ser Arg Ala Thr Gln Phe Pro Asp Gly Val Asp Val
65                  70                  75                  80

Arg Val Pro Gly Phe Gly Lys Thr Phe Ser Leu Glu Phe Leu Asp Pro
                85                  90                  95

Ser Lys Ser Ser Val Gly Ser Tyr Phe His Thr Met Val Glu Ser Leu
            100                 105                 110

Val Gly Trp Gly Tyr Thr Arg Gly Glu Asp Val Arg Gly Ala Pro Tyr
        115                 120                 125

Asp Trp Arg Arg Ala Pro Asn Glu Asn Gly Pro Tyr Phe Leu Ala Leu
    130                 135                 140

Arg Glu Met Ile Glu Glu Met Tyr Gln Leu Tyr Gly Gly Pro Val Val
145                 150                 155                 160

Leu Val Ala His Ser Met Gly Asn Met Tyr Thr Leu Tyr Phe Leu Gln
                165                 170                 175

Arg Gln Pro Gln Ala Trp Lys Asp Lys Tyr Ile Arg Ala Phe Val Ser
            180                 185                 190

Leu Gly Ala Pro Trp Gly Gly Val Ala Lys Thr Leu Arg Val Leu Ala
        195                 200                 205

Ser Gly Asp Asn Asn Arg Ile Pro Val Ile Gly Pro Leu Lys Ile Arg
    210                 215                 220

Glu Gln Gln Arg Ser Ala Val Ser Thr Ser Trp Leu Leu Pro Tyr Asn
225                 230                 235                 240

Tyr Thr Trp Ser Pro Glu Lys Val Phe Val Gln Thr Pro Thr Ile Asn
                245                 250                 255

Tyr Thr Leu Arg Asp Tyr Arg Lys Phe Phe Gln Asp Ile Gly Phe Glu
            260                 265                 270

Asp Gly Trp Leu Met Arg Gln Asp Thr Glu Gly Leu Val Glu Ala Thr
        275                 280                 285

```
Met Pro Pro Gly Val Gln Leu His Cys Leu Tyr Gly Thr Gly Val Pro
    290                 295                 300

Thr Pro Asp Ser Phe Tyr Tyr Glu Ser Phe Pro Asp Arg Asp Pro Lys
305                 310                 315                 320

Ile Cys Phe Gly Asp Gly Asp Gly Thr Val Asn Leu Lys Ser Ala Leu
                325                 330                 335

Gln Cys Gln Ala Trp Gln Ser Arg Gln Glu His Gln Val Leu Leu Gln
                340                 345                 350

Glu Leu Pro Gly Ser Glu His Ile Glu Met Leu Ala Asn Ala Thr Thr
                355                 360                 365

Leu Ala Tyr Leu Lys Arg Val Leu Leu Gly Pro
                370                 375

<210> SEQ ID NO 2
<211> LENGTH: 411
<212> TYPE: PRT
<213> ORGANISM: Human

<400> SEQUENCE: 2

Ala Gly Arg His Pro Val Val Leu Val Pro Gly Asp Leu Gly Asn
1               5                   10                  15

Gln Leu Glu Ala Lys Leu Asp Lys Pro Thr Val Val His Tyr Leu Cys
                20                  25                  30

Ser Lys Lys Thr Glu Ser Tyr Phe Thr Ile Trp Leu Asn Leu Glu Leu
                35                  40                  45

Leu Leu Pro Val Ile Ile Asp Cys Trp Ile Asp Asn Ile Arg Leu Glu
            50                  55                  60

Cys Ser Gly Ala Ile Ser Ala His Tyr Thr Ser Ala Ser Gln Ala Gln
65              70                  75                  80

Ala Leu Leu Leu Pro Gln Thr Pro Asp Asn Trp Asp Tyr Arg Leu Val
                85                  90                  95

Tyr Asn Lys Thr Ser Arg Ala Thr Gln Phe Pro Asp Gly Val Asp Val
                100                 105                 110

Arg Val Pro Gly Phe Gly Lys Thr Phe Ser Leu Glu Phe Leu Asp Pro
                115                 120                 125

Ser Lys Ser Ser Val Gly Ser Tyr Phe His Thr Met Val Glu Ser Leu
                130                 135                 140

Val Gly Trp Gly Tyr Thr Arg Gly Glu Asp Val Arg Gly Ala Pro Tyr
145                 150                 155                 160

Asp Trp Arg Arg Ala Pro Asn Glu Asn Gly Pro Tyr Phe Leu Ala Leu
                165                 170                 175

Arg Glu Met Ile Glu Glu Met Tyr Gln Leu Tyr Gly Gly Pro Val Val
                180                 185                 190

Leu Val Ala His Ser Met Gly Asn Met Tyr Thr Leu Tyr Phe Leu Gln
                195                 200                 205

Arg Gln Pro Gln Ala Trp Lys Asp Lys Tyr Ile Arg Ala Phe Val Ser
                210                 215                 220

Leu Gly Ala Pro Trp Gly Gly Val Ala Lys Thr Leu Arg Val Leu Ala
225                 230                 235                 240

Ser Gly Asp Asn Asn Arg Ile Pro Val Ile Gly Pro Leu Lys Ile Arg
                245                 250                 255

Glu Gln Gln Arg Ser Ala Val Ser Thr Ser Trp Leu Leu Pro Tyr Asn
                260                 265                 270

Tyr Thr Trp Ser Pro Glu Lys Val Phe Val Gln Thr Pro Thr Ile Asn
```

|                 275                 280                 285 |

Tyr Thr Leu Arg Asp Tyr Arg Lys Phe Phe Gln Asp Ile Gly Phe Glu
                290                 295                 300

Asp Gly Trp Leu Met Arg Gln Asp Thr Glu Gly Leu Val Glu Ala Thr
305                 310                 315                 320

Met Pro Pro Gly Val Gln Leu His Cys Leu Tyr Gly Thr Gly Val Pro
                325                 330                 335

Thr Pro Asp Ser Phe Tyr Tyr Glu Ser Phe Pro Asp Arg Asp Pro Lys
                340                 345                 350

Ile Cys Phe Gly Asp Gly Asp Gly Thr Val Asn Leu Lys Ser Ala Leu
                355                 360                 365

Gln Cys Gln Ala Trp Gln Ser Arg Gln Glu His Gln Val Leu Leu Gln
370                 375                 380

Glu Leu Pro Gly Ser Glu His Ile Glu Met Leu Ala Asn Ala Thr Thr
385                 390                 395                 400

Leu Ala Tyr Leu Lys Arg Val Leu Leu Gly Pro
                405                 410

<210> SEQ ID NO 3
<211> LENGTH: 379
<212> TYPE: PRT
<213> ORGANISM: Murine

<400> SEQUENCE: 3

Ala Gln Arg His Pro Pro Val Val Leu Val Pro Gly Asp Leu Gly Asn
1               5                   10                  15

Gln Leu Glu Ala Lys Leu Asp Lys Pro Lys Val Val His Tyr Leu Cys
                20                  25                  30

Ser Lys Lys Thr Asp Ser Tyr Phe Thr Leu Trp Leu Asn Leu Glu Leu
            35                  40                  45

Leu Leu Pro Val Ile Ile Asp Cys Trp Ile Asp Asn Ile Arg Leu Val
        50                  55                  60

Tyr Asn Arg Thr Ser Arg Ala Thr Gln Phe Pro Asp Gly Val Asp Val
65                  70                  75                  80

Arg Val Pro Gly Phe Gly Glu Thr Phe Ser Met Glu Phe Leu Asp Pro
                85                  90                  95

Ser Lys Arg Asn Val Gly Ser Tyr Phe Tyr Thr Met Val Glu Ser Leu
                100                 105                 110

Val Gly Trp Gly Tyr Thr Arg Gly Glu Asp Val Arg Gly Ala Pro Tyr
            115                 120                 125

Asp Trp Arg Arg Ala Pro Asn Glu Asn Gly Pro Tyr Phe Leu Ala Leu
130                 135                 140

Arg Glu Met Ile Glu Glu Met Tyr Gln Met Tyr Gly Gly Pro Val Val
145                 150                 155                 160

Leu Val Ala His Ser Met Gly Asn Val Tyr Met Leu Tyr Phe Leu Gln
                165                 170                 175

Arg Gln Pro Gln Val Trp Lys Asp Lys Tyr Ile His Ala Phe Val Ser
                180                 185                 190

Leu Gly Ala Pro Trp Gly Gly Val Ala Lys Thr Leu Arg Val Leu Ala
            195                 200                 205

Ser Gly Asp Asn Asn Arg Ile Pro Val Ile Gly Pro Leu Lys Ile Arg
        210                 215                 220

Glu Gln Gln Arg Ser Ala Val Ser Thr Ser Trp Leu Leu Pro Tyr Asn
225                 230                 235                 240

His Thr Trp Ser His Glu Lys Val Phe Val Tyr Thr Pro Thr Thr Asn
            245                 250                 255

Tyr Thr Leu Arg Asp Tyr His Arg Phe Phe Arg Asp Ile Gly Phe Glu
            260                 265                 270

Asp Gly Trp Phe Met Arg Gln Asp Thr Glu Gly Leu Val Glu Ala Met
            275                 280                 285

Thr Pro Pro Gly Val Glu Leu His Cys Leu Tyr Gly Thr Gly Val Pro
            290                 295                 300

Thr Pro Asn Ser Phe Tyr Tyr Glu Ser Phe Pro Asp Arg Asp Pro Lys
305                 310                 315                 320

Ile Cys Phe Gly Asp Gly Asp Gly Thr Val Asn Leu Glu Ser Val Leu
            325                 330                 335

Gln Cys Gln Ala Trp Gln Ser Arg Gln His Arg Val Ser Leu Gln
            340                 345                 350

Glu Leu Pro Gly Ser Glu His Ile Glu Met Leu Ala Asn Ala Thr Thr
            355                 360                 365

Leu Ala Tyr Leu Lys Arg Val Leu Leu Glu Pro
            370                 375

<210> SEQ ID NO 4
<211> LENGTH: 382
<212> TYPE: PRT
<213> ORGANISM: Human

<400> SEQUENCE: 4

Ala Leu Pro Ala Gly Arg His Pro Pro Val Val Leu Val Pro Gly Asp
  1               5                  10                  15

Leu Gly Asn Gln Leu Glu Ala Lys Leu Asp Lys Pro Thr Val Val His
            20                  25                  30

Tyr Leu Cys Ser Lys Lys Thr Glu Ser Tyr Phe Thr Ile Trp Leu Asn
        35                  40                  45

Leu Glu Leu Leu Leu Pro Val Ile Ile Asp Cys Trp Ile Asp Asn Ile
    50                  55                  60

Arg Leu Val Tyr Asn Lys Thr Ser Arg Ala Thr Gln Phe Pro Asp Gly
65                  70                  75                  80

Val Asp Val Arg Val Pro Gly Phe Gly Lys Thr Phe Ser Leu Glu Phe
                85                  90                  95

Leu Asp Pro Ser Lys Ser Ser Val Gly Ser Tyr Phe His Thr Met Val
            100                 105                 110

Glu Ser Leu Val Gly Trp Gly Tyr Thr Arg Gly Glu Asp Val Arg Gly
        115                 120                 125

Ala Pro Tyr Asp Trp Arg Arg Ala Pro Asn Glu Asn Gly Pro Tyr Phe
    130                 135                 140

Leu Ala Leu Arg Glu Met Ile Glu Glu Met Tyr Gln Leu Tyr Gly Gly
145                 150                 155                 160

Pro Val Val Leu Val Ala His Ser Met Gly Asn Met Tyr Thr Leu Tyr
                165                 170                 175

Phe Leu Gln Arg Gln Pro Gln Ala Trp Lys Asp Lys Tyr Ile Arg Ala
            180                 185                 190

Phe Val Ser Leu Gly Ala Pro Trp Gly Gly Val Ala Lys Thr Leu Arg
        195                 200                 205

Val Leu Ala Ser Gly Asp Asn Asn Arg Ile Pro Val Ile Gly Pro Leu
    210                 215                 220

Lys Ile Arg Glu Gln Gln Arg Ser Ala Val Ser Thr Ser Trp Leu Leu
225                 230                 235                 240

```
Pro Tyr Asn Tyr Thr Trp Ser Pro Glu Lys Val Phe Val Gln Thr Pro
                245                 250                 255

Thr Ile Asn Tyr Thr Leu Arg Asp Tyr Arg Lys Phe Phe Gln Asp Ile
            260                 265                 270

Gly Phe Glu Asp Gly Trp Leu Met Arg Gln Asp Thr Glu Gly Leu Val
        275                 280                 285

Glu Ala Thr Met Pro Pro Gly Val Gln Leu His Cys Leu Tyr Gly Thr
    290                 295                 300

Gly Val Pro Thr Pro Asp Ser Phe Tyr Tyr Glu Ser Phe Pro Asp Arg
305                 310                 315                 320

Asp Pro Lys Ile Cys Phe Gly Asp Gly Asp Gly Thr Val Asn Leu Lys
                325                 330                 335

Ser Ala Leu Gln Cys Gln Ala Trp Gln Ser Arg Gln Glu His Gln Val
            340                 345                 350

Leu Leu Gln Glu Leu Pro Gly Ser Glu His Ile Glu Met Leu Ala Asn
        355                 360                 365

Ala Thr Thr Leu Ala Tyr Leu Lys Arg Val Leu Leu Gly Pro
    370                 375                 380

<210> SEQ ID NO 5
<211> LENGTH: 414
<212> TYPE: PRT
<213> ORGANISM: Human

<400> SEQUENCE: 5

Ala Leu Pro Ala Gly Arg His Pro Val Val Leu Val Pro Gly Asp
1               5                   10                  15

Leu Gly Asn Gln Leu Glu Ala Lys Leu Asp Lys Pro Thr Val Val His
                20                  25                  30

Tyr Leu Cys Ser Lys Lys Thr Glu Ser Tyr Phe Thr Ile Trp Leu Asn
            35                  40                  45

Leu Glu Leu Leu Leu Pro Val Ile Ile Asp Cys Trp Ile Asp Asn Ile
        50                  55                  60

Arg Leu Glu Cys Ser Gly Ala Ile Ser Ala His Tyr Thr Ser Ala Ser
65                  70                  75                  80

Gln Ala Gln Ala Leu Leu Leu Pro Gln Thr Pro Asp Asn Trp Asp Tyr
                85                  90                  95

Arg Leu Val Tyr Asn Lys Thr Ser Arg Ala Thr Gln Phe Pro Asp Gly
            100                 105                 110

Val Asp Val Arg Val Pro Gly Phe Gly Lys Thr Phe Ser Leu Glu Phe
        115                 120                 125

Leu Asp Pro Ser Lys Ser Ser Val Gly Ser Tyr Phe His Thr Met Val
    130                 135                 140

Glu Ser Leu Val Gly Trp Gly Tyr Thr Arg Gly Glu Asp Val Arg Gly
145                 150                 155                 160

Ala Pro Tyr Asp Trp Arg Arg Ala Pro Asn Glu Asn Gly Pro Tyr Phe
                165                 170                 175

Leu Ala Leu Arg Glu Met Ile Glu Glu Met Tyr Gln Leu Tyr Gly Gly
            180                 185                 190

Pro Val Val Leu Val Ala His Ser Met Gly Asn Met Tyr Thr Leu Tyr
        195                 200                 205

Phe Leu Gln Arg Gln Pro Gln Ala Trp Lys Asp Lys Tyr Ile Arg Ala
    210                 215                 220

Phe Val Ser Leu Gly Ala Pro Trp Gly Gly Val Ala Lys Thr Leu Arg
```

-continued

```
            225                 230                 235                 240

Val Leu Ala Ser Gly Asp Asn Asn Arg Ile Pro Val Ile Gly Pro Leu
                245                 250                 255

Lys Ile Arg Glu Gln Gln Arg Ser Ala Val Ser Thr Ser Trp Leu Leu
                260                 265                 270

Pro Tyr Asn Tyr Thr Trp Ser Pro Glu Lys Val Phe Val Gln Thr Pro
                275                 280                 285

Thr Ile Asn Tyr Thr Leu Arg Asp Tyr Arg Lys Phe Phe Gln Asp Ile
                290                 295                 300

Gly Phe Glu Asp Gly Trp Leu Met Arg Gln Asp Thr Glu Gly Leu Val
305                 310                 315                 320

Glu Ala Thr Met Pro Pro Gly Val Gln Leu His Cys Leu Tyr Gly Thr
                325                 330                 335

Gly Val Pro Thr Pro Asp Ser Phe Tyr Tyr Glu Ser Phe Pro Asp Arg
                340                 345                 350

Asp Pro Lys Ile Cys Phe Gly Asp Gly Asp Gly Thr Val Asn Leu Lys
                355                 360                 365

Ser Ala Leu Gln Cys Gln Ala Trp Gln Ser Arg Gln Glu His Gln Val
                370                 375                 380

Leu Leu Gln Glu Leu Pro Gly Ser Glu His Ile Glu Met Leu Ala Asn
385                 390                 395                 400

Ala Thr Thr Leu Ala Tyr Leu Lys Arg Val Leu Leu Gly Pro
                405                 410

<210> SEQ ID NO 6
<211> LENGTH: 412
<212> TYPE: PRT
<213> ORGANISM: Human

<400> SEQUENCE: 6

Met Gly Leu His Leu Arg Pro Tyr Arg Val Gly Leu Leu Pro Asp Gly
1               5                   10                  15

Leu Leu Phe Leu Leu Leu Leu Leu Met Leu Leu Ala Asp Pro Ala Leu
                20                  25                  30

Pro Ala Gly Arg His Pro Pro Val Val Leu Val Pro Gly Asp Leu Gly
                35                  40                  45

Asn Gln Leu Glu Ala Lys Leu Asp Lys Pro Thr Val Val His Tyr Leu
                50                  55                  60

Cys Ser Lys Lys Thr Glu Ser Tyr Phe Thr Ile Trp Leu Asn Leu Glu
65                  70                  75                  80

Leu Leu Leu Pro Val Ile Ile Asp Cys Trp Ile Asp Asn Ile Arg Leu
                85                  90                  95

Val Tyr Asn Lys Thr Ser Arg Ala Thr Gln Phe Pro Asp Gly Val Asp
                100                 105                 110

Val Arg Val Pro Gly Phe Gly Lys Thr Phe Ser Leu Glu Phe Leu Asp
                115                 120                 125

Pro Ser Lys Ser Ser Val Gly Ser Tyr Phe His Thr Met Val Glu Ser
                130                 135                 140

Leu Val Gly Trp Gly Tyr Thr Arg Gly Glu Asp Val Arg Gly Ala Pro
145                 150                 155                 160

Tyr Asp Trp Arg Arg Ala Pro Asn Glu Asn Gly Pro Tyr Phe Leu Ala
                165                 170                 175

Leu Arg Glu Met Ile Glu Glu Met Tyr Gln Leu Tyr Gly Gly Pro Val
                180                 185                 190
```

-continued

```
Val Leu Val Ala His Ser Met Gly Asn Met Tyr Thr Leu Tyr Phe Leu
            195                 200                 205

Gln Arg Gln Pro Gln Ala Trp Lys Asp Lys Tyr Ile Arg Ala Phe Val
        210                 215                 220

Ser Leu Gly Ala Pro Trp Gly Val Ala Lys Thr Leu Arg Val Leu
225                 230                 235                 240

Ala Ser Gly Asp Asn Asn Arg Ile Pro Val Ile Gly Pro Leu Lys Ile
                245                 250                 255

Arg Glu Gln Gln Arg Ser Ala Val Ser Thr Ser Trp Leu Leu Pro Tyr
            260                 265                 270

Asn Tyr Thr Trp Ser Pro Glu Lys Val Phe Val Gln Thr Pro Thr Ile
            275                 280                 285

Asn Tyr Thr Leu Arg Asp Tyr Arg Lys Phe Phe Gln Asp Ile Gly Phe
            290                 295                 300

Glu Asp Gly Trp Leu Met Arg Gln Asp Thr Glu Gly Leu Val Glu Ala
305                 310                 315                 320

Thr Met Pro Pro Gly Val Gln Leu His Cys Leu Tyr Gly Thr Gly Val
                325                 330                 335

Pro Thr Pro Asp Ser Phe Tyr Tyr Glu Ser Phe Pro Asp Arg Asp Pro
                340                 345                 350

Lys Ile Cys Phe Gly Asp Gly Asp Gly Thr Val Asn Leu Lys Ser Ala
            355                 360                 365

Leu Gln Cys Gln Ala Trp Gln Ser Arg Gln Glu His Gln Val Leu Leu
        370                 375                 380

Gln Glu Leu Pro Gly Ser Glu His Ile Glu Met Leu Ala Asn Ala Thr
385                 390                 395                 400

Thr Leu Ala Tyr Leu Lys Arg Val Leu Leu Gly Pro
                405                 410
```

<210> SEQ ID NO 7
<211> LENGTH: 444
<212> TYPE: PRT
<213> ORGANISM: Human

<400> SEQUENCE: 7

```
Met Gly Leu His Leu Arg Pro Tyr Arg Val Gly Leu Leu Pro Asp Gly
1               5                   10                  15

Leu Leu Phe Leu Leu Leu Leu Met Leu Leu Ala Asp Pro Ala Leu
            20                  25                  30

Pro Ala Gly Arg His Pro Pro Val Leu Val Pro Gly Asp Leu Gly
        35                  40                  45

Asn Gln Leu Glu Ala Lys Leu Asp Lys Pro Thr Val Val His Tyr Leu
    50                  55                  60

Cys Ser Lys Lys Thr Glu Ser Tyr Phe Thr Ile Trp Leu Asn Leu Glu
65              70                  75                  80

Leu Leu Leu Pro Val Ile Ile Asp Cys Trp Ile Asp Asn Ile Arg Leu
                85                  90                  95

Glu Cys Ser Gly Ala Ile Ser Ala His Tyr Thr Ser Ala Ser Gln Ala
            100                 105                 110

Gln Ala Leu Leu Leu Pro Gln Thr Pro Asp Asn Trp Asp Tyr Arg Leu
        115                 120                 125

Val Tyr Asn Lys Thr Ser Arg Ala Thr Gln Phe Pro Asp Gly Val Asp
    130                 135                 140

Val Arg Val Pro Gly Phe Gly Lys Thr Phe Ser Leu Glu Phe Leu Asp
145                 150                 155                 160
```

-continued

```
Pro Ser Lys Ser Ser Val Gly Ser Tyr Phe His Thr Met Val Glu Ser
                165                 170                 175
Leu Val Gly Trp Gly Tyr Thr Arg Gly Glu Asp Val Arg Gly Ala Pro
            180                 185                 190
Tyr Asp Trp Arg Arg Ala Pro Asn Glu Asn Gly Pro Tyr Phe Leu Ala
        195                 200                 205
Leu Arg Glu Met Ile Glu Met Tyr Gln Leu Tyr Gly Gly Pro Val
    210                 215                 220
Val Leu Val Ala His Ser Met Gly Asn Met Tyr Thr Leu Tyr Phe Leu
225                 230                 235                 240
Gln Arg Gln Pro Gln Ala Trp Lys Asp Lys Tyr Ile Arg Ala Phe Val
                245                 250                 255
Ser Leu Gly Ala Pro Trp Gly Val Ala Lys Thr Leu Arg Val Leu
            260                 265                 270
Ala Ser Gly Asp Asn Asn Arg Ile Pro Val Ile Gly Pro Leu Lys Ile
        275                 280                 285
Arg Glu Gln Gln Arg Ser Ala Val Ser Thr Ser Trp Leu Leu Pro Tyr
    290                 295                 300
Asn Tyr Thr Trp Ser Pro Glu Lys Val Phe Val Gln Thr Pro Thr Ile
305                 310                 315                 320
Asn Tyr Thr Leu Arg Asp Tyr Arg Lys Phe Phe Gln Asp Ile Gly Phe
                325                 330                 335
Glu Asp Gly Trp Leu Met Arg Gln Asp Thr Glu Gly Leu Val Glu Ala
            340                 345                 350
Thr Met Pro Pro Gly Val Gln Leu His Cys Leu Tyr Gly Thr Gly Val
        355                 360                 365
Pro Thr Pro Asp Ser Phe Tyr Tyr Glu Ser Phe Pro Asp Arg Asp Pro
    370                 375                 380
Lys Ile Cys Phe Gly Asp Gly Asp Gly Thr Val Asn Leu Lys Ser Ala
285                 390                 395                 400
Leu Gln Cys Gln Ala Trp Gln Ser Arg Gln Glu His Gln Val Leu Leu
                405                 410                 415
Gln Glu Leu Pro Gly Ser Glu His Ile Glu Met Leu Ala Asn Ala Thr
            420                 425                 430
Thr Leu Ala Tyr Leu Lys Arg Val Leu Leu Gly Pro
        435                 440

<210> SEQ ID NO 8
<211> LENGTH: 412
<212> TYPE: PRT
<213> ORGANISM: Murine

<400> SEQUENCE: 8

Met Asp Arg His Leu Cys Thr Cys Arg Glu Thr Gln Leu Arg Ser Gly
1               5                   10                  15
Leu Leu Leu Pro Leu Phe Leu Leu Met Met Leu Ala Asp Leu Thr Leu
                20                  25                  30
Pro Ala Gln Arg His Pro Pro Val Val Leu Val Pro Gly Asp Leu Gly
            35                  40                  45
Asn Gln Leu Glu Ala Lys Leu Asp Lys Pro Lys Val Val His Tyr Leu
        50                  55                  60
Cys Ser Lys Lys Thr Asp Ser Tyr Phe Thr Leu Trp Leu Asn Leu Glu
65                  70                  75                  80
Leu Leu Leu Pro Val Ile Ile Asp Cys Trp Ile Asp Asn Ile Arg Leu
```

-continued

```
                    85                  90                  95
Val Tyr Asn Arg Thr Ser Arg Ala Thr Gln Phe Pro Asp Gly Val Asp
                100                 105                 110
Val Arg Val Pro Gly Phe Gly Glu Thr Phe Ser Met Glu Phe Leu Asp
            115                 120                 125
Pro Ser Lys Arg Asn Val Gly Ser Tyr Phe Tyr Thr Met Val Glu Ser
        130                 135                 140
Leu Val Gly Trp Gly Tyr Thr Arg Gly Glu Asp Val Arg Gly Ala Pro
145                 150                 155                 160
Tyr Asp Trp Arg Arg Ala Pro Asn Glu Asn Gly Pro Tyr Phe Leu Ala
                165                 170                 175
Leu Arg Glu Met Ile Glu Met Tyr Gln Met Tyr Gly Gly Pro Val
            180                 185                 190
Val Leu Val Ala His Ser Met Gly Asn Val Tyr Met Leu Tyr Phe Leu
            195                 200                 205
Gln Arg Gln Pro Gln Val Trp Lys Asp Lys Tyr Ile His Ala Phe Val
        210                 215                 220
Ser Leu Gly Ala Pro Trp Gly Gly Val Ala Lys Thr Leu Arg Val Leu
225                 230                 235                 240
Ala Ser Gly Asp Asn Asn Arg Ile Pro Val Ile Gly Pro Leu Lys Ile
                245                 250                 255
Arg Glu Gln Gln Arg Ser Ala Val Ser Thr Ser Trp Leu Leu Pro Tyr
            260                 265                 270
Asn His Thr Trp Ser His Glu Lys Val Phe Val Tyr Thr Pro Thr Thr
        275                 280                 285
Asn Tyr Thr Leu Arg Asp Tyr His Arg Phe Phe Arg Asp Ile Gly Phe
        290                 295                 300
Glu Asp Gly Trp Phe Met Arg Gln Asp Thr Glu Gly Leu Val Glu Ala
305                 310                 315                 320
Met Thr Pro Pro Gly Val Glu Leu His Cys Leu Tyr Gly Thr Gly Val
                325                 330                 335
Pro Thr Pro Asn Ser Phe Tyr Tyr Glu Ser Phe Pro Asp Arg Asp Pro
            340                 345                 350
Lys Ile Cys Phe Gly Asp Gly Asp Gly Thr Val Asn Leu Glu Ser Val
        355                 360                 365
Leu Gln Cys Gln Ala Trp Gln Ser Arg Gln Glu His Arg Val Ser Leu
    370                 375                 380
Gln Glu Leu Pro Gly Ser Glu His Ile Glu Met Leu Ala Asn Ala Thr
385                 390                 395                 400
Thr Leu Ala Tyr Leu Lys Arg Val Leu Leu Glu Pro
                405                 410
```

<210> SEQ ID NO 9
<211> LENGTH: 30
<212> TYPE: PRT
<213> ORGANISM: Unknown
<220> FEATURE:
<223> OTHER INFORMATION: Unsure (signal peptide)

<400> SEQUENCE: 9

```
Met Gly Leu His Leu Arg Pro Tyr Arg Val Gly Leu Leu Pro Asp Gly
  1               5                  10                  15
Leu Leu Phe Leu Leu Leu Leu Leu Met Leu Leu Ala Asp Pro
            20                  25                  30
```

```
<210> SEQ ID NO 10
<211> LENGTH: 33
<212> TYPE: PRT
<213> ORGANISM: Unknown
<220> FEATURE:
<223> OTHER INFORMATION: Unsure (signal peptide)

<400> SEQUENCE: 10

Met Gly Leu His Leu Arg Pro Tyr Arg Val Gly Leu Leu Pro Asp Gly
 1               5                  10                  15

Leu Leu Phe Leu Leu Leu Leu Met Leu Leu Ala Asp Pro Ala Leu
            20                  25                  30

Pro

<210> SEQ ID NO 11
<211> LENGTH: 33
<212> TYPE: PRT
<213> ORGANISM: Unknown
<220> FEATURE:
<223> OTHER INFORMATION: Unsure (signal peptide)

<400> SEQUENCE: 11

Met Asp Arg His Leu Cys Thr Cys Arg Glu Thr Gln Leu Arg Ser Gly
 1               5                  10                  15

Leu Leu Leu Pro Leu Phe Leu Leu Met Met Leu Ala Asp Leu Thr Leu
            20                  25                  30

Pro

<210> SEQ ID NO 12
<211> LENGTH: 1137
<212> TYPE: DNA
<213> ORGANISM: Human

<400> SEQUENCE: 12
gccggacgtc accccccagt ggtgctggtc cctggtgatt tgggtaacca actggaagcc      60
aagctggaca gccgacagt ggtgcactac ctctgctcca agaagaccga aagctacttc     120
acaatctggc tgaacctgga actgctgctg cctgtcatca ttgactgctg gattgacaat     180
atcaggctgg tttacaacaa acatccagg gccacccagt ttcctgatgg tgtggatgta     240
cgtgtccctg gctttgggaa gaccttctca ctggagttcc tgaccccag caaaagcagc     300
gtgggttcct atttccacac catggtggag agccttgtgg gctggggcta cacgcgggt     360
gaggatgtcc gagggctccc ctatgactgg cgccagccc aaatgaaaa cgggccctac     420
ttcctggccc tccgcgagat gatcgaggag atgtaccagc tgtatggggg ccccgtggtg     480
ctggttgccc acagtatggg caacatgtac acgctctact ttctgcagcg gcagccgcag     540
gcctggaagg acaagtatat ccgggccttc gtgtcactgg gtgcgccctg ggggggcgtg     600
gccaagaccc tgcgcgtcct ggcttcagga gacaacaacc ggatcccagt catcgggccc     660
ctgaagatcc gggagcagca gcggtcagct gtctccacca gctggctgct gccctacaac     720
tacacatggt cacctgagaa ggtgttcgtg cagacaccca caatcaacta cacactgcgg     780
gactaccgca agttcttcca ggacatcggc tttgaagatg gctggctcat gcggcaggac     840
acagaagggc tggtggaagc cacgatgcca cctggcgtgc agctgcactg cctctatggc     900
actggcgtcc ccacaccaga ctccttctac tatgagagct ccctgaccg tgaccctaaa     960
atctgctttg gtgacggcga tggtactgtg aacttgaaga gtgccctgca gtgccaggcc    1020
tggcagagcc gccaggagca ccaagtgttg ctgcaggagc tgccaggcag cgagcacatc    1080
```

```
gagatgctgg ccaacgccac caccctggcc tatctgaaac gtgtgctcct tgggccc        1137
```

<210> SEQ ID NO 13
<211> LENGTH: 1233
<212> TYPE: DNA
<213> ORGANISM: Human

<400> SEQUENCE: 13

```
gccggacgtc acccccccagt ggtgctggtc cctggtgatt tgggtaacca actggaagcc     60
aagctggaca agccgacagt ggtgcactac ctctgctcca agaagaccga aagctacttc    120
acaatctggc tgaacctgga actgctgctg cctgtcatca ttgactgctg gattgacaat    180
atcaggctgg agtgcagtgg cgcaatctcg gctcactaca cctctgcctc ccaggctcaa    240
gcacttctcc tgcctcagac tccggataac tgggattaca ggctggttta caacaaaaca    300
tccagggcca cccagtttcc tgatggtgtg atgtacgtg tccctggctt tgggaagacc     360
ttctcactgg agttcctgga ccccagcaaa agcagcgtgg gttcctatttt ccacaccatg   420
gtggagagcc ttgtgggctg ggctacaca cggggtgagg atgtccgagg ggctccctat    480
gactggcgcc gagccccaaa tgaaaacggg ccctacttcc tggccctccg cgagatgatc    540
gaggagatgt accagctgta tgggggcccc gtggtgctgg ttgcccacag tatgggcaac    600
atgtacacgc tctactttct gcagcggcag ccgcaggcct ggaaggacaa gtatatccgg    660
gccttcgtgt cactgggtgc gccctggggg ggcgtggcca agaccctgcg cgtcctggct    720
tcaggagaca caaccggat cccagtcatc gggcccctga gatccggga gcagcagcgg     780
tcagctgtct ccaccagctg gctgctgccc tacaactaca catggtcacc tgagaaggtg    840
ttcgtgcaga cacccacaat caactacaca ctgcgggact accgcaagtt cttccaggac    900
atcggctttg aagatggctg gctcatgcgg caggacacag aagggctggt ggaagccacg    960
atgccacctg cgtgcagct gcactgcctc tatggtactg cgtcccccac accagactcc   1020
ttctactatg agagcttccc tgaccgtgac cctaaaatct gctttggtga cggcgatggt   1080
actgtgaact tgaagagtgc cctgcagtgc caggcctggc agagccgcca ggagcaccaa   1140
gtgttgctgc aggagctgcc aggcagcgag cacatcgaga tgctggccaa cgccaccacc   1200
ctggcctatc tgaaacgtgt gctccttggg ccc                                1233
```

<210> SEQ ID NO 14
<211> LENGTH: 1137
<212> TYPE: DNA
<213> ORGANISM: Murine

<400> SEQUENCE: 14

```
gcccaacgtc acccccccggt ggtgctggtg cctggtgatt tgggtaacca gttggaagca    60
aagctggata agccaaaggt tgtacactac ctttgctcca agaagacgga cagctacttc    120
acactctggc tgaatctgga actgcttctg cctgttatca ttgactgctg gattgacaat    180
atcaggctgg tttacaacag aacatctcgg gccacccagt ttcccgatgg tgtggacgtg    240
cgtgtccctg gctttgggga acatttttct atggaattcc tagaccccag caagaggaat    300
gtgggttcct atttctacac tatggtggag agccttgtgg ctggggcta cacacgggt     360
gaagacgttc gaggtgctcc ctatgattgg cggcgagccc caaatgaaaa cgggccctac    420
ttcttggccc tgcgagagat gatcgaggag atgtaccaga tgtatggggg ccccgtggtg    480
ctggtcgccc acagcatggg caacgtgtac atgctctact ttctgcagcg gcagccacaa    540
gtctggaagg acaaatatat ccatgccttc gtctcactgg gggcgccctg ggggggcgtg    600
```

```
gccaagacgc tgcgtgtcct ggcctcagga gacaacaatc gcattccgt cattgggcca      660 ctgaagatcc gggaacagca gcgatctgcc gtctctacca gctggctact gccatacaac     720
cacacttggt cacatgaaaa ggtatttgta tacacaccca cgactaacta cacgctccgg     780
gactatcacc ggttcttccg ggacatcggt ttcgaagatg gctggttcat gcggcaggac     840
acagaagggc tggttgaagc catgacgcca cccggggtgg agctgcactg cttgtatggc     900
actggtgttc ccacgccaaa ctctttctac tacgagagct ttcctgatcg ggaccccaaa     960
atctgcttcg gcgatggtga cggcacgtg aacctggaga gcgtcctgca gtgccaagcc     1020
tggcagagcc gccaagagca cagagtatca ttgcaggagc tgccgggaag cgagcacatt     1080
gagatgctag ccaatgccac caccttggct tatctgaaac gtgtgcttct ggaacct       1137
```

<210> SEQ ID NO 15
<211> LENGTH: 1146
<212> TYPE: DNA
<213> ORGANISM: Human

<400> SEQUENCE: 15

```
gcgctcccgg ccggacgtca cccccagtg gtgctggtcc ctggtgattt gggtaaccaa      60
ctggaagcca agctggacaa gccgacagtg gtgcactacc tctgctccaa gaagaccgaa     120
agctacttca caatctggct gaacctggaa ctgctgctgc tgtcatcat tgactgctgg     180 attgacaata tcaggctggt ttacaacaaa acatccaggg ccacccagtt tcctgatggt     240
gtggatgtac gtgtccctgg cttttgggaag accttctcac tggagttcct ggaccccagc    300
aaaagcagcg tgggttccta tttccacacc atggtggaga gccttgtggg ctggggctac    360
acacggggtg aggatgtccg aggggctccc tatgactggc gccgagcccc aaatgaaaac    420
gggccctact cctggccct ccgcgagatg atcgaggaga tgtaccagct gtatgggggc    480
cccgtggtgc tggttgccca gtatgggc aacatgtaca cgctctactt tctgcagcgg    540
cagccgcagg cctggaagga caagtatatc cgggccttcg tgtcactggg tgcgccctgg    600
gggggcgtgg ccaagaccct gcgcgtcctg gcttcaggag acaacaaccg gatcccagtc    660
atcgggcccc tgaagatccg ggagcagcag cggtcagctg tctccaccag ctggctgctg    720
ccctacaact acacatggtc acctgagaag gtgttcgtgc agacacccac aatcaactac    780
acactgcggg actaccgcaa gttcttccag gacatcggct ttgaagatgg ctggctcatg    840
cggcaggaca cagaagggct ggtggaagcc acgatgccac ctggcgtgca gctgcactgc    900
ctctatggca ctggcgtccc cacaccagac tccttctact atgagagctt ccctgaccgt    960
gaccctaaaa tctgctttgg tgacggcgat ggtactgtga acttgaagag tgccctgcag   1020
tgccaggcct ggagagccc caggagcac caagtgttgc tgcaggagct gccaggcagc     1080
gagcacatcg agatgctggc caacgccacc accctggcct atctgaaacg tgtgctcctt    1140
gggccc                                                              1146
```

<210> SEQ ID NO 16
<211> LENGTH: 1242
<212> TYPE: DNA
<213> ORGANISM: Human

<400> SEQUENCE: 16

```
gcgctcccgg ccggacgtca cccccagtg gtgctggtcc ctggtgattt gggtaaccaa      60
ctggaagcca agctggacaa gccgacagtg gtgcactacc tctgctccaa gaagaccgaa     120
```

-continued

| | |
|---|---|
| agctacttca caatctggct gaacctggaa ctgctgctgc ctgtcatcat tgactgctgg | 180 |
| attgacaata tcaggctgga gtgcagtggc gcaatctcgg ctcactacac ctctgcctcc | 240 |
| caggctcaag cacttctcct gcctcagact ccggataact gggattacag gctggtttac | 300 |
| aacaaaacat ccagggccac ccagtttcct gatggtgtgg atgtacgtgt ccctggcttt | 360 |
| gggaagacct tctcactgga gttcctggac cccagcaaaa gcagcgtggg ttcctatttc | 420 |
| cacaccatgg tggagagcct tgtgggctgg ggctacacac ggggtgagga tgtccgaggg | 480 |
| gctccctatg actggcgccg agccccaaat gaaaacgggc cctacttcct ggccctccgc | 540 |
| gagatgatcg aggagatgta ccagctgtat gggggccccg tggtgctggt tgcccacagt | 600 |
| atgggcaaca tgtacacgct ctactttctg cagcggcagc cgcaggcctg gaaggacaag | 660 |
| tatatccggg ccttcgtgtc actgggtgcg ccctgggggg gcgtggccaa gaccctgcgc | 720 |
| gtcctggctt caggagacaa caaccggatc ccagtcatcg ggcccctgaa gatccgggag | 780 |
| cagcagcggt cagctgtctc caccagctgg ctgctgccct acaactacac atggtcacct | 840 |
| gagaaggtgt tcgtgcagac acccacaatc aactacacac tgcgggacta ccgcaagttc | 900 |
| ttccaggaca tcggctttga agatggctgg ctcatgcggc aggacacaga agggctggtg | 960 |
| gaagccacga tgccacctgg cgtgcagctg cactgcctct atggtactgg cgtccccaca | 1020 |
| ccagactcct tctactatga gagcttccct gaccgtgacc ctaaaatctg ctttggtgac | 1080 |
| ggcgatggta ctgtgaactt gaagagtgcc ctgcagtgcc aggcctggca gagccgccag | 1140 |
| gagcaccaag tgttgctgca ggagctgcca ggcagcgagc acatcgagat gctggccaac | 1200 |
| gccaccaccc tggcctatct gaaacgtgtg ctccttgggc cc | 1242 |

<210> SEQ ID NO 17
<211> LENGTH: 1236
<212> TYPE: DNA
<213> ORGANISM: Human

<400> SEQUENCE: 17

| | |
|---|---|
| atgggcctcc acctccgccc ctaccgtgtg gggctgctcc cggatggcct cctgttcctc | 60 |
| ttgctgctgc taatgctgct cgcggaccca gcgctcccgg ccggacgtca cccccagtg | 120 |
| gtgctggtcc tggtgatttg ggtaaccaa ctggaagcca agctggacaa gccgacagtg | 180 |
| gtgcactacc tctgctccaa gaagaccgaa agctacttca caatctggct gaacctggaa | 240 |
| ctgctgctgc ctgtcatcat tgactgctgg attgacaata tcaggctggt ttacaacaaa | 300 |
| acatccaggg ccacccagtt tcctgatggt gtggatgtac gtgtccctgg ctttgggaag | 360 |
| accttctcac tggagttcct ggaccccagc aaaagcagcg tgggttccta tttccacacc | 420 |
| atggtggaga gccttgtggg ctggggctac acacgggtg aggatgtccg aggggctccc | 480 |
| tatgactggc gccagccccc aaatgaaaac gggccctact tcctggccct ccgcgagatg | 540 |
| atcgaggaga tgtaccagct gtatggggc cccgtggtgc tggttgccca gtatgggc | 600 |
| aacatgtaca cgctctactt tctgcagcgg cagccgcagg cctggaagga caagtatatc | 660 |
| cgggccttcg tgtcactggg tgcgccctgg ggggcgtgg ccaagaccct gcgcgtcctg | 720 |
| gcttcaggag acaacaaccg gatcccagtc atcgggcccc tgaagatccg ggagcagcag | 780 |
| cggtcagctg tctccaccag ctggctgctg ccctacaact acacatggtc acctgagaag | 840 |
| gtgttcgtgc agacacccac aatcaactac acactgcggg actaccgcaa gttcttccag | 900 |
| gacatcggct ttgaagatgg ctggctcatg cggcaggaca cagaagggct ggtggaagcc | 960 |
| acgatgccac ctggcgtgca gctgcactgc ctctatggca ctggcgtccc cacaccagac | 1020 |

```
tccttctact atgagagctt ccctgaccgt gaccctaaaa tctgctttgg tgacggcgat    1080
ggtactgtga acttgaagag tgccctgcag tgccaggcct ggcagagccg ccaggagcac    1140
caagtgttgc tgcaggagct gccaggcagc gagcacatcg agatgctggc caacgccacc    1200
accctggcct atctgaaacg tgtgctcctt gggcc                                1236
```

<210> SEQ ID NO 18
<211> LENGTH: 1332
<212> TYPE: DNA
<213> ORGANISM: Human

<400> SEQUENCE: 18

```
atgggcctcc acctccgccc ctaccgtgtg gggctgctcc cggatggcct cctgttcctc     60
ttgctgctgc taatgctgct cgcggaccca gcgctcccgg ccggacgtca ccccccagtg    120
gtgctggtcc ctggtgattt gggtaaccaa ctggaagcca agctggacaa gccgacagtg    180
gtgcactacc tctgctccaa gaagaccgaa agctacttca caatctggct gaacctggaa    240
ctgctgctgc ctgtcatcat tgactgctgg attgacaata tcaggctgga gtgcagtggc    300
gcaatctcgg ctcactacac ctctgcctcc aggctcaag cacttctcct gcctcagact     360
ccggataact gggattacag gctggtttac aacaaaacat ccagggccac ccagtttcct    420
gatggtgtgg atgtacgtgt ccctggcttt gggaagacct tctcactgga gttcctggac    480
cccagcaaaa gcagcgtggg ttcctatttc cacaccatgg tggagagcct tgtgggctgg    540
ggctacacac ggggtgagga tgtccgaggg gctccctatg actggcgccg agccccaaat    600
gaaaacgggc cctacttcct ggccctccgc gagatgatcg aggagatgta ccagctgtat    660
gggggccccg tggtgctggt tgcccacagt atgggcaaca tgtacacgct ctactttctg    720
cagcggcagc gcaggcctg gaaggacaag tatatccggg ccttcgtgtc actgggtgcg    780
ccctgggggg gcgtggccaa gaccctgcgc gtcctggctt caggagacaa caaccggatc    840
ccagtcatcg ggcccctgaa gatccgggag cagcagcggt cagctgtctc caccagctgg    900
ctgctgccct acaactacac atggtcacct gagaaggtgt tcgtgcagac cccacaatc    960 aactacacac tgcgggacta ccgcaagttc ttccaggaca tcggctttga agatggctgg   1020
ctcatgcggc aggacacaga agggctggtg aagccacga tgccacctgg cgtgcagctg    1080
cactgcctct atggtactgg cgtccccaca ccagactcct tctactatga gagcttccct    1140
gaccgtgacc ctaaaatctg ctttggtgac ggcgatggta ctgtgaactt gaagagtgcc    1200
ctgcagtgcc aggcctggca gagccgccag gagcaccaag tgttgctgca ggagctgcca    1260
ggcagcgagc acatcgagat gctggccaac gccaccaccc tggcctatct gaaacgtgtg   1320
ctccttgggc cc                                                       1332
```

<210> SEQ ID NO 19
<211> LENGTH: 1236
<212> TYPE: DNA
<213> ORGANISM: Murine

<400> SEQUENCE: 19

```
atggatcgcc atctctgcac ctgtcgcgag acccagctcc ggagtggcct cctgttacct     60
ctgtttctac taatgatgct ggcagacctg acgctcccgg cccaacgtca ccccccggtg    120
gtgctggtgc ctggtgattt gggtaaccag ttggaagcaa agctggataa gccaaaggtt    180
gtacactacc tttgctccaa gaagacggac agctacttca cactctggct gaatctggaa    240
```

-continued

```
ctgcttctgc ctgttatcat tgactgctgg attgacaata tcaggctggt ttacaacaga      300
acatctcggg ccacccagtt tcccgatggt gtggacgtgc gtgtccctgg ctttggggaa      360
acattttcta tggaattcct agaccccagc aagaggaatg tgggttccta tttctacact      420
atggtggaga gccttgtggg ctggggctac acacgggtg aagacgttcg aggtgctccc       480
tatgattggc ggcgagcccc aaatgaaaac gggccctact tcttggccct gcagagatg       540 atcgaggaga tgtaccagat gtatgggggc cccgtggtgc tggtcgccca gcatgggc       600 aacgtgtaca tgctctactt tctgcagcgg cagccacaag tctggaagga caaatatatc      660
catgccttcg tctcactggg ggcgccctgg gggggcgtgg ccaagacgct gcgtgtcctg      720
gcctcaggag acaacaatcg cattcccgtc attgggccac tgaagatccg ggaacagcag      780
cgatctgccg tctctaccag ctggctactg ccatacaacc acacttggtc acatgaaaag      840
gtatttgtat acacacccac gactaactac acgctccggg actatcaccg gttcttccgg      900
gacatcggtt tcgaagatgg ctggttcatg cggcaggaca cagaagggct ggttgaagcc      960
atgacgccac ccggggtgga gctgcactgc ttgtatggca ctggtgttcc cacgccaaac      1020
tctttctact acgagagctt tcctgatcgg gaccccaaaa tctgcttcgg cgatggtgac      1080
ggcacggtga acctggagag cgtcctgcag tgccaagcct ggcagagccg ccaagagcac      1140
agagtatcat tgcaggagct gccgggaagc gagcacattg agatgctagc caatgccacc      1200
accttggctt atctgaaacg tgtgcttctg gaacct      1236
```

<210> SEQ ID NO 20
<211> LENGTH: 90
<212> TYPE: DNA
<213> ORGANISM: Unknown
<220> FEATURE:
<223> OTHER INFORMATION: Unsure (DNA coding for signal peptide of SEQ ID NO: 9)

<400> SEQUENCE: 20

```
atgggcctcc acctccgccc ctaccgtgtg gggctgctcc cggatggcct cctgttcctc      60
ttgctgctgc taatgctgct cgcggaccca                                       90
```

<210> SEQ ID NO 21
<211> LENGTH: 99
<212> TYPE: DNA
<213> ORGANISM: Unknown
<220> FEATURE:
<223> OTHER INFORMATION: Unsure (DNA coding for signal peptide of SEQ ID NO: 10)

<400> SEQUENCE: 21

```
atgggcctcc acctccgccc ctaccgtgtg gggctgctcc cggatggcct cctgttcctc      60
ttgctgctgc taatgctgct cgcggaccca gcgctcccg                             99
```

<210> SEQ ID NO 22
<211> LENGTH: 99
<212> TYPE: DNA
<213> ORGANISM: Unknown
<220> FEATURE:
<223> OTHER INFORMATION: Unsure (DNA coding for signal peptide of SEQ ID NO: 11)

<400> SEQUENCE: 22

```
atggatcgcc atctctgcac ctgtcgcgag acccagctcc ggagtggcct cctgttacct      60
ctgtttctac taatgatgct ggcagacctg acgctcccg                             99
```

<210> SEQ ID NO 23
<211> LENGTH: 392
<212> TYPE: DNA
<213> ORGANISM: Human

<400> SEQUENCE: 23

| | | | | | |
|---|---|---|---|---|---|
| acacgctcta | ctttctgcag | cggcagccgc | agcctggtaa | ggacaagtat | atccgggcct | 60 |
| tcgtgtcact | gggtgcgccc | tggggggcg | tggccaagac | cctgcgcgtc | ctggcttcag | 120 |
| gagacaacaa | ccggatccca | gtcatcgggc | ccctgaagat | ccgggagcag | cagcggtcag | 180 |
| ctgtctccac | cagctggctg | ctgccctaca | actacacatg | gtcacctgag | aaggtgttcg | 240 |
| tgcagacacc | cacaatcaac | tacacactgc | gggactaccg | caagttcttc | caggacatcg | 300 |
| gctttgaaga | tggctggctc | atgcggcagg | acacagaagg | gctagtggaa | gccacgatgc | 360 |
| cacctggcgt | gcagctgcac | tgcctctatg | gt | | | 392 |

<210> SEQ ID NO 24
<211> LENGTH: 23
<212> TYPE: DNA
<213> ORGANISM: Unknown
<220> FEATURE:
<223> OTHER INFORMATION: Unsure (synthetic primer)

<400> SEQUENCE: 24
gctgctgccc tacaactaca cat                                              23

<210> SEQ ID NO 25
<211> LENGTH: 19
<212> TYPE: DNA
<213> ORGANISM: Unknown
<220> FEATURE:
<223> OTHER INFORMATION: Unsure (synthetic primer)

<400> SEQUENCE: 25
tatccgggcc ttcgtgtca                                                   19

<210> SEQ ID NO 26
<211> LENGTH: 28
<212> TYPE: DNA
<213> ORGANISM: Unknown
<220> FEATURE:
<223> OTHER INFORMATION: Unsure (synthetic primer)

<400> SEQUENCE: 26
tcaaagccga tgtcctggaa gaacttgc                                         28

<210> SEQ ID NO 27
<211> LENGTH: 24
<212> TYPE: DNA
<213> ORGANISM: Unknown
<220> FEATURE:
<223> OTHER INFORMATION: Unsure (synthetic primer)

<400> SEQUENCE: 27
gtggtgctgg tccctggtga tttg                                             24

<210> SEQ ID NO 28
<211> LENGTH: 22
<212> TYPE: DNA
<213> ORGANISM: Unknown
<220> FEATURE:
<223> OTHER INFORMATION: Unsure (synthetic primer)

<400> SEQUENCE: 28

```
ggtggccctg gatgttttgt tg                                            22
```

<210> SEQ ID NO 29
<211> LENGTH: 198
<212> TYPE: DNA
<213> ORGANISM: Murine

<400> SEQUENCE: 29

```
gtggtgctgg tccctggtga tttgggtaac cagttggaag caaagctgga taagccaaag   60
gttgtacact acctttgctc caagaagacg gacagctact tcacactctg gctgaatctg  120
gaactgcttc tgcctgttat cattgactgc tggattgaca atatcaggct ggtttacaac  180
aaaacatcca gggccacc                                                198
```

<210> SEQ ID NO 30
<211> LENGTH: 25
<212> TYPE: DNA
<213> ORGANISM: Unknown
<220> FEATURE:
<223> OTHER INFORMATION: Unsure (synthetic primer)

<400> SEQUENCE: 30

```
ggttgtacac tacctttgct ccaag                                         25
```

<210> SEQ ID NO 31
<211> LENGTH: 21
<212> TYPE: DNA
<213> ORGANISM: Unknown
<220> FEATURE:
<223> OTHER INFORMATION: Unsure (synthetic primer)

<400> SEQUENCE: 31

```
ggtaaccagt tggaagcaaa g                                             21
```

<210> SEQ ID NO 32
<211> LENGTH: 21
<212> TYPE: DNA
<213> ORGANISM: Unknown
<220> FEATURE:
<223> OTHER INFORMATION: Unsure (synthetic primer)

<400> SEQUENCE: 32

```
atccagcagt caatgataac a                                             21
```

<210> SEQ ID NO 33
<211> LENGTH: 22
<212> TYPE: DNA
<213> ORGANISM: Unknown
<220> FEATURE:
<223> OTHER INFORMATION: Unsure

<400> SEQUENCE: 33

```
gtaatacgac tcactatagg gc                                            22
```

<210> SEQ ID NO 34
<211> LENGTH: 19
<212> TYPE: DNA
<213> ORGANISM: Unknown
<220> FEATURE:
<223> OTHER INFORMATION: Unsure (synthetic primer)

<400> SEQUENCE: 34

```
actatagggc acgcgtggt                                                19
```

<210> SEQ ID NO 35
<211> LENGTH: 48
<212> TYPE: DNA
<213> ORGANISM: Unknown
<220> FEATURE:
<223> OTHER INFORMATION: Unsure (adapter used for cloning genomic DNA)

<400> SEQUENCE: 35
gtaatacgac tcactatagg gcacgcgtgg tcgacggccc gggctggt            48

<210> SEQ ID NO 36
<211> LENGTH: 26
<212> TYPE: DNA
<213> ORGANISM: Unknown
<220> FEATURE:
<223> OTHER INFORMATION: Unsure (synthetic primer)

<400> SEQUENCE: 36
atccgggagc agccccacac ggtagg                                    26

<210> SEQ ID NO 37
<211> LENGTH: 24
<212> TYPE: DNA
<213> ORGANISM: Unknown
<220> FEATURE:
<223> OTHER INFORMATION: Unsure (synthetic primer)

<400> SEQUENCE: 37
ggtgtacgac ggtcgccgca ggtc                                      24

<210> SEQ ID NO 38
<211> LENGTH: 2867
<212> TYPE: DNA
<213> ORGANISM: Unknown
<220> FEATURE:
<223> OTHER INFORMATION: Unsure (5' flanking promoter sequence of
      genomic DNA)

<400> SEQUENCE: 38
actatagggc acgcgtggtc gacggcccgg gctggtatta aaaaaaaaaa tcagggccgg    60
gtgtgatggc tcatacctgt aatcccagca ctttgggaga cctaggtggg tggatcacct   120
gaggtcagga gttcaagacc agcctggcca acatggcgaa atcccgtctc tactaaaaaa   180
tacaaaaatc agctgggcgt ggtggcgggt gcctgtaatc ccagctattc aggaggctga   240
ggcaggagaa tcgcttgaac ccaggaggca gaggttgcag tgagccggga tcacgccact   300
gctctccagc ctgggtgaca gagcaaaact ctgtctcaaa aaaaaaaaaa aggtgtcagc   360
ctggcatgtg gagaacgacc cacaggaacg agggcgtgca ttgggacatc agtgacgagg   420
ctgttgtggg aatagggtag tgtggtttgg ggagtgtaga gctggcaagc ccttatgacc   480
acctgagttg tggttctgag aagcatggaa gcatccagag ctcaggatga tgccaagtct   540
gcagcctggg ggatcaggtg gatggcagag tcattgtgaa aagggaggac cctcactttc   600
tgacccttct ccacagtgcc agcatgggtc attgctgacc aggccttgcc atcctgcccc   660
taatggctgt ggttcctaac acatgcaggg cctgtggggt tgaagcacca aggaacccct   720
cttgaggaca gggctaccct tccaggggcc catggtcacc ggatgctgct gggccggcaa   780
gacatttaga ctgtggccag agtccaaggt ggcccagcac ctcttgatcc ttctcttcct   840
ccacataacc tttgactgga cttctgcccg tccctaggcc tgcagaagag tctctggtct   900
cccacgctgg gttttcacca gatgggtctt cactgatctt ctgttgggtc acgggtgaag   960

-continued

```
gtgggggagg cagggctttt gggagtggga gttctgagcc agggccttag cgggagatgg    1020
ctggacctta agagagggtg gggctggtca cagtggcaca catctgtaat ctcagcactt    1080
tgggaggctg aggcaggtgg atcacttaag gccaggagtt caagactggc ctgggcaaca    1140
tagtgagacc ccaactctac aaaaaaaaaa actagctgag cttggaggtg tacacttgta    1200
gtcccagcta ctcaggaggc tgaggtggga aggattgctt gagcctgaga ggtcaaggat    1260
gcagtgagcc gtgattgcgc tactgcactt gggtgacaga gagacccttt ctcaaaaaaa    1320
aaaaaaaaaa aaaggaaaga aaagaaaaag gggccgggca cagtagctca cgcctgtaat    1380
cccagcactt tgggaggccg aggcaggtgg atcacctgag gttgcgagtt caagaccagc    1440
ctgactaaca tggagaaacc ccgtctctac taaaaataca aaattagcca gggtggtggc    1500
gcatgcctgc aatcccagct actcgggagg ctgaggcagg agaattgctt gaatccagga    1560
gacggaggtt acgtgagcc aagattgcac cattgcactc cagcctgggc aacaagagcg    1620
aaactctgtc tcaaaaaaaa aaagaaaaa gaaaagaaa aagaaagag ggagggtggt      1680 ggtagcccag tcaccaacat gtttcactat aagaactcga aagggcagg caagatagt      1740 ggcttcatag ccaggtcagc tgcttaccaa gaagaaggaa ggaaggggca ggacaaattt    1800
cttgggacca ggtgggatga ccagggtgca gctgccccctt cgaagggtg ggtgtgtgga    1860 ggatcaagac ctctatttcc caaatactct cgtccctcta tcccacagtg acctatggtg    1920
ctggcatata accagctgtc aggtctttgc ccactctgtt cgcccctgct tcctggcgca    1980
gggagtccat gtcctctctg gttccccagg tttgcgagag tggaggggga ccacgagctc    2040
ccgatgcctc tcctgctctg caggggaact tgcagatggc ccatgcgca gggtcgagac     2100 tcaagcccac tcccaacccc gcgcccgaac tgcccggact ggcggggtga cgctgcactc    2160
tgcgccccta aaacgaacag attaacccct ctcctgggaa ctgaacatgc tgacctggcc    2220
tctcccggtt cccccccgcat ctgtaacccc ggggcagagt tacaggggct gactggccgc   2280
acccaggtgc cctcggggca gggtgtgcta agaattggtg tgggggctgc acaaaggtcc    2340
tggtcagctc ctggtcacct gaggcccaag aactgtccgg gactcacttc ctctcttctt    2400
gctttaaccg gggtcgctca gcagcggcca gcgctgcacc ccttatcctc tcccggtctt    2460
gtccgttcca gatcctccag gtcagggggt cgccaagtga gagctgcgca gcgtggattt    2520
cgggtaccca gggctgggcg gggtacagca gcggcgagct gggttcccgg gtgggcgact    2580
gacagcccgg agccaggcga tacctcgatc catcgatgcg ctcggcgctc agcgtggtcc    2640
aggaagcagg gggttgggca agggcgggc ggcgacctcc gactgggagg ggcgtatatg    2700
gcggcgagtc cctattggcc agccatttgc gggaggcggg ccctgattgg ccgggggat    2760 gcggggatg cgggcggcgg ggttaagcgc gtcgccaccg cccccgccta ggcgagagcc     2820
cagagagctg aacctgcatc ccggacctgc ggcgaccgtc gtacacc                  2867
```

<210> SEQ ID NO 39
<211> LENGTH: 20
<212> TYPE: PRT
<213> ORGANISM: Unknown
<220> FEATURE:
<223> OTHER INFORMATION: Unsure (chemically synthesized partial peptide of human LCAT-like protein)

<400> SEQUENCE: 39

Cys Glu Asp Val Arg Gly Ala Pro Tyr Asp Trp Arg Arg Ala Pro
1               5                   10                  15

Asn Glu Asn Gly Pro
            20

-continued

```
<210> SEQ ID NO 40
<211> LENGTH: 19
<212> TYPE: PRT
<213> ORGANISM: Unknown
<220> FEATURE:
<223> OTHER INFORMATION: Unsure (chemically synthesized partial peptide
      of human LCAT-like protein)
<400> SEQUENCE: 40

Pro Val Ile Gly Pro Leu Lys Ile Arg Glu Gln Gln Arg Ser Ala
1               5                   10                  15

Val Ser Thr Cys

<210> SEQ ID NO 41
<211> LENGTH: 63
<212> TYPE: DNA
<213> ORGANISM: Unknown
<220> FEATURE:
<223> OTHER INFORMATION: Unsure (primer for synthesizing FLAG peptide)

<400> SEQUENCE: 41
ccgctcgagt cacttgtcat cgtcgtcgtc cttgtagtcg ggcccaagga gcacacgttt cag   63

<210> SEQ ID NO 42
<211> LENGTH: 31
<212> TYPE: DNA
<213> ORGANISM: Unknown
<220> FEATURE:
<223> OTHER INFORMATION: Unsure (primer for synthesizing FLAG peptide)

<400> SEQUENCE: 42
ggagacaacc aaccggatcc cagtcatcgg g                                     31

<210> SEQ ID NO 43
<211> LENGTH: 10
<212> TYPE: PRT
<213> ORGANISM: Unknown
<220> FEATURE:
<223> OTHER INFORMATION: Unsure (partial peptide)

<400> SEQUENCE: 43

Ala Gly Arg His Pro Pro Val Val Leu Val
1               5                   10
```

US 6,498,019 B1

LECITHIN-CHOLESTEROL ACYLTRANSFERASE PROTEIN

This Application is the National Stage of International Application Serial No. PCT/JP98/01643, filed Apr. 9, 1998.

TECHNICAL FIELD

The present invention relates to a novel protein having a lecithin-cholesterol acyltransferase-like activity etc. and a DNA coding for the protein.

BACKGROUND ART

Cholesterol is an important lipid constituting the animal cell membrane and defining its character. Moreover, it is a precursor of steroid hormones, thus being a substance essential to animal life. However, due to the recent changes in dietary habit and ecology, arteriosclerosis and other adult diseases arising from pathological intracellular accumulation of cholesterol are now presenting a serious problem so that elucidation of the mechanisms of cholesterol metabolism in the body is being awaited.

In the efflux of cholesterol from the peripheral cells, high density lipoprotein (hereinafter sometimes referred to briefly as HDL) is suspected to play a cardinal role and this assumption has been supported by the epidemiologic finding of an inverse correlation between risk for coronary artery disease and plasma HDL levels and the experimental finding that HDL in culture medium stimulates cholesterol efflux from cells and decreases the intracellular concentration of cholesterol (Journal of Lipid Research, 37, 2473, 1996). In the reverse cholesterol transport system, lecithin-cholesterol acyltransferase (hereinafter sometimes referred to briefly as LCAT) is involved to a significant extent.

LCAT transfers the β-acyl group (fatty acid) of lecithin (phosphatidylcholine) to the 3β-OH group of cholesterol, so that it consumes the equivalent moles of lecithin and unesterified cholesterol and produces the equivalent moles of cholesteryl ester and lysolecithin (Journal of Lipid Research, 9, 155, 1968). In the circulation, most of LCAT exists in HDL to show activity and a portion of the cholesteryl ester produced in the HDL is taken up and metabolized in the liver, while another portion of the ester migrates into the nonpolar core of the HDL particle to give rise to a mature HDL rich in cholesteryl esters. Owing to the concentration gradient resulting from the consumption of unesterified cholesterol in HDL, the HDL continuously absorbs cholesterol from the other cell membranes. In this manner, LCAT together with HDL is in charge of the reverse cholesterol transport from peripheral tissues to the liver, thus contributing to the anti-atherosclerotic action of HDL (Biochimica et Biophysica Acta, 1084, 205, 1991).

In familial LCAT deficiency which is an inheritable disease, the reverse cholesterol transport system is lacking so that characteristic tissue damages occur from deposits of cholesterol, leading to coroneal opacity, hemolytic anemia associated with a morphological abnormality of erythrocytes, and proteinuria and renal failure due to kidney impairment (Lancet, 388, 778, 1991). In addition to gene abnormalities, various illnesses involving plasma lipid abnormalities cause changes in LCAT activity. For example, LCAT activity is reportedly elevated by hypercalorism or in obesity and hypertriglyceridemia (Clinical Science, 38, 593, 1970) and decreased in malnutrition, abetalipoproteinemia, and Tangier disease.

LCAT is a 416-residue polypeptide synthesized in the liver, and exists as a glycoprotein with a molecular mass of 59–68 KDa (Journal of Biological Chemistry, 254, 7456, 1979). In the blood, most of LCAT exists in HDL and in the expression of its activity, Apo AI, the principal apoprotein of HDL, acts as the cofactor to stimulate LCAT activity (FEBS Letters, 15, 355, 1971). There exist a variety of mutant LCAT genes corresponding to the variation in enzyme defect and clinical picture in various cases of familial LCAT activity deficiency, and they are discharging significant functions in the metabolism of plasma lipoproteins.

So far, only one kind of LCAT has been reported and the existence of any analogous protein having similar activity has not been predicted.

Meanwhile, in arteriosclerosis, thrombus formation, and post-PTCA restenosis, abnormality of vascular tonus, enhancement of inflammatory reactions, and abnormality of the coagulation-fibrinolysis system, which stem from endothelial cell impairment, occur to cause a remodeling of the blood vessel with the proliferation and transformation of vascular smooth muscle cells as a cardinal pathological picture. The changes on the molecular level which occur in the course of formation of vascular lesions are now being understood in terms of a group of transcription factors controlling the expression of individual genes (Kurabayashi et al., Modern Medicine, 52, 2340, 1997). In such a specifically expressed gene, there is a promoter (enhancer-repressor) sequence which functions only ad hoc and this promoter domain controls the transcription levels of the mRNA encoding the protein.

Some of those promoters are known to be hormone-dependent or growth factor-dependent, and by utilizing them, several drug screening systems and transgenic animals have already been created and actually the systems used in the screening for drugs and the animals used in the analysis of vital functions.

The present invention has for its object to provide a novel protein having LCAT and other activities, a precursor protein thereof, a partial peptide, a salt of either of them, a signal peptide, a DNA coding for said protein, precursor protein, partial peptide or signal peptide, a recombinant vector, a transformant, a method of producing said protein, a pharmaceutical composition comprising said protein or DNA, an antibody against said protein, a screening method/screening kit for a compound promoting or inhibiting the LCAT activity of said protein, a compound obtained by using said screening method, a pharmaceutical composition comprising said compound, a promoter for a novel protein having LCAT and other activities, a screening method/screening kit for a compound promoting or inhibiting the promoter activity, a compound obtained by using the screening method mentioned just above, and a pharmaceutical composition comprising the compound.

The inventors of the present invention did intensive research to accomplish the above-mentioned objects and succeeded in cloning a cDNA having a novel nucleotide sequence from each of human heart-, human kidney-, and mouse kidney-derived cDNA libraries, and discovered that the protein encoded by those cDNA clones is a lecithin-cholesterol acyltransferase-like protein (hereinafter sometimes referred to as the LCAT-like protein). The inventors further cloned the genomic DNA of said LCAT-like protein and by a promoter activity assay, found a promoter for said LCAT-like protein.

DISCLOSURE OF INVENTION

The present invention, provides:
(1) a protein comprising an amino acid sequence represented by SEQ ID NO:1, SEQ ID NO:2 or SEQ ID NO:3 or a substantial equivalent thereto, a precursor protein thereof or a salt thereof, (2) a protein or precursor protein according to the above item (1), which comprises an amino acid sequence represented by any one of SEQ ID NO:4 to SEQ ID NO:8, (3) a protein or precursor protein according to the above item (1), which possesses lecithin-cholesterol acyltransferase-like activity, (4) a partial peptide of the protein according to the above item (1), or a salt thereof, (5) a signal peptide comprising an amino acid sequence represented by SEQ ID NO:9, SEQ ID NO:10 or SEQ ID NO:11, or a substantial equivalent thereto, (6) a DNA which comprises a DNA having a nucleotide sequence coding for the protein or precursor protein according to the above item (1), (7) a DNA according to the above item (6), which comprises a nucleotide sequence represented by any one of SEQ ID NO:12 to SEQ ID NO:19, (8) a DNA which comprises a DNA having a nucleotide sequence coding for the signal peptide according to the above item (5), (9) a DNA according to the above item (8), which comprises a nucleotide sequence represented by SEQ ID NO:20 to SEQ ID NO:22,

(10) a recombinant vector comprising the DNA according to the above item (6),

(11) a transformant which is transformed by the recombinant vector according to the above item (10),

(12) a method for producing the protein or the precursor protein according to the above item (1) or the salt thereof, which comprises cultivating the transformant according to the above item (11) to produce and accumulate the protein or the precursor protein according to the above item (1), and collecting the same,

(13) a pharmaceutical composition which comprises the protein or the precursor protein or a salt thereof according to the above item (1),

(14) a pharmaceutical composition which comprises the DNA according to the above item (6),

(15) a pharmaceutical composition according to the above item (13) or the above item (14), which is an agent for treating or preventing arteriosclerosis, atherosclerosis hyperlipidemia, obesity, inflammatory diseases, senescence, diseases of brain or renal disorder,

(16) an antibody against (i) the protein or the precursor protein according to the above item (1), (ii) the partial peptide according to the above item (4), or (iii) a salt thereof,

(17) a method for screening for a compound which promotes or inhibits a lecithin-cholesterol acyltransferase-like activity of (i) the protein according to the above item (1), (ii) the partial peptide according to the above item (4), or (iii) a salt thereof, which comprises using (i) the protein according to the above item (1), (ii) the partial peptide according to the above item (4), or (iii) a salt thereof,

(18) a kit for screening for a compound which promotes or inhibits a lecithin-cholesterol acyltransferase-like activity of(i) the protein according to the above item (1), (ii) the partial peptide according to the above item (4), or (iii) a salt thereof, which comprises using (i) the protein according to the above item (1), (ii) the partial peptide according to the above item (4), or (iii) a salt thereof,

(19) a compound which promotes or inhibits a lecithin-cholesterol acyltransferase-like activity of (i) the protein according to the above item (1), (ii) the partial peptide according to the above item (4), or (iii) a salt thereof, which is obtained by using the screening method according to the above item (17) or the screening kit according to the above item (18),

(20) a pharmaceutical composition which comprises a compound which promotes or inhibits a lecithin-cholesterol acyltransferase-like activity of (i) the protein according to the above item (1), (ii) the partial peptide according to the above item (4), or (iii) a salt thereof, which is obtained by using the screening method according to the above item (17) or the screening kit according to the above item (18),

(21) a DNA which comprises a promoter DNA having a nucleotide sequence represented by SEQ ID NO:38 or a substantial equivalent thereto or its partial DNA having a promoter activity, and

(22) a method for screening for a compound or a salt thereof which promotes or inhibits the promoter activity of the DNA according to the above item (21). The present invention, furthermore, provides:

(23) a protein or the precursor according to the above item (1), wherein the amino acid sequence is an amino acid sequence having an identity of not less than about 50% (preferably not less than about 60%, more preferably not less than about 70%, still more preferably not less than about 80%, still more preferably not less than about 90%, most preferably not less than about 95%) to the total amino acid sequence represented by SEQ ID NO:1, SEQ ID NO:2 or SEQ ID NO:3 or a substantial equivalent thereto,

(24) a protein or the precursor according to the above item (1), which comprises (i) an amino acid sequence wherein one or more amino acid residues (for example about 1 to 30 amino acid residues) are deleted from the amino acid sequence represented by SEQ ID NO:1, SEQ ID NO:2 or SEQ ID NO:3, or a substantial equivalent thereto, (ii) an amino acid sequence wherein one or more amino acid residues (for example about 1 to 30 amino acid residues) are added to the amino acid sequence represented by SEQ ID NO:1, SEQ ID NO:2 or SEQ ID NO:3, or a substantial equivalent thereto, (iii) an amino acid sequence wherein one or more amino acid residues (for example 1 to 30 amino acid residues). are inserted into the amino acid sequence represented by SEQ ID NO:1, SEQ ID NO:2 or SEQ ID NO:3, or a substantial equivalent thereto, (iv) an amino acid sequence wherein one or more other amino acid residues in the amino acid sequence represented by SEQ ID NO:1, SEQ ID NO:2 or SEQ ID NO:3 or a substantial equivalent thereto, are substituted with 1 or more amino acid residues (for example about 1 to 30), or (vi) combinations thereof,

(25) a peptide according to the above item (4), which comprises at least one amino acid sequence selected from the group consisting of amino acid sequences of the 3rd–25th residues, 27th–36th residues, 43rd–66th residues, 68th–86th residues, 92nd–98th residues, 107th–153rd residues, 155th–168th residues, 172nd–180th residues, 189th–240th residues, 256th–262nd residues, 268th–275th residues, 277th–287th residues, 295th–306th residues 308th–332nd residues, 336th–347th residues and/or 351st–377th residues of the amino acid sequence represented by SEQ ID NO:1,

(26) an isolated DNA comprising a DNA having a nucleotide sequence which hybridizes under highstringent condition to a nucleotide sequence represented by any one of SEQ ID NO:12 to SEQ ID NO:19,

(27) a recombinant vector comprising the DNA according to the above item (26),

(28) a transformant which is transformed with the recombinant vector according to the above item (27),

(29) a process for producing a protein, a precursor thereto, or a salt thereof which comprises culturing the transformant according to the above item (28) under conditions suitable to express and accumulate the protein, a precursor thereto, or a salt thereof which is encoded by the DNA according to the above item (26) or a salt thereof and collect the same,

(30) a protein, a precursor thereto encoded by the DNA according to the above item (26) which is produced by the process according to the above item (29) or a salt thereof,

(31) a method according to the above item (17), which comprises measuring and comparing a lecithin-cholesterol acyltransferase-like activity, in cases that (i) the protein according to the above item (1), the partial peptide according to the above item (4), or a salt thereof is contacted with a lecithin and a non-esterified cholesterol, and (ii) the protein according to the above item (1), the partial peptide according to the above item (4),or a salt thereof is contacted with a lecithin, a non-esterified cholesterol and a test compound,

(32) a pharmaceutical composition which comprises a compound or a salt thereof having a promoting activity of a lecithin-cholesterol acyltransferase-like activity of the protein according to the above item (1), the partial peptide according to the above item (4) or a salt thereof, obtained by the screening method according to the above item (17) or the screening kit according to the above item (18),

(33) a pharmaceutical composition according to the above item (32), which is an agent for treating or preventing arteriosclerosis, atherosclerosis, hyperlipidemia, obesity, atherosclerosis senescence, diseases of brain or renal disorder,

(34) a pharmaceutical composition according to the above item (32), which is an agent for treating or preventing hypercalorism, obesity or hypertriglyceridemia,

(35) a pharmaceutical composition which comprises a compound or a salt thereof having a inhibiting activity of a lecithin-cholesterol acyltransferase-like activity of the protein according to the above item (1), the partial peptide according to the above item (4) or a salt thereof, obtained by the screening method according to the above item (17), or the screening kit according to the above item (18),

(36) a pharmaceutical composition according to the above item (35), which is an agent for treating or preventing malnutrition, abetalipoproteinemia, inflammatory diseases or Tangier disease,

(37) a method of quantitative determination of the protein according to the above item (1), the partial peptide according to the above item (4) or a salt thereof in a test liquid sample, which comprises (a) competitively reacting the test liquid sample and a labeled protein according to the above item (1) partial peptide according to the above item (4) or a salt thereof with the antibody according to the above item (16), and (b) measuring the ratio of the labeled protein according to the above item (1), partial peptide according to the above item (4) or a salt thereof which binds to the antibody,

(38) a method of quantitative determination of the protein according to the above item (1), the partial peptide according to the above item (4) or a salt thereof in a test liquid sample, which comprises (a) reacting the test liquid sample with the antibody according to the above item (16) immobilized on an insoluble carrier and another antibody which is labeled according to the above item (16) simultaneously or continuously, and (b) measuring the activity of the labeling agent on the insoluble carrier,

(39) a pharmaceutical composition which comprises the antibody according to the above item (16),

(40) a pharmaceutical composition according to the above item (39), which is an agent for treating or preventing malnutrition, abetalipoproteinemia inflammatory diseases or Tangier disease,

(41) an antisense DNA having a nucleotide sequence complementary or substantially complementary to the DNA according to the above item (4) or the above item (26), and capable of suppressing expression of the same DNA,

(42) an antisense DNA according to the above item (41), wherein the nucleotide sequence substantially complementary to the DNA according to the above item (4) or (26) is a nucleotide sequence having an identity of not less than about 70% (preferably not less than about 90%, more preferably not less than about 95%) to the total nucleotide sequence or partial nucleotide sequence of the nucleotide sequence complementary to the DNA according to the above item (4) or (26),

(43) a pharmaceutical composition which comprises the antisense DNA according to the above item (41), and

(44) an pharmaceutical composition according to the above item (43), which is an agent for treating or preventing malnutrition, abetalipoproteinemia inflammatory diseases or Tangier disease.

The protein (the protein of the invention) having an amino acid sequence identical or substantially equivalent thereto identical to the amino acid sequence represented by SEQ ID NO:1, SEQ ID NO:2, or SEQ ID NO:3 may be any of the proteins derived from various tissues of man and other warm-blooded animals (e.g. guinea pig, rat, mouse, fowl, rabbit, swine, sheep, bovine, monkey, etc.). Among such tissues are cells (e.g. hepatocytes, splenocytes, nerve cells, glia cells, β cells of pancreas, myelocytes, mesangial cells, Langerhan' cells, epidermic cells, epithelial cells, endothelial cells, fibroblasts, fibrocytes, myocites, adipocytes, immune cells (e.g. macrophages, T-cells, B cells, natural killer cells, mastocytes, neutrophils, basophils, eosinophils, monocytes), megarocytes, synovial cells, chondrocytes, osteocytes, osteoblasts, osteoclasts, mammary gland cells, hepatocytes, interstitial cells, the corresponding precursor cells, stem cells, cancer cells, etc.), all tissues in which such cells exist, for example the brain, various parts of the brain (e.g. olefactory bulb, amygdaloid body, basal ganglia, hippocampus, thalamus, hypothalamus, cerebral cortex, medula oblongata, cerebellum), spinal cord, pituitary gland, stomach, pancreas, kidney, liver, gonad, thyroid, gallbladder, bone marrow, adrenal, skin, muscle, lung, bowels (e.g. large intestine and small intestine), blood vessel, heart, thymus, spleen, submandibular gland, peripheral blood, prostate, testis, ovary, placenta, uterus, bone, joint, skeletal muscle, etc., and blood series cells and the corresponding cultured cell lines (e.g. MEL, Ml, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.). The protein mentioned above may also be a synthetic protein.

The amino acid sequence represented by SEQ ID NO:2 is an amino acid sequence in which 32 amino acid residues of the 64th (Glu) to 95th (Leu) amino acid residues of SEQ ID NO:2 is inserted between the 63rd (Leu) and 64th (Val) amino acids of SEQ ID NO:1.

Examples of the amino acid sequence which is substantially equivalent to the amino acid sequence represented by SEQ ID NO:1, SEQ ID NO:2 or SEQ ID NO:3 are an amino acid sequence which is not less than about 50%, preferably not less than about 60%, more preferably not less than about 70%, still more preferably not less than about 80%, still more preferably not less than about 90%, and most preferably not less than about 95% identity to the amino acid sequence represented by SEQ ID NO:1, SEQ ID NO:2 or SEQ ID NO:3, and so on.

And, as an amino acid sequence substantially equivalent to the amino acid sequence represented by SEQ ID NO:1, SEQ ID NO:2 or SEQ ID NO:3, an amino acid sequence containing the amino acid sequence of the 3rd–25th residues, 27th–36th residues, 43rd–66th residues, 68th–86th residues, 92nd–98th residues, 107th–153rd residues, 155th–168th residues, 172nd–180th residues, 189th–240th residues, 256th–262nd residues, 268th–275th residues, 277th–287th residues, 295th–306th residues, 308th–332nd residues, 336th–347th residues, and/or 351st–377th residues, respectively, of the amino acid sequence represented by SEQ ID NO:1, and so on are also preferred.

Examples of the protein of the present invention which comprises an amino acid sequence substantially equivalent to the amino acid sequence represented by SEQ ID NO:1, SEQ ID NO:2 or SEQ ID NO:3 are a protein having an amino acid sequence substantially equivalent to the amino acid sequence represented by SEQ ID NO:1, SEQ ID NO:2 or SEQ ID NO:3 and having a qualitatively equivalent activity to the protein having the amino acid sequence represented by SEQ ID NO:1, SEQ ID NO:2 or SEQ ID NO:3.

Examples of the lecithin:cholesterol acyltransferase-like activity are lecithin:cholesterol acyltransferase activity, phospholipase activity, lysophosphatidylcholine-to-phosphatidylcholine esterification activity, phospholipid:cholesterol acyttransferase activity, lysophospholipase activity, PAF hydrolysis/transesterification activity, fatty acid ester hydrolyzing activity, phospholipid oxide hydrolyzing and cholesterol oxide esterification activity, high-density lipoprotein (HDL) metabolism regulation activity, and lipase activity.

The term "qualitatively equivalent activity" is used herein to mean substantial equivalence in qualitative terms such as a lecithin-cholesterol acyltransferase (LCAT)-like activity, etc. Therefore, the degree of equivalence may range, for example, from about 0.1 to about 100 times (preferably about 0.5 to 10, more preferably 0.5 to 2 times). However, differences in quantitative terms such as the potency of activity and the molecular mass of protein are immaterial.

Activities such as a LCAT-like activity may be measured by a per se known method or its analogue method. For example, the activities may be measured by the method for screening as mentioned below.

And, the protein of the present invention includes the so called muteins, for example, proteins comprising (1) an amino acid sequence wherein one or more amino acid residues (preferably 1 to 30, more preferably about 1 to 10, and still more preferably a few (1 to 5) amino acid residues) are deleted from the amino acid sequence represented by SEQ ID NO:1, SEQ ID NO:2 or SEQ ID NO:3, (2) an amino acid sequence wherein one or more amino acid residues (preferably about 1 to 30, more preferably about 1 to 10, and still more preferably a few (1 to 5) amino acid residues) are added to the amino acid sequence represented by SEQ ID NO:1, SEQ ID NO:2 or SEQ ID NO:3, (3) an amino acid sequence wherein one or more amino acid residues (preferably 1 to 30, more preferably about 1 to 10, and still more preferably a few (1 to 5) amino acid residues) are inserted into the amino acid sequence represented by SEQ ID NO:1, SEQ ID NO:2 or SEQ ID NO:3, (4) an amino acid sequence wherein one or more other amino acid residues in the amino acid sequence represented by SEQ ID NO:1, SEQ ID NO:2 or SEQ ID NO:3 are substituted with 1 or more amino acid residues (preferably about 1 to 30, more preferably about 1 to 10, and still more preferably a few (1 to 5) amino acid residues), or (5) combinations thereof.

In the above-mentioned deletion, substitution, or insertion, examples of the positions of deletion, substitution or insertion are not so critical but are preferably positions other than the 3rd–25th residues, 27th–36th residues, 43rd–66th residues, 68th–86th residues, 92nd–98th residues, 107th–153rd residues, 155th–168th residues, 172nd–180th residues, 189th–240th residues, 256th–262nd residues, 268th–275th residues, 277th–287th residues, 295th–306th residues, 308th–332nd residues, 336th–347th residues or 351st–377th residues of the amino acid sequence represented by SEQ ID NO:1, and are not so critical but are preferably positions other than the corresponding position of SEQ ID NO:2.

In the above-mentioned deletion, substitution, or insertion, another example of the positions of deletion, substitution, or insertion are not so critical but are preferably positions other than (1) the 163rd(Ala)–167th(Gly) residues of the amino acid sequence represented by SEQ ID NO:1, (2) the 195th(Ala)–199th(Gly) residues of the amino acid sequence represented by SEQ ID NO:2, (3) the 96th(Val)–127th(Asp) residues of the amino acid sequence represented by SEQ ID NO:2, (4) the 163rd(Ala)–167th(Gly) residues of the amino acid sequence represented by SEQ ID NO:3, etc. The 163rd(Ala)–167th(Gly) residues of the amino acid sequence represented by SEQ ID NO:1 is a central active amino acid residues of the protein of the present invention.

Moreover, in the above-mentioned deletion or substitution, example of the positions of deletion or substitution are not so critical but are preferably positions of the 2nd, 26th, 37th, 42nd, 67th, 87th, 91st, 99th–100th, 106th, 154th, 169th, 171st, 181st, 188th, 241st, 245th, 251st, 255th, 263rd–264th, 267th, 276th, 288th–289th, 294th, 307th, 333rd, 335th, 348th, 350th or 378th of the amino acid sequence represented by SEQ ID NO:1 or SEQ ID NO:3, or the corresponding position of SEQ ID NO:2.

On the other hand, in the above-mentioned addition, example of the positions of addition are not so critical but are (1) the amino acid sequence represented by SEQ ID NO:4, wherein three amino acids are added to the N-terminal amino acid sequence represented by SEQ ID NO:1, or (2) the amino acid sequence represented by SEQ ID NO: 5, wherein three amino acids are added to the N-terminal amino acid sequence represented by SEQ ID NO:2, etc.

Accordingly, the protein of the present invention may include a protein having an amino acid sequence represented by SEQ ID NO:4 or SEQ ID NO:5, or substantially equivalent thereof. In this case, the term "substantially equivalent" means the same as mentioned above, The amino acid sequence represented by SEQ ID NO:5 is an amino acid sequence in which 32 amino acid residues of the 67th(Glu)–98th(Leu) in SEQ ID NO:5 is inserted between the 66th (Leu) and the 67th(Val) in SEQ ID NO:4.

Throughout this specification, proteins are represented in accordance with the conventions for description of peptides, that is the N-terminus (amino terminus) at left and the C-terminus (carboxyl terminus) at right. The protein of the present invention including the protein containing the amino acid sequence of SEQ ID NO:1 is usually in the carboxyl (—COOH) or carboxylate (—COO⁻) form at the C-terminus but may be in the amide (—CONH₂) or ester (—COOR) form.

R in the ester residue includes a $C_{1-6}$ alkyl group (e.g. methyl, ethyl, n-propyl, isopropyl, n-butyl, etc.), a $C_{3-8}$ cycloalkyl group (e.g. cyclopentyl, cyclohexyl, etc.), a $C_{6-12}$ aryl group (e.g. phenyl, α-naphthyl, etc.), a $C_{7-14}$ aralkyl group such as a phenyl-$C_{1-2}$ alkyl group (e.g. benzyl, phenethyl, etc.) and α-naphthyl-$C_{1-2}$ alkyl, (e.g. α-naphthylmethyl, etc.), as well as pivaloyloxymethyl group which is often used for the production of esters for oral administration.

When the protein of the present invention has a carboxyl or a carboxylate group in any position other than the C-terminus, the corresponding carboxamide or ester form is also included in the scope of the present invention. The ester mentioned just above such an esters mentioned for the C-terminal carboxyl group.

Furthermore, the protein of the present invention includes (1) the protein in which the N-terminus amino acid residue is protected with a protective group (e.g. $C_{1-6}$ acyl group such as $C_{1-6}$ alkanoyl such as formyl, acetyl, etc.), (2) the protein in which the N-terminal side of Gln has been cleaved in vivo to form pyroglutamic acid, (3) the protein in which a side chain of any relevant constituent amino acid (e.g. —OH, —SH, —NH₂, imidazole group, indole group, guanidino group, etc.) is protected by any protective group (e.g. $C_{1-6}$ acyl group such as $C_{1-6}$ alkanoyl such as formyl or acetyl, etc.), and (4) a complex protein such as glycoproteins obtained by attachment of sugar chains.

Examples of the protein of the present invention are (1) a protein which is derived from human-heart and comprises the amino acid sequence represented by SEQ ID NO:1 or SEQ ID NO:4 (FIG. 1), (2) a protein which is derived from human-kidney and comprises the amino acid sequence represented by SEQ ID NO:2 or SEQ ID NO:5 (FIG. 2), and a protein which is derived from murine-kidney and comprises the amino acid sequence represented by SEQ ID NO:3 (FIG. 3).

The precursor protein of the present invention, for example, is a protein in which one or more amino acids, preferably 1 to 10 amino acids, more preferably 1 to 100 amino acids, and still more preferably 1 to 200 amino acids are added to the N-terminal and/or C-terminal amino acid of the above-mentioned protein of the present invention.

Examples of the precursor protein of the present invention are a protein which comprises the amino acid sequence represented by SEQ ID NO:6, the amino acid sequence represented by SEQ ID NO:7 or the amino acid sequence represented by SEQ ID NO:8, or a substantial equivalent thereto.

Further, the precursor protein of the present invention may be any of the proteins derived from various tissues of man and other warm-blooded animals (e.g. guinea pig, rat, mouse, fowl, rabbit, swine, sheep, bovine, monkey, etc.), and also the precursor protein of the present invention may be a synthetic protein.

Examples of the precursor protein of the present invention are a protein which comprises an amino acid sequence substantially equivalent to the amino acid sequence represented by SEQ ID NO:6, SEQ ID NO:7 or SEQ ID NO:8 and comprises an amino acid sequence which is not less than about 50%, preferably not less than about 60%, more preferably not less than about 70%, still more preferably not less than about 80%, still more preferably not less than about 90%, and most preferably not less than about 95% identity to the amino acid sequence represented by SEQ ID NO:6, SEQ ID NO:7 or SEQ ID NO:8, and a protein which is able to produce the protein of the present invention. Therefore, the quantitative equivalency, such as a molecular weight, is not always necessary.

The precursor protein of the present invention may include any peptides comprising (1) an amino acid sequence wherein 1 or more amino acid residues (for example 1 to 30, preferably 1 to 10, more preferably a few (1 to 5) amino acid residues) are deleted from the amino acid sequence represented by SEQ ID NO:6, SEQ ID NO:7 or SEQ ID NO:8, (2) an amino acid sequence wherein 1 or more amino acid residues (for example 1 to 30, preferably 1 to 10, more preferably a few (1 to 5) amino acid residues) are added to the amino acid sequence represented by SEQ ID NO:6, SEQ ID NO:7 or SEQ ID NO:8, (3) an amino acid sequence wherein 1 or more amino acid residues (for example 1 to 30, preferably 1 to 10, more preferably a few (1 to 5) amino acid residues) are inserted into the amino acid sequence represented by SEQ ID NO:6, SEQ ID NO:7 or SEQ ID NO:8, (4) an amino acid sequence wherein 1 or more amino acid residues (for example 1 to 30, preferably 1 to 10, more preferably a few (1 to 5) amino acid residues) are substituted with the amino acid sequence represented by SEQ ID NO:6, SEQ ID NO:7 or SEQ ID NO:8, or (4) combinations thereof.

In the above-mentioned insertion, deletion or substitution are not so critical but are preferably positions other than (1) the 196th (Ala)–200th (Gly) residues of the amino acid sequence represented by SEQ ID NO:6, (2) the 228th (Ala)–232nd (Gly) residues of the amino acid sequence represented by SEQ ID NO:7, (3) the 129th (Val)–160th (Asp) residues of the amino acid sequence represented by SEQ ID NO:7, (4) the 196th (Ala)–200th (Gly) residues of the amino acid sequence represented by SEQ ID NO:8, and so on.

The precursor protein of the present invention including the protein which is usually in the carboxyl (—COOH) or carboxylate (—COO⁻) form at the C-terminus but may be in the amide (—CONH₂) or ester (—COOR) form, as above-mentioned protein of the present invention.

Furthermore, the precursor protein of the present invention includes (1) the protein in which the N-terminus amino acid residue (e.g. methionine residue) is protected with a protective group (e.g. $C_{1-6}$ acyl group such as $C_{1-6}$ alkanoyl such as formyl, acetyl, etc.), (2) the protein in which the N-terminal side of Gln has been cleaved in vivo to form pyroglutamic acid, (3) the protein in which the side chain of any relevant constituent amino acid (e.g. —OH, —SH, —NH₂, imidazole group, indole group, guanidino group, etc.) has been protected by any protective group (e.g. $C_{1-6}$ acyl group such as $C_{1-6}$ alkanoyl such as formyl or acetyl, etc.), and (4) a complex protein such as glycoproteins obtained by attachment of sugar chains, as above-mentioned protein of the present invention.

Examples of the precursor protein of the present invention are (1) the protein having the amino acid sequence represented by SEQ ID NO.:6, that is a protein having the amino acid sequence represented by SEQ ID NO:1 to which the signal peptide having the amino acid sequence-represented by SEQ ID NO:10 is added to N-terminus amino acid, (2) the protein having the amino acid sequence represented by SEQ ID:7, that is a protein having the amino acid sequence represented by SEQ ID NO:2 to which the signal peptide having the amino acid sequence represented by SEQ ID NO:10 is added to N-terminus amino acid, and so on.

The amino acid sequence represented by SEQ ID NO:7 is an amino acid sequence wherein the 32 amino acid residues (i.e. the 97th(Glu)–128th(Leu) residues) of the amino acid sequence represented by SEQ ID NO:7 is inserted between the 96th(Leu) and 97th(Val) of the amino acid sequence represented by SEQ ID NO:7.

As the precursor protein of the present invention has a signal peptide, the precursor protein of the present invention is able to secrete the protein of the present invention as a secreted protein efficiently. Also the precursor protein is useful as an intermediate for producing the protein of the present invention.

Moreover, as the precursor protein of the present invention is able to possess the same function as that of the protein of the present invention, the precursor protein of the present invention has the same usefulness as the protein of the present invention.

The partial peptide of the protein of the present invention may be any peptide having a qualitatively If equivalent activity to the above-mentioned protein of the present invention such as a LCAT-like activity and so on. For example, the partial peptides include peptides comprising at least not less than about 20, preferably not less than about 50, more preferably not less than about 70, for still better result, not less than about 100, best result, not less than about 200 amino acid residues of the amino acid sequence of the proteins of the present invention.

Examples of the partial peptide are a peptide comprises amino acid sequences selected from the amino acid sequences corresponding to the 3rd–25th residues, 27th–36th residues, 43rd–66th residues, 68th–86th residues, 92nd–98th residues, 107th–153rd residues, 155th–168th residues, 172nd–180th residues, 189th–240th residues, 256th–262nd residues, 268th–275th residues, 277th–287th residues, 295th–306th residues, 308th–332nd residues, 336th–347th residues and/or 351st–377th residues of the amino acid sequence represented by SEQ ID NO:1.

A preferable example of the partial peptide is a which comprises an amino acid sequence corresponding to the 163rd (Ala)–167th(Gly) residues of the amino acid sequence represented by SEQ ID NO:1 (that is, the 195th(Ala)–199th (Gly) residues of the amino acid sequence represented by SEQ ID NO:2, the 163rd(Ala)–167th(Gly) residues of the amino acid sequence represented by SEQ ID NO:3).

The partial peptide of the present invention includes the so called muteins, for example, proteins comprising (1) an amino acid sequence wherein one or more amino acid residues (preferably about 1 to 10, more preferably about a few (1 to 5) amino acid residues) are deleted from the above-mentioned partial peptide, (2) an amino acid sequence wherein one or more amino acid residues (preferably about 1 to 10, more preferably a few (1 to 5) amino acid residues) are added to the above-mentioned partial peptide, (3) an amino acid sequence wherein one or more amino acid residues (preferably about 1 to 10, more preferably a few (1 to 5) amino acid residues) are inserted into the above-mentioned partial peptide, (4) an amino acid sequence wherein one or more other amino acid residues in the above-mentioned partial peptide are substituted with 1 or more amino acid residues (preferably about 1 to 10, and more preferably a few (1 to 5) amino acid residues), or (5) combinations thereof.

The partial peptide of the present invention including the peptide which is usually in the carboxyl (—COOH) or carboxylate (—COO⁻) form at the C-terminus but may be in the amide (—CONH$_2$) or ester (—COOR) form, as above-mentioned protein of the present invention.

Furthermore, the partial peptide of the present invention includes (1) the peptide in which the N-terminus amino acid residue (e.g. methionine residue) has been protected with a protective group (e.g. $C_{1-6}$ acyl group such as $C_{1-6}$ alkanoyl such as formyl, acetyl, etc.), (2) the peptide in which the N-terminal side of Gln is cleaved in vivo to form pyroglutamic acid, (3) the peptide in which the side chain of any relevant constituent amino acid (e.g. —OH, —SH, —NH$_2$, imidazole group, indole group, guanidino group, etc.) is protected by any protective group (e.g. $C_{1-6}$ acyl group such as $C_{1-6}$ alkanoyl such as formyl or acetyl, etc.), and (4) a complex peptide such as glycoproteins obtained by attachment of sugar chains, as above-mentioned protein of the present invention.

Moreover, the partial peptide of the present invention is not always necessary to have a LCAT activity as the partial peptide of the present invention is able to be used as an antigen for producing an antibody.

Examples of the signal peptide of the present invention are a peptide which comprises the amino acid sequence represented by SEQ ID NO:9, the amino acid sequence represented by SEQ ID NO:10 or the amino acid sequence represented by SEQ ID NO:11, or a substantial equivalent thereto.

Further, the signal peptide of the present invention may be any of the proteins derived from various tissues of man and other warm-blooded animals (e.g. guinea pig, rat, mouse, fowl, rabbit, swine, sheep, bovine, monkey, etc.), and also the signal peptide of the present invention may be a synthetic peptide.

Examples of the signal peptide of the present invention are a peptide which comprises an amino acid sequence substantially equivalent to the amino acid sequence represented by SEQ ID NO:9, SEQ ID NO:10 or SEQ ID NO:11 and comprises an amino acid sequence which is not less than about 70%, preferably not less than about 80%, more preferably not less than about 90%, still more preferably not less than about 80%, still more preferably not less than about 90%, and most preferably not less than about 95% identity to the amino acid sequence represented by SEQ ID NO:9, SEQ ID NO:10 or SEQ ID NO:11, and a peptide comprises an amino acid sequence substantially equivalent to the amino acid sequence represented by SEQ ID NO:9, SEQ ID NO:10 or SEQ ID NO:11, and has a function as an signal peptide. Therefore, the quantitative equivalency, such as a molecular weight, is not always necessary.

The signal peptide of the present invention may include any peptides comprising (1) an amino acid sequence wherein 1 or more amino acid residues (for example 1 to 10, preferably 1 to 5, more preferably a few (1 to 3) amino acid residues) are deleted from the amino acid sequence represented by SEQ ID NO:9, SEQ ID NO:10 or SEQ ID NO:11, (2) an amino acid sequence wherein 1 or more amino acid residues (for example 1 to 10, preferably 1 to 5, more preferably a few (1 to 3) amino acid residues) are added to the amino acid sequence represented by SEQ ID NO:9, SEQ ID NO:10 or SEQ ID NO:11, (3) an amino acid sequence wherein 1 or more amino acid residues (for example 1 to 10, A preferably 1 to 5, more preferably a few (1 to 3) amino acid residues) are inserted into the amino acid sequence represented by SEQ ID NO:9, SEQ ID NO:10 or SEQ ID NO:11, (4) an amino acid sequence wherein 1 or more amino acid residues (for example 1 to 10, preferably 1 to 5, more preferably a few (1 to 3) amino acid residues) are substituted with the amino acid sequence represented by SEQ ID NO:9, SEQ ID NO:10 or SEQ ID NO:11, or (5) combinations thereof.

The signal peptide of the present invention includes the peptide which is usually in the carboxyl (—COOH) or carboxylate (—COO⁻) form at the C-terminus but may be in the amide (—CONH$_2$) or ester (—COOR) form, as above-mentioned protein of the present invention.

Furthermore, the signal peptide of the present invention includes (1) the peptide in which the N-terminus amino acid residue (e.g. methionine residue) is protected with a protective group (e.g. C$_{1-6}$ acyl group such as C$_{1-6}$ alkanoyl such as formyl, acetyl, etc.), (2) the peptide in which the N-terminal side of Gln is cleaved in vivo to form pyroglutamic acid, (3) the peptide in which the side chain of any relevant constituent amino acid (e.g. —OH, —SH, —NH$_2$, imidazole group, indole group, guanidino group, etc.) is protected by any protective group (e.g. C$_{1-6}$ acyl group such as C$_{1-6}$ alkanoyl such as formyl or acetyl, etc.), and (4) a complex peptide such as glycoproteins obtained by attachment of sugar chains, as above-mentioned protein of the present invention.

Examples of the signal peptide of the present invention are (1) a peptide comprising the amino acid sequence represented by SEQ ID NO:9, wherein the protein of the present invention comprises the amino acid sequence represented by SEQ ID NO:4 is deleted from the precursor protein of the present invention comprising the amino acid sequence represented by SEQ ID NO:6, (2) a peptide comprising the amino acid sequence represented by SEQ ID NO:10, wherein the protein of the present invention comprising the amino acid sequence represented by SEQ ID NO:1 is deleted from the precursor protein of the present invention comprises the amino acid sequence represented by SEQ ID NO:6, and (3) a peptide comprises the amino acid sequence represented by SEQ ID NO:11, wherein the protein of the present invention comprises the amino acid sequence represented by SEQ ID NO:3 is deleted from the precursor protein of the present invention comprising the amino acid sequence represented by SEQ ID NO:8, and so on.

The signal peptide of the present invention is able to secrete various kinds of secreted proteins, including the protein of the present invention, efficiently.

The salts of the protein, the precursor protein, the partial peptide or the signal peptide of the present invention includes salts with physiologically acceptable bases (e.g. alkali metals) or acids such as organic or inorganic acids, and is preferably a physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.)

The protein, the precursor protein or a salt thereof of the present invention can be produced from the tissues or cells of human or other warm-blooded animals by per se known purification techniques or, as described hereinafter, by culturing a transformant carrying a DNA encoding the protein. It can also be produced in accordance with the procedures for peptide synthesis which are described hereinafter.

When the protein or the precursor protein of the present invention is produced from the tissues or cells of human or other warm-blooded animals, the tissues or cells of human or other warm-blood animals are homogenized and the protein of the present invention is extracted by an acid, etc. The protein can be isolated and purified from the extract by a combination of chromatography such as reverse phase chromatography, ion exchange chromatography and so on.

For the synthesis of the protein, the precursor protein, the partial peptide, the signal peptide or their salts, or their amide form of the present invention, any of commercial resins available for protein synthesis can be employed. Among such resins are chloromethyl resin, hydroxymethyl resin, benzhydrylamino resin, aminomethyl resin, 4-benzyloxybenzyl alcohol resin, 4-methylbenzhydrylamino resin, PAM resin, 4-hydroxymethyl-methylphenylacetamidomethyl resin, polyacrylamide resin, 4-(2',4'-dimethoxyphenyl-hydroxymethyl)phenoxy resin, and 4-(2',4'-dimethoxyphenyl-Fmoc-aminoethyl)phenoxy resin. Using such a resin, amino acids which may be beforehand protected at side-chain functional groups in a suitable manner can be serially condensed with the α-amino group in the order corresponding to the amino acid sequence of the objective protein by various condensation techniques which are per se known. After completion of the final condensation reaction, the protein is separated from the resin and the protective groups are removed. Then, in highly diluted solution, the intramolecular disulfide-forming reaction is carried out to provide the objective proteins or amides thereof.

Referring to the above condensation of protected amino acids, various activating agents known to be useful for protein synthesis can be utilized, and carbodiimide reagents are especially preferred. The carbodiimide reagents include DCC, N,N'-diisopropylcarbodiimide, N-ethyl-N'-(3-dimethylaminoprolyl)carbodiimide and so on. For activation by these reagents, the protected amino acid and a racemization inhibitor (e.g. HOBt, HOOBt, etc.) can be directly added to the resin, or the protected amino acid can be activated beforehand in the form of symmetric acid anhydride, HOBt ester or HOOBt ester and, then, added to the resin.

The solvent used for the above-mentioned activation of protected amino acids or a conjugation thereof to the resin can be properly selected from among the solvents known to be useful for protein condensation reactions. Examples of the solvent are acid amides (e.g. N,N-dimethylformamide, N,N-dimethylacetamide, N-methylpyrrolidone, etc.), halogenated hydrocarbons (e.g. methylene chloride, chloroform, etc.), alcohols (e.g. trifluoroethanol, etc.), sulfoxides (e.g. dimethyl sulfoxide, etc.), ethers (e.g. dioxane, tetrahydrofuran, etc.), nitriles (e.g. acetonitrile, propionitrile, etc.), esters (e.g. methyl acetate, ethyl acetate, etc.), and suitable mixtures of these solvents. The reaction temperature can be selected from the range known to be useful for protein-forming reactions, usually the range of about −20° C. to about 50° C. The activated amino acid derivative is generally used in a 1.5 to 4-fold excess. When the condensation is found insufficient by ninhydrin assay, the reaction can be repeated to make the condensation thoroughly sufficient. When sufficient condensation can not be achieved by repeated reaction, an unreacted amino acid can be acetylated by using acetic anhydride or acetylimidazole so as not to effect a subsequent reaction.

The protective groups for protecting the amino group of the starting compound include Z, Boc, t-pentyloxycarbonyl, isobornyloxycarbonyl, 4-methoxy-benzyloxycarbonyl, Cl-Z, Br-Z, adamantyloxycarbonyl, trifluoroacetyl, phthaloyl, formyl, 2-nitrophenylsulfenyl, diphenylphosphinothioyl, Fmoc, and so on.

The carboxyl group can be protected in the form of, for example, an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), an aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected in the form of an ester or an ether. The group suitable for esterification includes carboxylic acid-derived acyl groups such as a lower($C_{1-6}$) alkanoyl group (e.g. acetyl, etc.), an aroyl group (e.g. benzoyl, etc.), a benzyloxycarbonyl, an ethoxycarbonyl group and so on. The group suitable for etherification includes a benzyl group, a tetrahydropyranyl group, a t-butyl group and so on.

The protective group used for protecting the phenolic hydroxyl group of tyrosine includes Bzl, $C^{12}$-Bzl, 2-nitrobenzyl, Br-Z, t-butyl and so on.

The protective group for the imidazole group of histidine includes Tos, 4-methoxy-2,3,6-trimethylbenzenesulfonyl, DNP, benzyloxymethyl, Bum, Boc, Trt, Fmoc and so on.

The starting compound with activated carboxyl groups includes the corresponding acid anhydride, azide, and active ester (e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc.). The starting compound with activated amino groups includes the corresponding phosphorylamide.

The method for removal of such protective groups includes catalytic reduction in a hydrogen stream in the presence of a catalyst (e.g. Pd black or Pd-on-carbon), acid treatment with anhydrous hydrogen fluoride, methanesulfonic acid, trifluoromethanesulfonic acid, trifluoroacetic acid or a mixture thereof, treatment with a base such as diiso-propylethylamine, triethylamine, piperidine, piperazine or the like, and reduction with sodium metal in liquid ammonia. The above deprotection by treatment with acid is generally conducted at a temperature of about −20° C. to 40° C. This acid treatment can be carried out advantageously in the presence of a cation acceptor such as anisole, phenol, thioanisole, m-cresol, p-cresol, dimethyl sulfide, 1,4-butanedithiol, 1,2-ethanedithiol, or the like. The 2,4-dinitrophenyl group used for protecting the imidazole group of histidine can be removed by treatment with thiophenol, and the formyl group used for protecting the indole group of tryptophan can be removed not only by said acid treatment in the presence of 1,2-ethanedithiol, 1,4-butanedithiol or the like as described hereinbefore, but also by alkali treatment with diluted sodium hydroxide solution, diluted liquid ammonia, or the like.

The method for protecting any functional group that should not take part in the contemplated reaction, the protective group to be used for such protection, the method for eliminating the protective group, and the method for activating the functional group to be involved in the contemplated reaction can all be properly selected from among the known methods and groups.

An alternative method for providing the protein in amide form typically comprises protecting the α-carboxyl group of the C-terminal amino acid in the form of an amide, extending the peptide (protein) chain to a desired length towards the N-terminus, deprotecting the N-terminal α-amino acid of the resulting peptide chain selectively to provide an N-terminal-deprotected fragment, preparing a peptide (protein) fragment with its C-terminal carboxyl group selectively deprotected, and condensing the two fragments in a solvent such as the mixed solvent as mentioned above. The condensation reaction can be carried out in the same manner as described hereinbefore. After purification of the protected protein thus obtained by condensation, all the protective groups are eliminated by the procedures described hereinbefore to provide the contemplated protein in a crude form. This crude protein is purified by suitable known purification techniques and lyophilized to provide the desired protein amide.

A method for providing the protein in an ester form comprises condensing the α-carboxyl group of the C-terminal amino acid with a suitable alcohol to prepare the corresponding ester and subjecting this ester to the same procedure as described for purification of the protein amide to provide the objective protein ester.

The partial peptide, the signal peptide of the present invention or a salt thereof can be produced by per se known procedures for peptide synthesis or by cleaving the protein or the precursor protein of the present invention with a suitable peptidase. The process for peptide synthesis may be a solid-phase synthesis and/or a liquid-phase synthesis. Namely, the objective peptide can be produced by condensing a partial peptide or amino acid capable of constituting the protein with the residual part thereof and, when the product has a protective group, the protective group is removed whereupon a desired peptide can be manufactured. The known technology for condensation and deprotection includes the procedures described in the following literature (1)–(5).

(1) M. Bodanszky and M. A. Ondetti, Peptide Synthesis, Interscience Publishers, New York, 1966
(2) Schroeder and Luebke, The Peptide, Academic Press, New York, 1965
(3) Nobuo Izumiya et al., Fundamentals and Experiments in Peptide Synthesis, Maruzen, 1975
(4) Haruaki Yajima and Shumpei Sakakibara, Biochemical Experiment Series 1, Protein Chemistry IV, 205, 1977
(5) Haruaki Yajima (ed.), Development of Drugs-Continued, 14, Peptide Synthesis, Hirokawa Shoten After the reaction, the partial peptide of the present invention can be isolated and purified by a combination of conventional purification techniques such as solvent extraction, distillation, column chromatography, liquid chromatography, and recrystallization. When the partial peptide isolated as above is in a free form, it can be converted to a suitable salt by known methods or method analogous thereto. On the other hand, when it is isolated as a salt, it can be converted to a free form or to another salt by known methods or method analogous thereto.

The DNA coding for the protein of the present invention may be any DNA comprising a nucleotide sequence encoding the protein of the present invention as mentioned above. It may also be any one of genomic DNA, genomic DNA library, cDNA derived from the tissues or cells as mentioned above, cDNA library derived from the tissues or cells as mentioned above, and synthetic DNA.

The vector for constructing a library may include bacteriophage, plasmid, cosmid, and phagemid. Furthermore, using a total RNA fraction or an mRNA fraction prepared from the tissues or cells, a direct amplification can be carried out by Reverse Transcriptase Polymerase Chain Reaction (hereinafter, referred to as RT-PCR method) technique.

Examples of the DNA coding for the protein of the present invention are (1) a DNA comprising a nucleotide sequence represented by SEQ ID NO:12, or a DNA which comprises a nucleotide sequence hybridizing to the nucleotide sequence represented by SEQ ID NO:12 under a highstringent condition and codes for a protein having a substantially equivalent activity (e.g. LCAT activity etc.) to the protein of the present invention, (2) a DNA comprising a nucleotide sequence represented by SEQ ID NO:13, or a DNA which comprises a nucleotide sequence hybridizing to the nucleotide sequence represented by SEQ ID NO:13 under a highstringent condition and codes for a protein having a substantially equivalent activity (e.g. LCAT activity etc.) to the protein of the present invention, (3) a DNA comprising a nucleotide sequence represented by SEQ ID NO:14, or a DNA which comprises a nucleotide sequence hybridizing to the nucleotide sequence represented by SEQ ID NO:14 under a highstringent condition and codes for a protein having a substantially equivalent activity (e.g. LCAT activity etc.) to the protein of the present invention, (4) a DNA comprising a nucleotide sequence represented by SEQ ID NO:15, or a DNA which comprises a nucleotide sequence hybridizing to the nucleotide sequence represented by SEQ ID NO:15 under a highstringent condition and codes for a protein having a substantially equivalent activity (e.g. LCAT activity etc.) to the protein of the present invention, or (5) a DNA comprising a nucleotide sequence represented by SEQ ID NO:16, or a DNA which comprises a nucleotide sequence hybridizing to the nucleotide sequence represented by SEQ ID NO:16 under a highstringent condition and codes for a protein having a substantially equivalent activity (e.g. LCAT activity etc.) to the protein of the present invention, and so on.

Examples of the DNA which comprises the nucleotide sequence hybridizing to the nucleotide sequence represented by SEQ ID NO:12 to SEQ ID NO:16 under a highstringent condition are a DNA comprising a nucleotide sequence of not less than about 70%, preferably not less than about 80%, more preferably not less than about 90%, for still better result, not less than about 95% identity to the nucleotide sequence represented by SEQ ID NO:12 to SEQ ID NO:16.

The hybridization can be carried out by per se known methods such as the method described in Molecular Cloning, 2nd (J. Sambrook et al., Cold Spring Harbor Lab. Press, 1989) and so on. When a commercially available library is used, the hybridization can be carried out in accordance with the instructions given in the accompanying manual, and particularly, be carried out under a highstringent condition.

Under the highstringent condition, $Na^+$ concentration is at about 19 to 40 mM, preferably about 19 to 20 mM and a temperature is at about 50 to 70° C., preferably about 60 to 65° C. Particularly, the condition at about 19 mM of $Na^+$ and about 65° C. is preferred.

Preferable examples of the DNA coding for the protein comprising the amino acid sequence represented by SEQ ID NO:1 are a DNA comprising the nucleotide sequence represented by SEQ ID NO:12.

Preferable examples of the DNA comprising the DNA coding for the protein having the amino acid sequence represented by SEQ ID NO:2 are a DNA comprising the nucleotide sequence represented by SEQ ID NO:13, and so on.

Preferable examples of the DNA comprising the DNA coding for the protein having the amino acid sequence represented by SEQ ID NO:3 are a DNA comprising the nucleotide sequence represented by SEQ ID NO:14, and so on.

Preferable examples of the DNA comprising the DNA coding for the protein having the amino acid sequence represented by SEQ ID NO:4 are a DNA comprising the nucleotide sequence represented by SEQ ID NO:15, and so on.

Preferable examples of the DNA comprising the DNA coding for the protein having the amino acid sequence represented by SEQ ID NO:5 are a DNA comprising the nucleotide sequence represented by SEQ ID NO:16, and so on.

The DNA coding for the precursor protein of the present invention may be any DNA comprising a nucleotide sequence encoding the precursor protein of the present invention as mentioned above. It may also be any one of genomic DNA, genomic DNA library, cDNA derived from the tissues or cells as mentioned above, cDNA library derived from the tissues or cells as mentioned above, and synthetic DNA.

Examples of the DNA coding for the precursor protein of the present invention are (1) a DNA comprising a nucleotide sequence represented by SEQ ID NO:17, or a DNA which comprises a nucleotide sequence hybridizing to the nucleotide sequence represented by SEQ ID NO:17 under a highstringent condition and codes for a protein which is able to produce the above-mentioned precursor protein of the present invention, (2) a DNA comprising a nucleotide sequence represented by SEQ ID NO:18, or a DNA which comprises a nucleotide sequence hybridizing to the nucleotide sequence represented by SEQ ID NO:18 under a highstringent condition and codes for a protein which is able to produce the above-mentioned precursor protein of the present invention, or (3) a DNA comprising a nucleotide sequence represented by SEQ ID NO:19, or a DNA which comprises a nucleotide sequence hybridizing to the nucleotide sequence represented by SEQ ID NO:19 under a highstringent condition and codes for a protein which is able to produce the above-mentioned precursor protein of the present invention, and so on.

Examples of the DNA which comprises the nucleotide sequence hybridizing to the nucleotide sequence represented by SEQ ID NO:17 to SEQ ID NO:19 under a highstringent condition are a DNA comprising a nucleotide sequence of not less than about 70%, preferably not less than about 80%, more preferably not less than about 90%, for still better result, not less than about 95% identity to the nucleotide sequence represented by SEQ ID NO:17 to SEQ ID NO:19.

The method of the hybridization and the highstringent condition are the same as mentioned-above.

A preferable example of the DNA comprising the DNA coding for the precursor protein having the amino acid sequence represented by SEQ ID NO:6 is a DNA comprising the nucleotide sequence represented by SEQ ID NO:17, and so on.

A preferable example of the DNA comprising the DNA coding for the precursor protein having the amino acid sequence represented by SEQ ID NO:7 is a DNA comprising the nucleotide sequence represented by SEQ ID NO:18, and so on.

A preferable example of the DNA comprising the DNA coding for the precursor protein having the amino acid sequence represented by SEQ ID NO:8 is a DNA comprising the nucleotide sequence represented by SEQ ID NO:19, and so on.

The DNA coding for the precursor protein of the present invention may be any DNA comprising a nucleotide sequence encoding the precursor protein of the present invention as mentioned above. It may also be any one of genomic DNA, genomic DNA library, cDNA derived from the tissues or cells as mentioned above, cDNA library derived from the tissues or cells as mentioned above, and synthetic DNA.

Examples of the DNA coding for the partial peptide of the present invention are (1) a DNA comprising a nucleotidze sequence represented by SEQ ID NO:12, or a DNA which comprises a nucleotide sequence hybridizing to the nucleotide sequence represented by SEQ ID NO:12 under a highstringent condition and comprising a partial nucleotide sequence of a nucleotide sequence coding for the protein of the present invention or a substantial equivalent thereto, (2) a DNA comprising a nucleotide sequence represented by SEQ ID NO:13, or a DNA which comprises a nucleotide sequence hybridizing to the nucleotide sequence represented by SEQ ID NO:13 under a highstringent condition and comprising a partial nucleotide sequence of a nucleotide sequence coding for the protein of the present invention or a substantial equivalent thereto, (3) a DNA comprising a nucleotide sequence represented by SEQ ID NO:14, or a DNA which comprises a nucleotide sequence hybridizing to the nucleotide sequence represented by SEQ ID NO:14 under a highstringent condition and comprising a partial nucleotide sequence of a nucleotide sequence coding for the protein of the present invention or a substantial equivalent thereto, (4) a DNA comprising a nucleotide sequence represented by SEQ ID NO:15, or a DNA which comprises a nucleotide sequence hybridizing to the nucleotide sequence represented by SEQ ID NO:15 under a highstringent condition and comprising a partial nucleotide sequence of a nucleotide sequence coding for the protein of the present invention or a substantially equivalent thereto, or (5) a DNA comprising a nucleotide sequence represented by SEQ ID NO:15, or a DNA which comprises a nucleotide sequence hybridizing to the nucleotide sequence represented by SEQ ID NO:15 under a highstringent condition and comprising a partial nucleotide sequence of a nucleotide sequence coding for the protein of the present invention or a substantially equivalent thereto, and so on.

Examples of the DNA which comprises the nucleotide sequence hybridizing to the nucleotide sequence represented by SEQ ID NO:12 to SEQ ID NO:16 under a highstringent condition are a DNA comprising a nucleotide sequence of not less than about 70%, preferably not less than about 80%, more preferably not less than about 90%, for still better result, not less than about 95% identity to the nucleotide sequence represented by SEQ ID NO:12 to SEQ ID NO:16.

The method of the hybridization and the highstringent condition are the same as mentioned-above.

Specifically, examples of the DNA coding for the partial peptide having at least one amino acid sequence selected from the amino acid sequences of the 3rd–25th amino acid residues, 27th–36th residues, 43rd–66th residues, 68th–86th residues, 92nd–98th residues, 107th–153rd residues, 155th–168th residues, 172nd–180th residues, 189th–240th residues, 256th–262nd residues, 268th–275th residues, 277th–287th residues and 295th–306th residues, 308th–332nd, 336th–347th and/or 351st–377th respectively, of the amino acid sequence represented by SEQ ID NO:1 are a DNA having at least one nucleotide sequence selected from sequences of the 7th–75th nucleotide sequence, 79th–108th nucleotide sequence, 127th–198th nucleotide sequence, 202nd–258th nucleotide sequence, 274th–294th nucleotide sequence, 319th–459th nucleotide sequence, 463rd–504th nucleotide sequence, 514th–540th nucleotide sequence, 565th–720th nucleotide sequence, 766th–786th nucleotide sequence, 802nd–825th nucleotide sequence, 829th–861st nucleotide sequence, 883rd–918th nucleotide sequence, 922nd–996th nucleotide sequence, 1006th–1041st nucleotide sequence, and/or 1051st–1131st nucleotide sequence, respectively, of the nucleotide sequence represented by SEQ ID NO:12 and so on.

The DNA coding for the signal peptide of the present invention may be any DNA comprising a nucleotide sequence encoding the signal peptide of the present invention as mentioned above. It may also be any one of genomic DNA, genomic DNA library, cDNA derived from the tissues or cells as mentioned above, cDNA library derived from the tissues or cells as mentioned above, and synthetic DNA.

Examples of the DNA coding for the signal peptide of the present invention are (1) a DNA comprising a nucleotide sequence represented by SEQ ID NO:20, or a DNA which comprises a nucleotide sequence hybridizing to the nucleotide sequence represented by SEQ ID NO:20 under a highstringent condition and coding for the peptide having a function as a signal peptide, (2) a DNA comprising a nucleotide sequence represented by SEQ ID NO:21, or a DNA which comprises a nucleotide sequence hybridizing to the nucleotide sequence represented by SEQ ID NO:21 under a highstringent condition and coding for the peptide having a function as a signal peptide, (3) a DNA comprising a nucleotide sequence represented by SEQ ID NO:22, or a DNA which comprises a nucleotide sequence hybridizing to the nucleotide sequence represented by SEQ ID NO:22 under a highstringent condition and coding for the peptide having a function as a signal peptide, and so on.

Examples of the DNA which comprises the nucleotide sequence hybridizing to the nucleotide sequence represented by SEQ ID NO:20 to SEQ ID NO:22 under a highstringent condition are a DNA comprising a nucleotide sequence of not less than about 70%, preferably not less than about 80%, more preferably not less than about 90%, for still better result, not less than about 95% identity to the nucleotide sequence represented by SEQ ID NO:20 to SEQ ID NO:22.

The method of the hybridization and the highstringent condition are the same as mentioned-above.

A preferable example of the DNA comprising the DNA coding for the signal peptide having the amino acid sequence represented by SEQ ID NO:9 is a DNA comprising the nucleotide sequence represented by SEQ ID NO:20, and so on.

A preferable example of the DNA comprising the DNA coding for the signal peptide having the amino acid sequence represented by SEQ ID NO:10 is a DNA comprising the nucleotide sequence represented by SEQ ID NO:21, and so on.

A preferable example of the DNA comprising the DNA coding for the signal peptide having the amino acid sequence represented by SEQ ID NO:11 is a DNA comprising the nucleotide sequence represented by SEQ ID NO:22, and so on.

The DNA encoding the protein, the precursor protein, the partial peptide or the signal peptide of the present invention (hereinafter, these proteins or peptides are sometimes referred to briefly as the protein of the present invention) can be cloned either by PCR amplification using synthetic DNA primers having a partial nucleotide sequence of the DNA coding for the protein or by hybridization using the DNA inserted in a suitable vector and labeled DNA fragment or synthetic DNA coding for a part or full region of the protein or the partial peptide of the present invention. The hybridization can be carried out by the method described in Molecular Cloning, 2nd (J. Sambrook et al., Cold Spring Harbor Lab. Press, 1989). When a commercially available DNA library is used, the instructions given in the accompanying manual can be followed.

The substitution of the nucleotide sequence of the DNA can be carried out by the per se known method such as Gapped duplex method, Kunkel method and so on by using the known kits such as MutanTM-G (Takara corporation), MutanTM-K (Takara corporation) and so on.

The cloned DNA coding for the protein or the partial peptide of the present invention can be used directly or after digestion with a restriction enzyme or after addition of a linker depending on purposes. This DNA may have ATG as the translation initiation codon at the 5' end and TAA, TGA, or TAG as the termination codon at the 3' end. The translation initiation and termination codons can be added by means of suitable DNA adapters.

An expression vector for the protein of the present invention can be constructed by, for example, (a) cutting out an objective DNA fragment from the DNA for the protein of the present invention and (b) ligating the objective DNA fragment with the downstream of a promoter in a suitable expression vector.

The vector may include plasmids derived from *Escherichia coli*, e.g., pBR322, pBR325, pUC12, pUC13, etc.; plasmids derived from *Bacillus subtilis*, e.g., puB110, pTP5, pC194, etc.; plasmids derived from yeasts e.g., pSH19, pSH15, etc.; bacteriophages such as λ-phage: animal virus such as retrovirus, vaccinia virus, etc.; insect virus; and other vectors such as pA1–11, pXT1, pRc/CMV, pRc/RSV, pcDNAI/Neo and so on.

According to the present invention, any promoter can be used as long as it is appropriate for the host cell which is used for expressing a gene. When the host is an animal cell, the promoter includes SR α, SV40 promoter, LTR promoter, CMV(cytomegalovirus) promoter, HSV-TK promoter, etc., and CMV promoter and SR α promoter are preferably used. When the host for the transformation is *Escherichia coli*, the promoter is preferably trp promoter, lac promoter, recA promoter, λPL promoter, lpp promoter, T7 promoter, etc. When the host for the transformation is Bacillus, the promoter is preferably SPO1 promoter, SPO2 promoter, penP promoter, etc. When the host is a yeast, the promoter is preferably PHO5 promoter, PGK promoter, GAP promoter, ADH promoter, AOX1 promoter, etc. When the host is an insect cell, the promoter include polyhedrin promoter, P10 promoter, etc.

The expression vectors may, if necessary, further comprise enhancers, splicing signals, polyadenylation signals, selective markers, SV40 duplicate origin (hereinafter referred to as SV40 ori). Examples of selective markers are dihydrofolate reductase (hereinafter referred to as dhfr gene, ampicillin resistant gene (hereinafter referred to as Amp$^r$), neomycin-resistant gene (hereinafter referred to as Neo$^r$) and so on. The dhfr gene gives methotrexate (MTX) resistant and Neo gives G418 resistant. Particularly, when the dhfr gene is used as a selective marker against dhfr gene-deficient chinese hamster cell line, cells transfected by the objective gene can be selected in a thymidine-free medium.

Furthermore, an appropriate signal sequence for a host can be added to the N-terminal side of the protein. When the host is *Escherichia coli*, the utilizable signal sequences may include PhoA signal sequence, OmpA signal sequence, etc. When the host is Bacillus, they may include α-amylase signal sequence, subtilisin signal sequence, etc. When the host is a yeast, they may include MFα signal sequence, SUC2 signal sequence, etc. When the host is an animal cell, they may include insulin signal sequence, α-interferon signal sequence, antibody molecule signal sequence, etc.

A transformant or transfectant is obtained by using the vector thus constructed, which carries the DNA coding for the protein of the present invention.

The host may be, for example, Escherichia species, Bacillus species, yeast cells, insect cells, insects, animal cells, etc.

Examples of Escherichia species include *Escherichia coli* K12.DH1 (Proceedings of the National Academy of Sciences of the United State of America, Vol. 60, 160 (1968)), JM103 (Nucleic Acids Research, Vol. 9, 309 (1981)), JA221 (Journal of Molecular Biology, Vol. 120, 517 (1978)), HB101 (Journal of molecular Biology, Vol, 41, 459 (1969)), C600 [Genetics, Vol. 39, 440 (1954)), etc.

Examples of Bacillus species are, for example, *Bacillus subtilis* MI114 (Gene, Vol. 24, 255 (1983)), 207–21 (Journal of Biochemistry, Vol. 95, 87 (1984)), etc.

Examples of yeast cells are, for example, *Saccharomyces cerevisiae* AH22, AH22R$^-$, NA87-11A, DKD-5D or 20B-12, *Schizosachcaromyces pombe* NCYC1913 or *Pichia pastoris* KM71, etc.

Examples of insect cells are, for example, *Spodoptera frugiperda* cell (Sf cell), MG1 cell derived from a center intestine of Trichoplusia ni, High Five™ cell derived from eggs of Trichoplusia ni, *Mamestra brassicae*-derived cell, *Estiamena acrea*-derived cell and so on when virus is AcNPV; and *Bombvx mori* N cell (BmN cell,) and so on when virus is BmNPV. Examples of the Sf cell are, for example, Sf9 cell (ATCC CRL 1711), Sf21 cell [both, Vaughn J. L. et al., In Vivo, 13, 213–217(1977)] and so on.

Examples of insects include a larva of silkworm (*Bombyx mori* larva) (Maeda et al., Nature, 315, 592(1985)).

Examples of animal cells are, for example, monkey-derived COS-7 cell line, Vero cell line, Chinese hamster ovary cell line (hereinafter referred to as CHO cell), dhfr gene-deficient Chinese hamster cell line (hereinafter referred to as CHO(dhfr$^-$) cell), mouse L cell, mouse AtT-20, mouse myeloma cell, rat GH3, human FL, 293 cell, C127 cell, BALB3T3 cell, Sp-2/O cell, etc. Among them, CHO cell, CHO(dhfr$^-$) cell, 293 cell, etc. are preferred.

Depending on host cells used, transformation is carried out using standard techniques appropriate to such cells.

Transformation of Escherichia species can be carried out in accordance with methods as disclosed in, for example, Proceedings of the National Academy of Sciences of the United State of America, Vol. 69, 2110 (1972), and Gene, Vol. 17, 107 (1982), etc.

Transformation of Bacillus species can be carried out in accordance with methods as disclosed in, for example, Molecular & General Genetics, Vol. 168, 111 (1979), etc.

Transformation of yeast cells can be carried out in accordance with methods as disclosed in, for example, Methods in Enzymology, 194, 182–187(1991), etc.

Transformation of insect cells or insects can be carried out in accordance with methods as disclosed in, for example, Bio/Technology, 6, 47–55, (1988).

Transformation of animal cells can be carried out by methods as disclosed in, for example, Cell Engineering, separate vol. 8, New Cell Engineering Experiment Protocol, 263–267(1995) (Shujun Company), Virology, Vol. 52, 456 (1973), etc.

In introducing the expression vector into cells, known methods such as a calcium phosphate method (Graham, F. L. and van der Eb, A. J.: Virology, 52, 456–467(1973)), an electroporation (Neumann, E. et al., EMBO Journal, 1,841–845(1982)), etc. may be used.

The transformants or transfectants wherein the expression vector carrying the DNA coding for the protein can be obtained according to the afore-mentioned techniques.

Examples of methods for expressing the protein of the present invention stably using animal cells are a method for selecting the cells wherein the above-mentioned expression vector is integrated on the chromosome by means of clone selection. Briefly, the transformant is first selected using the above-mentioned selective marker as an index for selection. Then the animal cell obtained as such using the selective marker is repeatedly subjected to a clone selection to establish an animal cell strain which stably exhibits a high ability of expressing the protein of the present invention. When a dhfr gene is used as a selective marker, the resistant cells are selected from a culture with a sequentially increased MTX concentration to amplify the DNA coding for the protein of the present invention with dhfr gene in the cells whereby an animal cell strain exhibiting far higher expression can be obtained.

The protein of the present invention or a salt thereof can be also manufactured by culturing the transformant under a condition where the DNA coding for the protein of the present invention can be expressed to express and accumulate the protein of the present invention.

Culture of the transformants (transfectants) of Escherichia or Bacillus species can be carried out preferably in a liquid culture medium. The culture medium may contain carbon sources, nitrogen sources, minerals, etc. which are necessary for growing the transformants. The carbon sources may include glucose, dextrin, soluble starch, sucrose, etc. The nitrogen sources may include organic or inorganic substances such as ammonium salts, nitrates, corn steep liquor, peptone, casein, meat extracts, bean-cakes, potato extracts, etc. Examples of the minerals may include calcium chloride, sodium dihydrogen phosphate, magnesium chloride, etc. It is further allowable to add yeast extracts, vitamines, growth-promoting factors, etc. It is suitable that the pH of culture medium is at about 5 to 8.

The culture medium for Escherichia species is, for example, preferably M9 medium which contains glucose and casamino acids (Miller, Journal of Experiments in Molecular Genetics, 431–433, Cold Spring Harbor Laboratory, New York, (1972). If necessary, drugs such as 3β-indolyl acrylic acid can be added to the medium to improve efficiency of the promoter. In the case of Escherichia species as a host, the culture is carried out usually at about 15 to 43° C. for about 3 to 24 hours. When necessary, aeration and stirring may be applied. In the case of Bacillus species as a host, the culture is carried out usually at about 30 to 40° C. for about 6 to 24 hours. When necessary, aeration and stirring may also be applied.

In the case of yeast transformant cells, the culture medium used may include, for example, Burkholder minimum medium (Bostian, K. L. et al., Proceedings of the National Academy of Sciences of the United State of America, Vol. 77, 4505 (1980)), SD medium containing 0.5% casamino acid (Bitter, G. A. et al., Proceedings of the National Academy of Sciences of the United State of America, Vol. 81, 5330 (1984)), etc. It is preferable that the pH of the culture medium is adjusted to be from about 5 to 8. The culture is carried out usually at about 20 to 35° C. for about 24 to 72 hours. When necessary, aeration and stirring may be applied.

In the case of the transformants (or transfectants) of insect cells or insects, the culture medium used may include the Grace's insect medium supplemented with additives such as inactivated 10% bovine serum (Grace, T.C.C., Nature, 195, 788 (1962)). It is preferable that the pH of the culture medium is adjusted to be about 6.2 to 6.4. The culture is usually carried out at about 27° C. for about 3 to 5 days. When necessary, aeration and stirring may be applied.

In the case of the transformants (or transfectants) of animal cells, the culture medium used may include MEM medium (Science, Vol. 122, 501 (1952)), DMEM medium (Virology, Vol. 8, 396 (1959)), RPMI 1640 medium (Journal of the American Medical Association, Vol. 199, 519 (1967)), 199 medium (Proceedings of the Society of the Biological Medicine, Vol. 73, 1 (1950)), etc. which are containing, for example, about 5 to 20% of fetal calf serum. It is preferable that the pH is from about 6 to 8. The culture is usually carried out at about 30 to 40° C. for about 15 to 60 hours. When necessary, medium exchange, aeration and stirring may be applied. Especially when CHO (dhfr-) cells and dhfr selective marker gene are used, it is preferred to use DMEM medium containing dialyzed fetal bovine serum which rarely contains thymidine.

Separation and purification of the protein from the above-mentioned cultures can be carried out according to the methods described herein below.

To extract the protein from the cultured medium, microorganisms, insects cells or animal cells are collected by known methods after the culture, suspended in a suitable buffer solution, disrupted by sonication, lysozyme treatment and/or freezing and thawing, etc. and, then, a crude protein extract is obtained by centrifugation or filtration. Other conventional extraction or isolation methods can be applied. The buffer solution may contain a protein-denaturing agent such as urea or guanidine hydrochloride or a surfactant such as Triton X-100™.

In the case where proteins are secreted into culture media, supernatants are separated from the microorganisms, insect cells or animal cells after culture and collected by known methods. The culture supernatant containing the protein can be purified by suitable combinations of known methods for separation, isolation and purification. The known methods of separation, isolation and purification may include methods which utilizes a difference in solubility, such as salting out or sedimentation with solvents, methods which utilizes chiefly a difference in the molecular size or weight, such as dialysis, ultrafiltration, gel filtration and SDS-polyacrylamide gel electrophoresis, methods utilizing a difference in the electric charge, such as ion-exchange chromatography, methods utilizing specific affinity such as affinity chromatography, methods utilizing a difference in the hydrophobic property, such as reversed-phase high-performance liquid chromatography, and methods utilizing a difference in the isoelectric point such as isoelectric electrophoresis, etc.

In cases where the protein thus obtained is in a free form, the free-form protein can be converted to a salt thereof by known methods or method analogous thereto. In case where the protein thus obtained is in a salt form vice versa, the protein salt can be converted to a free form or to another salt by known methods or method analogous thereto.

The protein produced by the transformant can be arbitrarily modified or a polypeptide can be partly removed therefrom, by a suitable protein-modifying enzyme before or after the purification. The protein-modifying enzyme may include trypsin, chymotrypsin, arginyl endopeptidase, protein kinase, glycosidase, etc. The amount of the protein of the present invention thus obtained can be measured by a binding assay with a labeled ligand or by an enzyme immunoassays (enzyme linked immunoassays) using specific antibodies.

The antibodies against the protein, the precursor protein, or the partial peptide of the present invention, or a salt thereof are any antibodies such as polyclonal antibodies and monoclonal antibodies which can recognize the protein, the precursor protein, or the partial peptide of the present invention, or a salt thereof (hereinafter referred to as the protein of the present invention).

The antibodies against the protein of the present invention may be manufactured by methods per se known to those of skill in the art or methods similar thereto, using the protein of the present invention as antigen. For example, monoclonal antibodies and/or polyclonal antibodies can be manufactured by the method as given below.

Preparation of Monoclonal Antibody (a) Preparation of Monoclonal Antibody-Producing Cells The protein of the present invention is administered to warm-blooded animals either solely or together with a carrier or a diluent to the site favorable for antibody production. In order to potentiate the antibody productivity upon the administration, complete Freund's adjuvant or incomplete Freund's adjuvant may be administered. The administration is usually carried out once every 2 to 6 weeks and 2 to 10 times in total. Examples of the applicable warm-blooded animals are monkeys, rabbits, dogs, guinea pigs, mice, rats, sheep, goats and fowls. The use of mice or rats is preferred.

In establishing cells which produce monoclonal antibodies, an animal with the detectable antibody titer is selected from animals (e.g. mice) immunized with antigens, then spleen or lymph node is collected after 2 to 5 days from the final immunization and antibody-producing cells contained therein are fused with myeloma cells derived from, homogeneous or heterogeneous animals to obtain monoclonal antibody-producing hybridomas. Measurement of the antibody titer in antisera may, for example, be carried out by reacting a labeled protein, which will be mentioned later, with the antiserum followed by measuring the binding activity of the labeling agent with the antibody. The cell fusion may be carried out, for example, by the method of Koehler and Milstein (Nature, 256, 495, 1975). Examples of the fusion accelerator are polyethylene glycol (PEG), Sendai virus, etc. and the use of PEG is preferred.

Examples of the myeloma cells are those derived from warm-blooded animals such as NS-1, P3U1, SP2/0, AP-1, etc. and the use of P3U1 is preferred. The preferred fusion ratio of the numbers of antibody-producing cells used (spleen cells) to the numbers of myeloma cells is within a range of about 1:1 to 20:1. When PEG (preferably, PEG 1000 to PEG 6000) is added at a concentration of about 10 to 80% followed by incubating at 20 to 40° C., preferably, at 30 to 37° C., for 1 to 10 minutes, an efficient cell fusion can be carried out.

Various methods may be applied for screening a hybridoma which produces a monoclonal antibody. For example, a supernatant of hybridoma culture is added to a solid phase (e.g. microplate) to which the protein antigen is adsorbed either directly or with a carrier, then anti-immunoglobulin antibody (anti-mouse immunoglobulin antibody is used when the cells used for the cell fusion are those of mouse) which is labeled with a radioactive substance, an enzyme or the like, or protein A is added thereto and then monoclonal antibodies bound on the solid phase are detected; or a supernatant of the hybridoma culture is added to the solid phase to which anti-immunoglobulin or protein A is adsorbed, and then the protein labeled with a radioactive substance or an enzyme is added and monoclonal antibodies bound with the solid phase is detected.

Selection and cloning of the monoclonal antibody-producing hybridoma may be carried out by methods per se known to those of skill in the art or methods similar thereto. Usually, it is carried out in a medium for animal cells, containing HAT (hypoxanthine, aminopterin and thymidine). With respect to a medium for the selection, for the cloning and for the growth, any medium may be used so far as hybridoma is able to grow therein. Examples of the medium are an RPMI 1640 medium (Dainippon Pharmaceutical Co., Ltd., Japan) containing 1 to 20% (preferably 10 to 20%) of fetal calf serum (FCS), GIT medium (Wako Pure Chemical, Japan) containing 1 to 20% of fetal calf serum and a suitable serum-free medium for hybridoma (SFM-101; Nissui Seiyaku, Japan). The culture temperature is usually 20 to 40° C. and, preferably, about 37° C. The culture period is usually from five days to three weeks and, preferably, one to two weeks. The culture is usually carried out in 5% carbon dioxide gas. The antibody titer of the supernatant of the hybridoma culture may be measured by the same manner as in the above-mentioned measurement of the antibody titer in the antiserum.

(b) Purification of the Monoclonal Antibody

The separation and purification of the monoclonal antibody may be carried out by methods for separating/purifying immunoglobulin such as salting-out, precipitation with alcohol, isoelectric precipitation, electrophoresis, adsorption/deadsorption using ion exchangers such as DEAE, ultracentrifugation, gel filtration, specific purifying methods in which only an antibody is collected by treatment with an active adsorbent such as an antigen-binding solid phase, protein A or protein G and the bond is dissociated whereupon the antibody is obtained.

Preparation of Polyclonal Antibody

The polyclonal antibody of the present invention can be produced by per se known methods or methods analogous thereto. The method comprises preparing an immunogen (antigen protein) per se or a conjugate of an immunogen with a carrier protein, immunizing a warm-blooded animal in the same manner as described for the production of the monoclonal antibody, harvesting a fraction containing the antibody against the protein of the present invention from the immunized animal, and purifying the harvested antibody.

Referring to the immunogen-carrier protein conjugate for use in the immunization of a warm-blooded animal, the kind of carrier protein and the ratio of the carrier and hapten are not particularly restricted only if the production of the antibody against the hapten conjugated with the particular carrier protein and used for immunization proceeds efficiently. Thus, for example, bovine serum albumin, bovine thyroglobulin, hemocyanine, or the like is coupled in the weight ratio of about 0.1 to 20, preferably about 1 to about 5, to unity of the hapten.

A variety of condensing agents can be used for this coupling between the hapten and the carrier. Thus, for example, a glutaraldehyde, carbodiimide, maleimide, or a thiol or dithiopyridyl group-containing active ester reagent can be employed.

The condensation reaction product is administered to a warm-blooded animal at a site favorable for antibody production, either as it is alone or together with a carrier or diluent. Enhancing antibody production, complete Freund's adjuvant or incomplete Freund's adjuvant may be administered. Administration is carried out generally once in about 2 to 6 weeks for a total of about 3 to 10 times.

The polyclonal antibody can be harvested from the blood, ascites fluid, or other body fluid, preferably from the blood, of the host warm-blooded animal.

The polyclonal antibody titer in the antiserum can be determined in the same manner as the determination of monoclonal antibody described hereinbefore. The separation and purification of the polyclonal antibody can be carried out by the same method as that described for the separation and purification of monoclonal antibody.

The antisense DNA having a nucleotide sequence complementary or substantially complementary to the DNA coding for the protein, the precursor protein or the partial peptide of the present invention (hereinafter referred to as the DNA of the present invention) can be any antisense DNA having a nucleotide sequence complementary or substantially complementary to that of the DNA of the present invention and capable of suppressing expression of the DNA.

The nucleotide sequence substantially complementary to the DNA of the present invention may, for example, be a nucleotide sequence having an identity of not less than about 70%, preferably not less than about 80%, more preferably not less than about 90%, and for still better results, not less than about 95% to the total nucleotide sequence or partial nucleotide sequence of the nucleotide sequence complementary to that the DNA of the present invention. Particularly preferred is an antisense DNA having an identity of not less than about 70%, preferably not less than about 80%, and more preferably not less than about 90%, and for still better results, not less than about 95% to the nucleotide sequence of the domain, of the complete nucleotide sequence complementary to that of the DNA of the present invention, which encodes the N-terminal region of the protein of the present invention (e.g. the nucleotide sequence of the domain around the initiation codon). The antisense DNA can be synthesized using a known DNA synthesis hardware.

The protein, the partial peptide or a salt thereof of the present invention has activities such as a lecithin-cholesterol acyltransferase-like activity and so on, and transfers the β-acyl group (fatty acid) of lecithin (phosphatidylcholine) to the 3β-OH group of cholesterol, so that it consumes the equivalent moles of lecithin and unesterified cholesterol and produces the equivalent moles of cholesteryl ester and lysolecithin.

Uses for the protein, the precursor protein, the partial peptide or a salt thereof (hereinafter sometimes referred to collectively as the protein, etc. of the present invention), the DNA coding for the protein of the present invention (hereinafter sometimes referred to briefly as the DNA of the present invention), the antibody against the protein, the precursor protein, the partial peptide or a salt thereof of the present invention (hereinafter sometimes referred to as the antibody of the present invention), and the antisense DNA of the present invention are now described.

(1) Medicinal Products Such as Drugs for Treating or Preventing Various Diseases As LCAT concerns a cholesterol metabolism, when there is a mutation or deletion on the DNA coding for the LCAT, or a degree of LCAT is decreasing, various diseases (e.g. arteriosclerosis, atherosclerosis, hyperlipidemia, hypercalorism, obesity or hypertriglyceridemia) are arisen from. Therefore, the protein of the present invention etc., and the DNA of the present invention is used for a pharmaceutical agent for treating or preventing arteriosclerosis, atherosclerosis, hyperlipidemia, hypercalorism, obesity, hypertriglyceridemia.

Moreover, the protein of the present invention having LCAT-like activity can be used as a drug for treating or preventing arteriosclerosis, atherosclerosis, hyperlipidemia, obesity, inflammatory diseases, senescence, diseases of brain, and renal disorder.

For example, when there is a patient who is not able to metabolize cholesterol sufficiently or normally in the cell because of a decrease or a defect of LCAT, the role-of the protein of the present invention for said patient can be expected sufficiently or normally by:
(a) administering the DNA coding for the protein, etc. of the present invention to the patient to express it;
(b) inserting the DNA coding for the protein, etc. of the present invention into cells to express it and transplanting the cells to said patient, or (c) administering the protein, etc. of the present invention to the patient.

When the DNA of the present invention is used as the above-mentioned pharmaceutical agent, said DNA may be used alone or after inserting it into a suitable vector such as retrovirus vector, adenovirus vector, adenovirus-associatedvirus vector, pox virus etc. followed by subjecting the product vector to a conventional means. The DNA can also be administered as "naked" DNA, with physiologically acceptable carriers such as adjuvants toassist in uptake, by "gene" gun or by a catheter such as a catheter with a hydrogel.

If one wishes to use the protein, etc. of the present invention, one would use it in a purified form, preferably in a purity of at least 90%, more preferably at least 95%, still more preferably at least 98% and most preferably at least 99%.

For example, the protein, etc. of the present invention can be used orally in the form of tablets which may be sugar coated if necessary, capsules, elixirs, microcapsules etc., or non-orally in the form of injectable preparations such as aseptic solutions and suspensions in water or other pharmaceutically acceptable liquids. These preparations can be produced by mixing the protein, etc. of the present invention with physiologically acceptable carriers, flavoring agents, excipients, vehicles, antiseptics, stabilizers, binders etc. in unit dosage forms required for generally accepted manners of pharmaceutical preparation. Active ingredient contents in these preparations are set so that an appropriate dose within the specified range is obtained.

Additives which can be mixed in tablets, capsules etc. include binders such as gelatin, corn starch, tragacanth and gum arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is the capsule, the above-mentioned materials may further incorporate liquid carriers such as oils and fats. Sterile compositions for injection can be formulated by ordinary methods of pharmaceutical preparation such as by dissolving or suspending active ingredients, naturally occurring vegetable oils such as sesame oil and coconut oil, etc. in vehicles such as water for injection to create pharmaceutical compositions.

Aqueous liquids for injection include physiological saline and isotonic solutions containing glucose and other auxiliary agents, e.g., D-sorbitol, D-mannitol and sodium chloride, and may be used in combination with appropriate dissolution aids such as alcohols, e.g., ethanol, polyalcohols, e.g., propylene glycol and polyethylene glycol, nonionic surfactants, e.g., polysorbate 80™ and HCO-50 etc. Oily liquids include sesame oil and soybean oil, and may be used in combination with dissolution aids such as benzyl benzoate and benzyl alcohol. Furthermore the above-mentioned materials may also be formulated with buffers, e.g., phosphate buffer and sodium acetate buffer; soothing agents, e.g., benzalkonium chloride, procaine hydrochloride; stabilizers, e.g., human serum albumin, polyethylene glycol; preservatives, e.g., benzyl alcohol, phenol; antioxidants etc. Normally, an appropriate ampule is filled in with the thus-prepared pharmaceutical composition such as an injectable liquid.

The vector comprising the DNA of the present invention can be formulated as well as mentioned above, and usually can be used non-orally.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the protein, etc. of the present invention may vary depending on subject disease, subject of administration, way of administration, and so on. When the protein, etc. of the present invention is used, for example, for treating hyperlipidemia by oral administration, the dose of the protein, etc. of the present invention is normally about 0.1 to 100 mg, preferably 1.0 to 50 mg, and more preferably 1.0 to 20 mg per day for an adult human (weighing 60 kg). When the protein, etc. of the present invention is used, for example, for treating hyperlipidemia by non-oral administration, it is advantageous to administer the protein, etc. of the present invention in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject disease and so on. For other animal species, corresponding does as converted per 60 kg weight can be administered.

(2) Screening for Candidate Medicinal Compounds

Since the protein etc. of the present invention has LCAT-like activity, any compound or salt that stimulates the function (e.g. LCAT activity) of the protein etc. of the invention can be used as a pharmaceutical preparation such as a drug for treating or preventing arteriosclerosis, atherosclerosis, hyperlipidemia, atherosclerosis hypercalorism, obesity, hypertriglyceridemia, inflammatory diseases, senescence, diseases of brain, renal disorder and other diseases.

Among them, the protein etc. of the present invention can be used for a drug for treating on preventing arteriosclerosis, atherosclerosis, hyperlipidemia, obesity, inflammatory diseases, senescence, diseases of brain, and renal disorder.

On the other hand, any compound or salt that inhibits the function of the protein etc. of the invention can also be used as a pharmaceutical preparation such as a drug for treating or preventing malnutrition, abetalipoproteinemia, inflammatory diseases, Tangier disease (analphalipoproteinemia), and other diseases.

Therefore, the protein etc. of the present invention is of value as a screening reagent for those compounds and salts which activate or inhibit the function of the protein or equivalent of the present invention.

The present invention, therefore, provides
(1) a screening method for those compounds or salt thereof which stimulate the function (e.g. LCAT-like activity) of the protein, the partial peptide, or a salt thereof of the present invention (hereinafter sometimes referred to briefly as an agonist) or those compounds or a salt thereof which inhibit the function of the protein, the partial peptide or a salt thereof of the present invention (hereinafter sometimes referred to briefly as an antagonist), which comprises using the protein, the partial peptide, or a salt thereof of the invention.

More specifically, the present invention provides
(2) a screening method for said agonist or antagonist, which comprises comparing the case (i) in which the protein, the partial peptide, or a salt thereof of the invention is exposed to lecithin and unesterified cholesterol with (ii) the case in which the protein, the partial peptide, or a salt thereof of the invention is exposed to lecithin, unesterified cholesterol, and a test compound.

Typically, this screening method comprises assaying the LCAT-like activity of the protein etc. of the invention in the above-mentioned cases (i) and (ii) and comparing the results.

For use in the present invention, lecithin may for example be a commercial egg white lecithin (e.g. Sigma).

For use in the present invention, unesterified cholesterol may for example be a [$^{14}$C]-labeled cholesterol (e.g. Amersham).

The screening method according to the present invention is preferably practiced using a proteoliposomal preparation containing such lecithin and unesterified cholesterol. This proteoliposomal preparation contains Apo A-1, [$^{14}$C]-cholesterol, and egg white lecithin in a molar ratio of 0.8:12.5:250.

The test compound that can be used includes but is not limited to peptides, proteins, nonpeptides, synthetic compounds, fermentation products, cell extracts, plant extracts, and animal tissue extracts. Those compounds may be novel compounds or known compounds.

For use in the above screening method, the protein etc. of the present invention is suspended in a suitable screening buffer to prepare a sample of the protein etc. of the invention. The buffer mentioned above may be any buffer solution that does not interfere with the reaction of the protein etc. of the present invention with lecithin and unesterified cholesterol, thus including phosphate buffer and Tris-HCl buffer within the pH range of about 4–10 (preferably pH 6–8).

The LCAT activity of the protein etc. of the present invention can be assayed by the method described in Lipoprotein Analysis (Converse, C. A. and Skinner, R. E. (eds), 1992, IRL Press, Oxford, the chapter authored by Gillet, M. P. T. and Owen, J. S. (pp. 187–201), either as such or as modified.

When a test compound enhanced LCAT activity in case (ii) by not less than about 20%, preferably not less than 30%, more preferably not less than 50%, as compared with case (i), the particular compound can be adopted as an agonist of the LCAT activity of the protein etc. of the invention.

Conversely, when a test compound inhibited LCAT activity in case (ii) by not less than about 20%, preferably not less than about 30%, more preferably not less than about 50%, as compared with case (i), the particular compound can be adopted as an antagonist of the LCAT activity of the protein etc. of the present invention.

The screening kit according to the present invention includes the protein of the invention, a precursor protein or fragment peptide thereof, or a salt of any of them. A typical screening kit according to the present invention is as follows.

[Screening Reagents]
(1) Screening buffer
Tris-HCl buffer (pH 7.4), human serum albumin
(2) Protein sample
The protein, precursor protein, fragment peptide, or salt according to the present invention
(3) Proteoliposomal preparation
[$^{14}$C]-cholesterol ($10^5$ cpm/ml)/Apo A1/[$^{14}$C]cholesterol/egg white lecithin (molar proportions: 0.8:12.5:250)
(4) Detection
Thin-layer chromatography

[Method]
LCAT activity can be assayed by using said solution of the present protein etc. of the invention and said proteoliposomal preparation. Typically, the proteoliposomal preparation can be prepared by mixing Apo A-1, [$^{14}$C]-cholesterol, and egg white lecithin in the molar proportions of 0.8:12.5:250 and incubating the mixture at 37° C. for 30 minutes.

[Protocol]
Incubate the protein solution, the proteoliposomal preparation, and a test compound at 37° C. for 1 hour, isolate the product cholesteryl ester by thin-layer chromatography using hexane/diethyl ether/acetic acid (83:16:1) as developer, and assay. The results can be expressed in nanomoles of free cholesterol esterified per hour.

The compound or salt obtained according to the above screening protocol or by using the above-mentioned screening kit of the invention is a compound (e.g. a member of the class consisting of peptides, proteins, nonpeptides, synthetic compounds,. fermentation products, cell extracts, plant extracts, animal tissue extracts, plasma, etc.) which either activates or inhibits the function (e.g. LCAT-like activity) of the protein etc. of the present invention.

As the salt of such a compound, the same kind of salt as the salt of the protein of the invention, mentioned-above can be used.

The compound which activates the function (e.g. LCAT-like activity) of the protein etc. of the present invention can be used as a drug, e.g. a drug for treating or preventing arteriosclerosis, atherosclerosis, atherosclerosis hyperlipidemia, hypercalorism, obesity, hypertriglyceridemia, inflammatory diseases, senescence, diseases of brain, renal disorder and other diseases.

Among them the protein etc. of the present invention can be used for a drug for treating on preventing arteriosclerosis, atherosclerosis, hyperlipidemia, obesity, senescence, diseases of brain, and renal disorder.

On the other hand, the compound which inhibits the function of the protein or equivalent of the invention can be used as a drug, e.g. a drug for treating or preventing malnutrition, abetalipoproteinemia, inflammatory diseases, Tangier disease, and other diseases.

When the compound obtained by the screening method of the present invention or by using the screening kit of the present invention is used as agent for treating or preventing the diseases mentioned above, it can be formulated to tablets, capsules, slixirs, microcapsules, aseptic solution, suspensions or the like in the same way as the pharmaceutical composition comprising the protein, etc. of the present invention as mentioned above.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the protein, etc. of the present invention may vary depending on subject disease, subject of administration, and so on. When the compound which promotes the function of the protein of the present invention (e.g. LCAT-like activity, etc.) is used, for example, for treating hyperlipidemia by oral administration, the dose of the compound is normally about 0.1 to 100 mg, preferably 1.0 to 50 mg, and more preferably 1.0 to 20 mg per day for an adult human (weighing 60 kg). When the compound which promotes the function of the protein of the present invention (e.g. LCAT-like activity, etc.) is used, for example, for treating hyperlipidemia by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject disease and so on. For other animal species, corresponding doses as converted per 60 kg weight can be administered.

When the compound which inhibits the function of the protein of the present invention (e.g. LCAT-like activity, etc.) is used, for example, for treating abetalipoproteinemia by oral administration, the dose of the compound is normally about 0.1 to 100 mg, preferably 1.0 to 50 mg, and more preferably 1.0 to 20 mg per day for an adult human (weighing 60 kg). When the compound which inhibits the function of the protein of the present invention (e.g. LCAT-like activity, etc.) is used, for example, for treating abetalipoproteinemia by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject disease and so on. For other animal species, corresponding does as converted per 60 kg weight can be administered.

(3) Quantitative Determination of the Protein of the Present Invention

The antibody of the present invention is capable of specifically recognizing the protein, etc. of the present invention and, accordingly, it can be used for quantitative determination of the protein, etc. of the present invention in test liquid samples and particularly for quantitative determination by sandwich immunoassays.

Thus, the present invention provides, for example, the following methods:

(i) a quantitative determination of the protein, etc. of the present invention in a test liquid sample, which comprises
(a) competitively reacting the test liquid sample and a labeled protein, etc. of the present invention with the antibody of the present invention, and
(b) measuring the ratio of the labeled protein, etc. of the present invention binding with said antibody; and
(ii) a quantitative determination of the protein, etc. of the present invention in a test liquid sample, which comprises
(a) reacting the test liquid sample with an antibody immobilized on an insoluble carrier and a labeled antibody simultaneously or continuously, and (b) measuring the activity of the labeling agent on the insoluble carrier, wherein one antibody is capable of recognizing the N-terminal region of the protein, etc. of the present invention while another antibody is capable of recognizing the C-terminal region of the protein, etc. of the present invention.

When the monoclonal antibody of the present invention recognizing a protein, etc. of the present invention (hereinafter, sometimes referred to as "monoclonal antibody of the present invention") is used, the quantity of the protein, etc. of the present invention can be measured and, moreover, the protein, etc. of the present invention can be detected by means of a tissue staining, etc. as well. For such an object, antibody molecules per se may be used, or $F(ab')_2$ Fab' or Fab fractions of the antibody molecule may also be used.

There is no particular limitation for the measuring method using the antibody of the present invention and any measuring method may be used so far as it relates to a method in which the amount of antibody, antigen or antibody-antigen complex, depending on or corresponding to the amount of antigen, e.g. the amount of the protein, etc. of the present invention in the liquid sample to be measured, is detected by a chemical or a physical means and then calculated using a standard curve prepared by a standard solution containing the known amount of antigen. For example, nephrometry, competitive method, immunometric method and sandwich method are suitably used and, in terms of sensitivity and specificity, the sandwich method which will be described herein later is particularly preferred.

Examples of the labeling agent used in the measuring method using the labeling substance are radioisotopes, enzymes, fluorescent substances, luminescent substances, colloids, magnetic substances, etc. Examples of the radioisotope are [$^{125}$I], [$^{131}$I], [$^3$H] and [$^{14}$C]. Preferred examples of the enzyme are those which are stable and with much specific activity, such as β-galactosidase, β-glucosidase, alkaline phosphatase, peroxidase and malate dehydrogenase. Examples of the fluorescent substance are fluorescamine, fluorescein isothiocyanate, etc. Examples of the luminescent substance are luminol, luminol derivatives, luciferin, lucigenin, etc. Further, a biotin-avidin system may also be used for binding an antibody or antigen with a labeling agent.

In insolubilization (immobilization) of antigens or antibodies, a physical adsorption may be used or a chemical binding which is usually used for insolubilization or immobilization of proteins or enzymes may be used as well. Examples of the carrier are insoluble polysaccharides such as agarose, dextran and cellulose; synthetic resins such as polystyrene, polyacrylamide and silicone; glass; etc.

In a sandwich method, the test liquid is allowed to react with an insolubilized monoclonal antibody of the present invention (the first reaction), then it is allowed to react with another labeled monoclonal antibody of the present invention (the second reaction) and the activity of the labeling agent on the insoluble carrier is measured whereupon the amount of the protein, etc. of the present invention in the test liquid can be determined. The first reaction and the second reaction may be conducted reversibly or simultaneously or they may be conducted with an interval. The type of the labeling agent and the method of insolubilization may be the same as those mentioned hereinbefore. In the immunoassay by means of a sandwich method, it is not always necessary that the antibody used for the labeled antibody and the antibody for the solid phase is one type or one species but, with an object of improving the measuring sensitivity, etc., a combination of two or more antibodies may be used as well.

In the method of measuring the protein, etc. of the present invention by the sandwich method of the present invention, the preferred monoclonal antibodies of the present invention used for the first and the second reactions are antibodies wherein their sites binding to the protein of the present invention are different from each other. Thus, antibodies used in the first and the second reactions are those wherein, when an antibody used in the second reaction recognizes the C-terminal region of the protein, etc. of the present invention, then another antibody recognizing the site other than C-terminal regions, e.g. recognizing the N-terminal region, is preferably used in the first reaction.

The monoclonal antibody of the present invention may be used in a measuring system other than the sandwich method such as a competitive method, an immunometric method and a nephrometry.

In the competitive method, an antigen in the test solution and a labeled antigen are allowed to react with an antibody in a competitive manner, then an unreacted labeled antigen (F) and a labeled antigen (B) binding with an antibody are separated (i.e. B/F separation) and the labeled amount of any of B and F is measured whereupon the amount of the antigen in the test solution is determined. With respect to the method for such a reaction, there are a liquid phase method in which a soluble antibody is used as the antibody and the B/F separation is conducted by polyethylene glycol, a second antibody to the above-mentioned antibody, etc.; and a solid phase method in which an immobilized antibody is used as the first antibody or a soluble antibody is used as the first antibody while an immobilized antibody is used as the second antibody.

In the immunometric method, an antigen in the test solution and an immobilized antigen are subjected to a competitive reaction with a certain amount of a labeled antibody followed by separation into solid and liquid phases or the antigen in the test solution and an excess amount of labeled antibody are allowed to react, then an immobilized antigen is added to bind an unreacted labeled antibody with the solid phase and separated into solid and liquid phases. After that, the labeled amount of any of the phases is measured to determine the antigen amount in the test solution.

In the nephrometry, the amount of insoluble sediment which is produced as a result of the antigen-antibody reaction in a gel or in a solution is measured. Even when the antigen amount in the test solution is small and only a small amount of the sediment is obtained, a laser nephrometry wherein scattering of laser is utilized can be suitably used.

In applying each of those immunological measuring methods (immunoassays) to the measuring method of the present invention, it is not necessary to set up any special condition, operation, etc. therefor. A measuring system (assay system) for the protein of the present invention may be constructed taking the technical consideration of the persons skilled in the art into consideration in the conventional conditions and operations for each of the methods. With details of those conventional technical means, a variety of reviews, reference books, etc. may be referred to.

They are, for example, Hiroshi Irie (ed): "Radioimmunoassay" (Kodansha, Japan, 1974); Hiroshi Irie (ed): "Radioimmunoassay; Second Series" (Kodansha, Japan, 1979); Eiji Ishikawa et al. (ed): "Enzyme Immunoassay" (Igaku Shoin, Japan, 1978); Eiji Ishikawa et al. (ed): "Enzyme Immunoassay" (Second Edition) (Igaku Shoin, Japan, 1982); Eiji Ishikawa et al. (ed): "Enzyme Immunoassay" (Third Edition) (Igaku Shoin, Japan, 1987); "Methods in Enzymology" Vol. 70 (Immunochemical Techniques (Part A)); ibid. Vo. 73 (Immunochemical Techniques (Part B)); ibid. Vo. 74 (Immunochemical Techniques (Part C)); ibid. Vo. 84 (Immunochemical Techniques (Part D: Selected Immunoassays)); ibid. Vol. 92 (Immunochemical Techniques (Part E: Monoclonal Antibodies and General Immunoassay Methods)); ibid. Vol. 121 (Immunochemical Techniques (Part I: Hybridoma Technology and Monoclonal Antibodies)) (Academic Press); etc.

By using the antibody of the present invention in the above manner, the protein of the present invention can be assayed with high sensitivity.

In addition, when decrease in concentration of the protein, etc. of the present invention is detected by determining the concentration of the protein, etc. of the present invention by using the antibody against the protein of the present invention, it may lead, with high probability, to the diagnosis of various diseases such as arteriosclerosis, atherosclerosis, hyperlipidemia, hypercalorism, obesity, hypertriglyceridemia, inflammatory diseases, senescence, diseases of brain, renal disorder and so on.

When increase in concentration of the protein, etc. of the present invention is detected, it may lead, with high probability, to the diagnosis of various diseases such as malnutrition, abetalipoproteinemia or Tangier disease and so on.

Thus, the antibody of the present invention is useful as a diagnostic agent for the above-mentioned diseases.

Furthermore, the antibody of the present invention can be used for the purpose of detecting the protein of the present invention which may be present in test samples such as body fluids or tissues. The antibody can also be used for the construction of an antibody column for purification of the protein of the present invention, detection of the protein of the present invention in the fractions in the course of purification, and analysis of the behavior of the protein of the present invention in the test cell.

(4) Gene Diagnostic Agent

By using the DNA of the present invention as a probe, for instance, an abnormality (gene abnormality) of the DNA or mRNA coding for the protein of the present invention or its partial peptide in humans or mammals (e.g. rat, mouse, guinea pig, rabbit, sheep, swine, bovine, horse, cat, dog, monkey, chimpanzee, etc.) can be detected. Therefore, the DNA of the present invention is useful as a gene diagnostic agent for the damage to the DNA or mRNA, mutation thereof, or decreased expression thereof, or increased expression or over expression of the DNA or mRNA.

For example, when the increase of the mRNA coding for the protein, etc. or the increase of the protein, etc. of the present invention is detected, it may be lead to the diagnosis of malnutrition, abetalipoproteinemia or Tangier disease, etc.

On the other hand, the deficit or lack of the DNA or mRNA or the decrease of the protein, or a mutation of the DNA is detected by the PCR-SSCP assay etc. is detected, it may be lead to the diagnosis of arteriosclerosis, atherosclerosis, hyperlipidemia, hypercalorism, obesity, hypertriglyceridemia, inflammatory diseases, senescence, diseases of brain, renal disorder, etc.

The above-mentioned gene diagnosis using the DNA of the present invention can be carried out by, for example, the per se known Northern hybridization assay or PCR-SSCP assay (Genomics, 5, 874–879 (1989); Proceedings of the National Academy of Sciences of the United States of America, 86, 2766–2770 (1989)).

When increase in expression of the mRNA coding for the protein, etc. of the present invention is detected by Northern hybridization assay, it may lead, with high probability, to the diagnosis of malnutrition, abetalipoproteinemia or Tangier disease, etc.

When decrease in expression of the mRNA or a mutation of the DNA is detected by the PCR-SSCP assay is detected it may lead, with high probability, to the diagnosis of arteriosclerosis, atherosclerosis, hyperlipidemia, hypercalorism, obesity, hypertriglyceridemia, etc.

(5) Pharmaceutical Composition Containing the Antisense DNA

The antisense DNA which is capable of complementarily binding to the DNA coding for the protein, etc. of the present invention and suppresses the expression of the DNA and the protein, etc. of the present invention is capable of inhibiting the function of the protein, etc. or the DNA coding for the protein, etc. of the present invention which show the above-mentioned activities in vivo. Therefore, this antisense DNA is used for an agent for treating or preventing various diseases such as malnutrition, abetalipoproteinemia or Tangier disease, etc.

When the antisense DNA is used for the agent for treating or preventing the diseases mentioned above, it can be formulated in the same way as the composition for treating or preventing the disease mentioned above containing the DNA of the present invention.

The DNA may be used alone or after inserting it into a suitable vector such as retrovirus vector, adenovirus vector, adenovirus-associated virus vector, pox virus etc. followed by subjecting the product vector to a conventional means. The DNA can be administered as "naked" DNA, or with physiologically acceptable carriers such as adjuvants to assist in uptake, by "gene" gun or by a catheter such as a catheter with a hydrogel.

In addition, this antisense DNA can be used as a diagnostic oligonucleotide probe for investigating the presence of the DNA of the present invention or the status of its expression in various tissues and cells.

(6) Pharmaceutical Compositions Containing the Antibody of the Present Invention Of the antibody according to the present invention, those species which neutralize the activity of the protein, etc. of the present invention can be used as drugs, such as an agent for treating or preventing diseases such as malnutrition, abetalipoproteinemia or Tangier disease, etc.

The above-mentioned composition for treating or preventing the diseases mentioned above containing the antibody of the present invention can be administered either orally or otherwise to human and other mammals (e.g. rat, rabbit, sheep, swine, cattle, cat, dog, monkey), in the form of an antibody solution as such or in the form of a pharmaceutical composition having an appropriate dosage form.

The dosage is dependent on the recipient, target disease, symptom, administration route, and other factors. Generally, however, for treating or preventing abetalipoproteinemia in a human adult, for instance, the antibody capable of neutralizing the activity of the protein, etc. of the present invention can be administered, by the intravenous route, in a single dose of about 0.01 to 20 mg/kg body weight, preferably 0.1 to 10 mg/kg body weight, or more preferably about 0.1 to 5 mg/kg body weight, about 1 to 5 times a day, or preferably about 1 to 3 times a day. For administration by other routes and for oral administration, the dosage can be selected using the above dosage schedule as a reference. In case of presenting with particularly severe symptoms, the dosage may be increased according to the condition.

The antibody of the present invention which neutralizes the activity of the protein, etc. of the present invention can be administered either as it is or in the form of a suitable pharmaceutical composition. The pharmaceutical composition comprises the antibody or its salt and a pharmaceutically acceptable carrier, diluent, or excipient. The composition can be provided in various dosage forms suited for oral administration or non-oral administration.

The composition for oral administration, for instance, includes solid and liquid dosage forms such as tablets (including dragees, film-coated tablets), pills, granules, powders, capsules (including soft capsules), syrup, emulsion, suspension, etc. Such dosage forms can be manufactured by the per se known procedures and contain a carrier, diluent or excipient which is generally included in pharmaceutical formulations. The carrier or excipient for tablets includes but is not limited to lactose, starch, sucrose, and magnesium stearate.

The composition for non-oral administration may for example be an injectable product or a suppository. The injectable product includes intravenous, subcutaneous, intradermal, intramuscular, drip, and other injections. Such injections can be prepared by the per se known procedures, for example by dissolving, suspending, or emulsifying the antibody or salt in a sterile aqueous or oily vehicle which is generally used in the manufacture of injectable products. The aqueous vehicle for injections includes physiological saline and various isotonic solutions containing glucose and/or the like and may be supplemented with a suitable solubilizer such as alcohols (e.g. ethanol), polyols (e.g. propylene glycol, polyethylene glycol), nonionic surfactants [polysorbate 80, HCO-50 (polyoxyethylene(50 mol)-hydrogenated castor oil adduct)], etc. The oily vehicle includes but is not limited to sesame oil and soybean oil. Benzyl benzoate, benzyl alcohol, etc. may also be used as solubilizers. Injections thus prepared are provided as filled in suitable ampules. Suppositories for rectal administration can be manufactured by mixing said antibody or salt with any of the conventional suppository bases.

The above pharmaceutical composition for oral or non-oral administration can be conveniently provided in unit dosage forms suited for delivery of the unit dose of the active ingredient. The unit dosage form may for example be the above-mentioned tablet, pill, capsule, injection (ampule) or suppository. Preferably, the amount of said antibody or salt per unit dosage form is generally 5–500 mg and preferably 5–100 mg for injectable products or 10–250 mg for other products.

The foregoing composition may contain other active ingredients unless their formulation with said antibody or salt results in unfavorable interactions.

(7) Construction of a Transgenic Animal

The present invention further provides a non-human mammal harboring a foreign DNA coding for the protein of the present invention (hereinafter referred to briefly as foreign DNA) or a mutant thereof (sometimes referred to briefly as a foreign mutant DNA).

Thus, the present invention provides
(1) a non-human mammal harboring a foreign DNA of the present invention or a foreign mutant DNA thereof:
(2) the non-human mammal according to (1) which is a rodent:
(3) the non-human mammalian according to (2) wherein the rodent is a mouse; and
(4) a recombinant vector containing the foreign DNA of the present invention or a foreign mutant DNA thereof and capable of being expressed in a mammal.

The non-human mammal harboring the foreign DNA of the present invention or a foreign mutant DNA thereof (hereinafter referred to briefly as the transgenic animal of the present invention) can be constructed by transferring the objective DNA to a germinal cell such as an unfertilized egg cell, fertilized egg cell, or sperm cell or its primordial cell, preferably in the period of embryogenesis in the ontogenesis of a non-human mammal (more preferably in the stage of a single cell or a fertilized egg cell and generally at the 8-cell stage or earlier), by the calcium phosphate method, electric pulse method, lipofection method, agglutination method, microinjection method, particle gun method, or DEAE-dextran method.

The non-human mammal used includes bovine, swine, sheep, goat, rabbit, canine, feline, guinea pig, hamster, murine, rat, and so on. From the standpoint of construction of a diseased animal model, rodents which have comparatively short ontogenesis and life cycles and can be easily bred, particularly mice (e.g. pure strains such as C57BL/6, DBA2, etc. and hybrid strains such as B6C3F1, BDF1, B6D2F1, BALB/c, ICR, etc.) or rats (e.g. Wistar, SD, etc.) are preferred.

The "mammal" as mentioned with reference to the recombinant vector capable of being expressed in a mammal includes the same non-human mammals as those mentioned above and humans.

The mutant DNA includes not only the DNAs available upon variation (e.g. mutation) of the nucleotide sequence of the original DNA of the present invention, for example, upon addition or deletion of nucleotide sequence or substitution of other, and includes abnormal DNAs.

The term "abnormal DNA" as used herein means any DNA that causes an expression of an abnormal protein of the present invention, for example, an expression of a protein which suppresses the function of the normal protein of the present invention.

The foreign DNA of the present invention may be one derived from a mammal of the same species as the host animal or a mammal of a different species. For transfer of the DNA of the present invention to the host animal, it is generally advantageous to use a DNA construct prepared by linking the DNA at downstream of a promoter capable of being expressed in animal cells. For example, in transferring the human-derived DNA of the present invention, this human DNA of the present invention can be linked at downstream of a promoter capable of causing expression of DNAs derived from various animals (e.g. rabbit, canine, feline, guinea pig, hamster, rat, murine, etc.) harboring the DNA of the present invention having high homology thereto to prepare a DNA construct (e.g. a vector) which can then be microinjected into the fertilized egg cell of a host mammal such as a fertilized murine egg cell, whereby a transgenic mammal showing a high expression of the DNA of the present invention can be provided.

Examples of the expression vector used for the protein of the present invention are plasmids derived from *E. coli*, plasmids derived from *B. subtilis*, plasmids of the yeast origin, λ phage and other bacteriophages, retroviruses such as Molony leukemia virus, and animal viruses such as vaccinia virus and vaculovirus. Preferable examples are plasmids of the *E. coli* origin, plasmids of the *B. subtilis* origin, and yeast-derived plasmids.

The promoter for the regulation of the expression of the DNA are (1) promoters for DNAs derived from viruses (e.g. simian virus, cytomegalovirus, Molony leukemia virus, JC virus, papilloma virus, poliovirus, etc.), (2) promoters derived from mammals (e.g. man, rabbit, dog, cat, guinea pig, hamster, rat, mouse, etc.) for albumin, insulin II, uroprakin II, elastase, erythropoietin, endothelin, muscle creatine kinase, glial fibrillary acidic protein, glutathione S-transferase, platelet-derived growth factor α, keratin K1, K10, and K14, collagen type I and type II, cyclic AMP-dependent protein kinase βI subunit, dystrophin, tartaric acid-resistant alkaline phosphatase, atrial natriuretic factor, endothelial receptor tyrosine kinase (generally abbreviated as Tie2), sodium/potassium-exchanging adenosinetriphosphatase (Na, K-ATPase), neurofilament light chain, metallothionein I and IIA, metalloprotease I tissue inhibitor, MHC Class I antigen (H-2L), H-ras, renin, dopamine β-hydroxylase, thyroid peroxidase (TPO), poly-peptide chain elongation factor 1α (EF-1α), βactin, α- and β-myosin heavy chain, myosin light chains 1 and 2, myelin basic protein, thyroglobulin, Thy-1, immunoglobulin H chain variable region (VNP), serum amyloid P component, myoglobin, troponin C, smooth muscle -α actin, preproenkephalin A or vasopressin, and so on. Preferable promoters are promoters conducive to high expression in the whole body, such as cytomegalovirus promoter, human polypeptide chain elongation factor 1α (EF-1α) promoter, and human and chicken β-actin promoters.

The vector preferably has a sequence for terminating the transcription of the objective mRNA (generally called terminator) in the transgenic mammal. The examples of the sequence are sequences derived from viruses, various mammals. Preferable examples are the SV40 terminator derived from simian virus, and so on.

In addition, for enhancing the expression of the objective DNA, it is possible, depending on the specific objective, to link the splicing signal, enhancer domain, a portion of the eucaryotic DNA intron, etc. at upstream of the 5'-end of the promoter region, between the promoter region and the translated region, or at downstream of the 3'-end of the translated region.

The translated region of the normal protein of the present invention can be obtained, as the whole or part of the genomic DNA, from the DNAs derived from the liver, kidney, or thyroid cells or fibroblasts of various mammals (e.g. rabbit, canine, feline, guinea pig, hamster, rat, murine, man, etc.) or from various commercial genomic DNA libraries, or starting with the complementary DNAs prepared from RNAs derived from the liver, kidney, thyroid cells or fibroblasts by the known technique. The foreign abnormal DNA can be constructed by mutating the translated region of the normal protein obtained from the above-mentioned cells or tissues by the mutagenesis method.

The translated region can be prepared as a DNA construct which can be expressed in a transgenic animal, by the routine recombinant DNA technique, i.e. by coupling it at downstream of the promoter and, if desired, at upstream of the transcription termination site.

The transfer of the DNA of the present invention at the fertilized egg cell stage insures that the DNA will be ubiquitous in all the germ cells and somatic cells of the host mammal. The presence of the DNA of the present invention in the germ cells of the transgenic animal following DNA transfer means that all the germ cells and somatic cells of all the progeny of the transgenic animal harbor the DNA of the present invention. Thus, the offspring of animals of this line to which DNA is passed down have the DNA of the present invention in their germ cells and somatic cells.

The non-human mammal to which the foreign normal DNA of the present invention has been transferred can be verified by mating to retain the DNA stably and then bred as a strain harboring the transferred DNA from generation to generation under the usual breeding conditions. The transfer of the DNA of the present invention in the fertilized egg cell stage is carried out in such a manner that the transferred DNA will be present in excess in all the germ cells and somatic cells of the transgenic animal. The presence of an excess of the DNA of the present invention in the germ cells of the transgenic animal means that all the progeny of this line harbor an excess of the DNA of the present invention in their germ cells and somatic cells. By preparing homozygous animals having the transferred DNA in both homologous chromosomes and mating the animals of both sexes, they can be bred serially so that all the progeny may harbor an excess of the DNA.

The non-human mammal harboring the normal DNA of the present invention features a high expression of the DNA and may eventually develop a hyperergasia of the protein of the present invention through activation of the function of the endogenous normal DNA and, therefore, can be utilized as an animal model of the disease. For example, by using the transgenic animal harboring the normal DNA of the present invention, it is possible to study the hyperergasia of the protein of the present invention to elucidate the mechanisms of diseases with which the protein of the present invention is associated, and explore therapeutic modalities for the diseases.

Furthermore, the mammal to which the foreign normal DNA of the present invention has been transferred presents with symptoms due to an increase in the free protein of the present invention and, therefore, can also be used in the screening of therapeutic drugs for diseases with which the protein of the present invention is associated.

On the other hand, the non-human mammal harboring the foreign abnormal DNA of the present invention can be verified by mating to retain the DNA stably and then bred as a line harboring the DNA from generation to generation under the usual breeding conditions.

Moreover, it is possible to incorporate the objective DNA in the above-mentioned plasmid for use as a starting material. The DNA construct with the promoter can be prepared by the routine recombinant DNA technique. Transfer of the abnormal DNA of the present invention in the fertilized egg cell stage insures that the transferred DNA will be ubiquitous in all the germ cells and somatic cells of the host mammal. The presence of the abnormal DNA of the present invention in the germ cells of the transgenic animal means that all the offspring of this transgenic animal harbor the abnormal DNA of the present invention in all of their germ cells and somatic cells. The progeny of this animal harbor the abnormal DNA of the present invention in all of their germ cells and somatic cells. By preparing homozygous male and female animals having the introduced DNA in both homologous chromosomes and mating them, it can be insured that all their offsprings harbor the DNA.

The non-human mammal harboring the abnormal DNA of the present invention features a high expression of the abnormal DNA and, therefore, may eventually develop adiaphoria associated with functional inactivation of the protein of the present invention through inhibition of the function of the endogenous normal DNA and, therefore, can be utilized as an animal model of the disease. For example, by using the transgenic animal harboring the abnormal DNA of the present invention, analysis of the mechanism of this functional inactivation adiaphoria due to the protein of the present invention and therapeutic modalities for the disease can be explored.

As a specific potential use, the transgenic animal with a high expression of the abnormal DNA of the present invention can be used as a model for elucidating the functional inhibition of the normal protein by the abnormal protein of the present invention (dominant negative effect) in adiaphoria of functional inactivation type due to the protein of the present invention. Moreover, the transgenic mammal harboring the foreign abnormal DNA of the present invention develops symptoms due to an increase in the free protein of the present invention and, therefore, can be utilized in the screening of therapeutic compounds for functional inactivation of the protein of the present invention.

As other potential uses for transgenic animals harboring the two kinds of DNAs described above, the following uses can be suggested.

(1) Use as a cell source for tissue culture;
(2) Analysis of the relationship of the protein of the present invention to proteins which are specifically expressed or activated by the protein by direct analysis of DNAs or RNAs in the tissues of the transgenic mammal harboring the DNA of the present invention or analysis of the composition of the protein expressed by the DNA;
(3) Study of the functions of cells of those tissues which are generally difficult to culture by using the cells from the tissues containing the DNA as cultured by the standard tissue culture technique;
(4) Screening of drugs capable of enhancing the cell functions by using the cells described in (3);
(5) Isolation and purification of the muteins of the present invention and construction of antibodies to the muteins.

Furthermore, by using the transgenic animal of the present invention, clinical symptoms of diseases associated with the protein of the present invention, inclusive of said functional inactivation of the protein of the present invention, can be investigated. In addition, more detailed pathological findings can be generated in various organs of this model of diseases associated with the protein of the present invention, thus contributing to the development of new therapies and the study and treatment of secondary diseases arising from such diseases.

Moreover, following isolation of various organs from the transgenic animal of the present invention and their mincing and digestion with a proteolytic enzyme such as trypsin, free single cells harboring the transferred gene can be recovered and cultured for establishment of a cell line. Furthermore, characterization of cells producing the protein of the present invention can be made and their relationship to apotosis, differentiation, or proliferation, the mechanism of signal transduction in them, and abnormalities involved can be explored to thereby generate information useful for a further elucidation of the protein of the present invention and its actions.

Moreover, for the development of therapeutic drugs for diseases associated with the protein of the present invention, such as functional inactivation of the protein of the present invention by using the transgenic animal of the present invention, an effective and rapid screening technology for such therapeutic drugs can be established by using the test and assay methods described hereinbefore. In addition, by using the above transgenic animal or the foreign DNA expression vector of the present invention, gene therapies for diseases associated with the protein of the present invention can be explored and developed.

(8) Construction of Knockout Animals

The present invention further provides a non-human mammalian embryonic stem cell wherein the DNA of the present invention is inactivated and a non-human mammal deficient in expression of the DNA of the present invention wherein the DNA is inactivated.

The present invention, therefore, provides:
(1) a non-human mammalian embryonic stem cell wherein the DNA of the present invention is inactivated;
(2) the non-human mammalian embryonic stem cell according to (1) wherein the DNA is inactivated by introduction of a reporter gene (e.g. a β-galactosidase gene of the *E. coli* origin);
(3) the non-human mammalian embryonic stem cell according to (1) which is neomycin-resistant;
(4) the non-human mammalian embryonic stem cell according to (1) wherein the non-human mammal is a rodent;
(5) the non-human mammalian embryonic stem cell according to (4) wherein the rodent is a mouse;
(6) a non-human mammal deficient in expression of the DNA of the present invention, wherein the DNA is inactivated;
(7) the non-human mammal according to (6) wherein the DNA is inactivated by introduction of a reporter gene (e.g. a β-galactosidase gene of *E. coli* origin) and the reporter gene can be expressed under the control of the promoter against the DNA of the present invention;
(8) the non-human mammal according to (6) wherein the non-human mammal is a rodent;
(9) the non-human mammal according to (8) wherein the rodent is a mouse; and
(10) a method for screening for a compound or a salt thereof which enhances or inhibits an activity of the promoter against the DNA of the present invention, which comprises administering a test compound to the non-human mammal according to (7) and detecting an expression of the reporter gene.

The term "non-human mammalian embryonic stem cell wherein the DNA of the present invention in inactivated" means the embryonic stem cell (hereinafter referred to briefly as ES cell) of a non-human mammal in which the DNA has been deprived of the capacity to express the protein of the present invention (hereinafter referred to sometimes as the knockout DNA of the present invention) through introduction of an artificial mutation to the DNA of the present invention possessed by the non-human mammal to thereby inhibit expression of the DNA of the present invention or through substantial deprivation of the activity of the protein of the present invention which is encoded by the DNA.

The non-human mammal includes the same animals mentioned hereinbefore.

Examples of the method for introducing an artificial mutation to the DNA of the present invention are a deletion of some or all of the DNA sequence, or an insertion or substitution of a different DNA by the genetic engineering technology. By such a mutation, the codon reading frame can be shifted or the function of the promoter or exon can be disrupted to provide the knockout DNA of the present invention.

The non-human mammalian embryonic stem cell wherein the DNA of the present invention is inactivated (hereinafter referred to as the ES cell wherein the DNA is the inactivated of the present invention or the knockout ES cell of the present invention) can be prepared by, for example, a procedure which comprises isolating the DNA of the present invention from an objective non-human mammal, inserting a drug-resistance gene, typically the neomycin-resistance gene or hygromycin-resistance gene, or a reporter gene such as lacZ (β-galactosidase gene) or cat (chloramphenicol acetyltransferase gene) in its exon region to disrupt the function of the exon or inserting a DNA sequence for terminating gene transcription (e.g. poly A coupling signal) in the intron region between exons to thereby inhibit synthesis of a complete mRNA, introducing the thus-constructed DNA chain having a DNA sequence adapted to eventually disrupt the gene (hereinafter referred to briefly as the targeting vector) into the chromosomes of the host animal by homologous recombination, subjecting the resulting ES cell to Southern hybridization analysis using the DNA sequence on the DNA of the present invention or in its vicinity as the probe or a PCR procedure using the DNA sequence on the targeting vector and a DNA sequence in the vicinity but not including the DNA of the present invention used in the construction of the targeting vector as primers, and selecting the knockout ES cell of the present invention.

Moreover, the original ES cell used for inactivation of the DNA of the present invention by the homologous recombination technique or the like may be an already established cell line such as those mentioned hereinbefore or a new cell line established de novo by the known method of Evans and Kaufma. Taking murine ES cells as an example, ES cells of the 129 line are generally employed but the immunological background of this line is not clear. Therefore, the cell line established by using BDF1 mice created by the hybridization of C57BL/6 mice and C57BL/6 mice, both yielding few eggs, with DBA/2 mice (BDF1=F1 of C57BL/6 and DBA/2) for preparing pure-line ES cells with an immunologically defined genetic background can be used with advantage. In addition to the advantage of high egg output and sturdiness of the egg, BDF1 mice have the background of C57BL/6 mice so that in the construction of a disease model with ES cells obtained, the genetic background of the model mice can be converted to that of C57BL/6 mice by back-crossing with C57BL/6.

Moreover, in establishing an ES cell line, it is common practice to use blastocytes 3.5 days following fertilization but, aside from them, a large number of early embryos can be prepared with high efficiency by harvesting the embryos at the 8-cell stage and culturing them into blastocytes.

Furthermore, while ES cells from both male and female animals can be employed, generally ES cells of a male animal are more convenient for the construction of reproduction line chimeras. Moreover, for the purpose of reducing the burden of the complicated cultural procedure, it is preferable to carry out sexing as early as possible.

As a typical method for sexing ES cells, there can be mentioned the method in which the gene in the sex determination region on the Y chromosome is amplified and detected by PCR. Whereas the conventional karyotype analysis requires about $10^6$ cells, the above method requires only about one colony equivalent of ES cells (about 50 cells). Therefore, the primary selection of ES cells in an early stage can be made by this sexing method. Since male cells can thus be selected in the early stage, the trouble in the initial stage of culture can be drastically reduced.

Moreover, the secondary selection can be carried out by G-banding for the number of chromosomes. The number of chromosomes in the resulting ES cell is preferably 100% of the normal number but this goal may not be reached due to the physical and other factors involved in the establishment of the line. In such cases, it is preferable to knockout the gene of the ES cell and reclone it in the normal cell (taking a mouse as an example, the cell in which the number of chromosomes is 2n=40).

The embryonic stem cell line thus established is generally very satisfactory in proliferation characteristic but since it is liable to lose its ontogenic ability, it must be subcultured with sufficient care. For example, this cell line should be cultured on suitable feeder cells such as STO fibroblasts in the presence of LIF (1–10000 U/ml) in a carbon dioxide incubator (preferably 5% $CO_2$-95% air or 5% oxygen-5% $CO_2$-90% air) at about 37° C. and, in subculture, it should be treated with trypsin/EDTA solution. (generally 0.001–0.5% trypsin/0.1–5 mM EDTA, preferably about 0.1% trypsin/1 mM EDTA) to provide single cells and seed them on freshly prepared feeder cells. While such subculture is generally performed every 1–3 days, it is good practice to observe the cells on each occasion and, whenever morphologically abnormal cells are discovered, discard the culture.

ES cells can be allowed to differentiate into various types of cells, such as head long muscle cells, visceral muscle cells, heart muscle cells, etc. by conducting monolayer culture to a high density under suitable conditions or suspension culture until a mass of cells is formed (M. J. Evans & M. H. Kaufman, Nature, 292, 154, 1981; G. R. Martin, Proceedings of National Academy of Science USA, 78, 7634, 1981; T. C. Doetschman et al., Journal of Embryology and Experimental Morphology, 87, 27, 1985), and the cell deficient in expression of the DNA of the present invention as obtained by causing the ES cell of the present invention to differentiate is useful for the cytobiological in vitro study of the protein of the present invention.

The non-human mammal deficient in expression of the DNA of the present invention can be differentiated from the normal animal by assaying the mRNA in the animals by the known method and comparing the amounts of expression indirectly.

The non-human mammal used for this purpose includes the animals mentioned hereinbefore.

Referring to the non-human mammal deficient in expression of the DNA of the present invention, the DNA of the present invention can be knocked out by introducing the targeting vector constructed as above into, for example, almurine embryonic stem cell or a murine egg cell and thereby causing the DNA sequence of the targeting vector harboring the inactivated DNA of the present invention to undergo homologous recombination with, and accordingly replacing, the DNA of the present invention on the murine embryonic stem cell or egg cell chromosomes.

The cell with the DNA of the present invention thus knocked out can be obtained by Southern hybridization analysis using a DNA sequence on the DNA of the present invention or in its vicinity as a probe or by PCR using a DNA sequence on the targeting vector or a murine-derived DNA sequence in a region adjacent to but not including the DNA of the present invention used in the targeting vector as primers. When a non-human mammalian embryonic stem cell is used, a cell line with the DNA of the present invention knocked out by the homologous recombination technique is cloned and injected into the non-human mammalian embryo or blastocyte at a suitable stage of embryogenesis, for example at the 8-cell stage, and the resulting chimera embryo is transplanted in the pseudopregnant uterus of the non-human mammal. The animal thus obtained is a chimera animal constituted by both the cells harboring the normal DNA of the present invention and the cells harboring the artificially mutated DNA of the present invention.

When some of the gametes of this chimera animal harbor the mutated DNA of the present invention, an individual of which the entire tissues are constituted by cells harboring the mutated DNA of the present invention can be screened from the colony of animals obtained by crossing such a chimera animal with a normal animal, for example by coat color discrimination. The individuals thus selected are usually animals deficient in hetero-expression of the protein of the present invention and by mating such individuals deficient in hetero-expression of the protein of the present invention with each other, animals deficient in homo-expression of the protein of the present invention can be acquired.

When an egg cell is used, a transgenic non-human mammal with the targeting vector having been introduced into its chromosomes can be prepared by injecting the DNA solution into the egg cell nucleus by the microinjection technique and selecting animals expressing a mutation of the DNA of the present invention by homologous recombination.

The individuals with the DNA of the present invention knocked out are mated to verify that the animals obtained by mating also have the DNA knocked out and they can be sub-bred under the usual breeding conditions.

Preparation and maintenance of the reproduction line can also be carried out in the routine manner. Thus, by mating male and female animals harboring the inactivated DNA, homozygotes having the inactivated DNA in both homologous chromosomes can be obtained. The homozygotes thus obtained are bred under such conditions that, with regard to the dam, the number of homozygotes is plural per normal individual. By mating male and female heterozygotes, homozygotes and heterozygotes both harboring the inactivated DNA can be sub-bred.

The non-human mammalian embryonic stem cell harboring the inactivated DNA of the present invention is very useful for the construction of non-human mammals deficient in expression of the DNA of the present invention. Moreover, the mouse deficient in expression of the protein of the present invention lacks the various biological activities inducible by the protein of the present invention and can, therefore, be of use as an animal model of diseases arising from inactivation of the biological activities of the protein of the present invention, thus being of use in the etiological studies of diseases and development of therapeutics. (8a) A method for screening for a compound having an effect for treating or preventing in the various diseases caused by a defect in or damage to the DNA of the present invention A non-human mammal deficient in expression of the DNA of the present invention can be used in the screening for a compound having an effect for treating or preventing in the diseases (e.g. arteriosclerosis, atherosclerosis, hyperlipidemia, hypercalorism, obesity, hypertriglyceridemia, inflammatory diseases, senescence, diseases of brain, renal disorder, etc.) caused by a defect in or damage to the DNA of the present invention.

Thus, the present invention provides a method for screening for a compound, or a salt thereof, which has an effect for treating or preventing in the diseases caused by a defect in or damage to the DNA of the present invention, which method comprises administering a test compound to a non-human mammal deficient in expression of the DNA of the present invention and monitoring or measuring a change of the non-human mammal.

The non-human mammal deficient in expression of the DNA of the present invention, which is to be used in this screening method, includes the same animals as those mentioned above.

The test compound includes peptides, proteins, non-peptide compounds, synthetic compounds, fermentation products, cell extracts, plant extracts, animal tissue extracts, blood plasma and so on. The test compound may be novel or known compounds.

More specifically, the non-human mammal deficient in expression of the DNA of the present invention is treated with the test compound and the treated animal is compared with an untreated control to evaluate the test compound for an effect for treating or preventing the diseases mentioned above by using a change in some organ or tissue or in a disease symptom as an indicator.

The method of treating the test animal with a test compound can be selected according to the symptom or symptoms manifested by the test animal and the characteristics of the test compound, among other factors and, for example, oral administration or intravenous injection can be employed. The dosage of the test compound can be suitably selected according to the route of administration, the properties of the test compound, and other conditions.

In the screening for a compound with an effect for treating or preventing arteriosclerosis, atherosclerosis, hyperlipidemia, hypercalorism, obesity, hypertriglyceridemia, etc., for instance, the test compound is administered to the non-human mammals deficient in expression of the DNA of the present invention. And, changes in, blood glucose or body weight, etc. in the animal are determined at timed intervals.

When, in the screening method, blood glucose in the test animal is increased about 10% or more, preferably about 30% or more, more preferably about 50% or more, following administration of the test compound, the particular test compound can be selected as a compound capable of producing an effect for treating or preventing arteriosclerosis, atherosclerosis.

The compound obtained by the above screening method has an effect for treating or preventing the diseases (e.g. arteriosclerosis, atherosclerosis) caused by a defect in or damage to the protein, etc. of the present invention and, therefore, can be used as a drug, for example as a safe, low-toxicity agent for treating or preventing the diseases. Furthermore, compounds derived from the compound obtained by the above screening may also be used in the same manner.

The salts of the compound obtained by the screening method as mentioned above include salts with physiologically acceptable bases (e.g. alkali metals) or acids such as organic or inorganic acids, and are preferably a physiologically acceptable acid addition salt. Examples of such salts are salts thereof with inorganic acids (e.g. hydrochloric acid, phisphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.).

The composition for treating or preventing the diseases mentioned above comprising the compound obtained the screening method can be prepared in the same as the pharmaceutical composition comprising the protein, etc. of the present invention as mentioned above.

Because the thus-obtained preparation is safe and of low toxicity, it can be administered to humans or mammals (e.g., rat, mouse, guinea pig, rabbit, sheep, pig, bovine, horse, cat, dog, monkey, etc.).

The dose of the compound may vary depending on subject disease, subject of administration, way of administration, and so on. When the compound is used, for example, for treating cancer by oral administration, the dose of the compound is normally about 0.1 to 100 mg, preferably 1.0 to 50 mg, and more preferably 1.0 to 20 mg per day for an adult human (weighing 60 kg). When the compound is used, for example, for treating arteriosclerosis, atherosclerosis by non-oral administration, it is advantageous to administer the compound in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject disease and so on. For other animal species, corresponding doses as converted per 60 kg weight can be administered. (8b) A method for screening for a compound capable of promoting or inhibiting an activity of the promoter for the DNA of the present invention The present invention provides a method for screening for a compound, or a salt thereof, which promotes or inhibits an activity of the promoter for the DNA of the present invention, which method comprises administering a test compound to a non-human mammal deficient in expression of the DNA of the present invention, wherein the DNA of the present invention is inactivated by introducing of a reporter gene and detecting the expression of the reporter gene.

As the test compound, the same compounds as those mentioned hereinbefore can be used.

Examples of the reporter gene are the same genes as those mentioned hereinbefore. Preferable examples are a β-galactosidase gene (lacZ) and so on.

In non-human mammals deficient in expression of the DNA of the present invention wherein the DNA of the present invention is inactivated by introducing a reporter gene, the reporter gene is under the control of the promoter for the DNA of the present invention and, therefore, the activity of the promoter can be detected by tracing the expression of the substance encoded by the reporter gene.

For instance, when part of the DNA region coding for the protein of the present invention is inactivated by the *Escherichia coli*-derived β-galactosidase gene (lacZ), β-galactosidase is expressed in those tissues in which the protein of the present invention would have been expressed. Therefore, the status of expression of the protein of the present invention in a living animal body can be traced, easily and expediently, for example, by the staining method using a reagent serving as a substrate for β-galactosidase, such as 5-bromo-4-chloro-3-indolyl-β-galactopyranoside (X-gal). More specifically, a tissue section of a mouse defective in the protein of the present invention is fixed with glutaraldehyde or the like, washed with Dulbecco's phosphate-buffered saline (PBS), and reacted with a staining solution containing X-gal at room temperature or around 37° C. for about 30 minutes to 1 hour. The tissue sample is then washed with 1 mM EDTA/PBS solution to terminate the β-galactosidase reaction and observed for color development. Alternatively, the mRNA coding for lacZ may be detected by a conventional method.

The compound, or a salt thereof, as obtained by the above screening method is a compound selected from among the test compounds mentioned above and, as such, is a compound capable of promoting or inhibiting the activity of the promoter for the DNA of the present invention.

The salts of the compound obtained by the screening method as mentioned above include salts with physiologically acceptable bases (e.g. alkali metals) or acids such as organic or inorganic acids, and are preferably a physiologically acceptable acid addition salt. Examples of such salts are salts thereof with inorganic acids (e.g. hydrochloric acid, phosphoric acid, hydrobromic acid or sulfuric acid, etc.) and salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid, etc.).

The compound, or a salt thereof, which promotes the activity of the promoter for the DNA of the present invention is capable of promoting the expression of the protein of the present invention and, hence, the promoting function of the protein. Therefore, the compound is useful as a drug, such as a safe, low-toxic agent for treating or preventing diseases such as arteriosclerosis, atherosclerosis, hyperlipidemia, hypercalorism, obesity, hypertriglyceridemia, inflammatory diseases, senescence, diseases of brain, renal disorder, etc.

On the other hand, the compound, or a salt thereof, which inhibits the activity of the promoter for the DNA of the present invention is capable of inhibiting expression of the protein of the present invention and, hence, inhibiting the function of the protein. Therefore, the compound is useful as a drug, such as a safe,.low-toxic agent for treating or preventing diseases such as malnutrition, abetalipoproteinemia or Tangier disease, etc.

Furthermore, compounds derived from the compound obtained by the above screening method may also be used in the same way.

The agent for treating or preventing the above-mentioned diseases comprising the compound obtained the screening method can be prepared in the same as the pharmaceutical composition comprising the protein, etc. of the present invention as mentioned above.

Because the thus-obtained preparation is safe and of low toxicity, it can be administered to humans or mammals (e.g., rat, mouse, guinia pig, rabbit, sheep, pig, bovine, horse, cat, dog, monkey, etc.).

The dose of the compound may vary depending on subject disease, subject of administration, way of administration, and so on. When the compound which promotes an activity of the promoter is used, for example, for treating arteriosclerosis, atherosclerosis by oral administration, the dose of the compound which promotes an activity of the promoter is normally about 0.1 to 100 mg, preferably 1.0 to 50 mg, and more preferably 1.0 to 20 mg per day for an adult human (weighing 60 kg). When the compound which promotes an activity of the promoter is used, for example, for treating arteriosclerosis, atherosclerosis by non-oral administration, it is advantageous to administer the compound which promotes an activity of the promoter in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject disease and so on. For other animal species, corresponding doses as converted per 60 kg weight can be administered.

When the compound which inhibits an activity of the promoter is used, for example, for treating abetalipoproteinemia by oral administration, the dose of the compound which inhibits an activity of the promoter is normally about 0.1 to 100 mg, preferably 1.0 to 50 mg, and more preferably 1.0 to 20 mg per day for an adult human (weighing 60 kg). When the compound which inhibits an activity of the promoter is used, for example, for treating abetalipoproteinemia by non-oral administration, it is advantageous to administer the compound which inhibits an activity of the promoter in the form of injectable preparation at a daily dose of about 0.01 to 30 mg, preferably about 0.1 to 20 mg, and more preferably about 0.1 to 10 mg per administration by an intravenous injection for an adult human (weighing 60 kg), depending on subject of administration, subject disease and so on. For other animal species, corresponding doses as converted per 60 kg weight can be administered.

In this way, the non-human mammal deficient in expression of the DNA of the present invention is very useful in view of the screening of a compound or a salt thereof which promotes or inhibits promoter activities of the DNA of the present invention, and useful for developing a pharmaceutical composition for treating or preventing various diseases arisen from deficiency in expression of the DNA of the present invention, and for analysis the in vivo mechanism of the various diseases.

Also, various kinds of DNAs coding proteins can be linked at downstream of the DNA comprising a promoter region of the LCAT-like protein of the present invention (e.g. the DNA comprising a nucleotide sequence represented by SEQ ID NO:38, substantially equivalent thereof, or a partial DNA thereof), to prepare a gene construct which can be microinjected into the fertilized egg of animals to produce transgenic animals. By using such transgenic animals, the mechanism of the protein in animals can be determined.

Moreover, by linking a suitable receptor gene at the above-mentioned promoter, and by constructing a cell-line which can produce the protein of the present invention, it can be used as an assay system to find low-molecular compounds which specifically promote or inhibit a producing activity of the LCAT-like protein in vivo.

Further, by analyzing the promoter mentioned above, it is possible to find a cis element or a transcription factor which can bind the promoter.

Examples of the DNA comprising substantially the same nucleotide sequence represented by SEQ ID NO:38, may be any DNA comprising the nucleotide sequence hybridizing to the nucleotide sequence represented by SEQ ID NO:38 under a highstringent condition and having substantially the same promoter activities of the DNA having the nucleotide sequence represented by SEQ ID NO:38.

Examples of the DNA which comprises the nucleotide sequence hybridizing to the nucleotide sequence represented by SEQ ID NO:38 under a highstringent condition are a DNA comprising a nucleotide sequence of not less than about 70%, preferably not less than about 80%, more preferably not less than about 90%, for still better result, not less than about 95% identity to the nucleotide sequence represented by SEQ ID NO:38.

The method of the hybridization and the highstringent condition are the same as mentioned above.

In the specification, claims and drawings of the present application, the abbreviations used for bases (nucleotides), amino acids and so forth are those recommended by the IUPAC-IUB Commission on Biochemical Nomenclature or those conventionally used in the art. Examples thereof are given below. Amino acids for which optical isomerism is possible are, unless otherwise specified, in the L form.
DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
DATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetracetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr:Tyrosine
Trp: Tryptophan
Pro: Proline
Asn: Asparagine
Gln: Glutamine
pGlu: Pyroglutamic acid Substitution groups, protecting groups and reagents used in the specification of the present application are represented by the symbols set forth below.
Me: Methyl
Et: Ethyl
Bu: Butyl
Ph: Phenyl
TC: Thiazolidine-4(R)-carboxamide
Tos: p-Toluenesulfonyl
CHO: Formyl
Bzl: Benzyl
$C^{12}$-Bzl: 2,6-Dichlorobenzyl
Bom: Benzyloxymethyl
Z: Benzyloxycarbonyl
Cl-Z: 2-Chlorobenzyloxycarbonyl
Br-Z: 2-Bromobenzyloxycarbonyl
Boc: tert-Butoxycarbonyl
DNP: Dinitrophenyl
Trt: Trityl
Bum: tert-Butoxymethyl
Fmoc: N-9-Fluorenylmethyloxycarbonyl
HOBt: 1-Hydroxybenzotriazole
HOOBt: 3,4-Dihydro-3-hydroxy-4-oxo-1,2,3-benzotriazine
HONB: 1-hydroxy-5-norbornene-2,3-dicarboximide
DCC: Dicyclohexylcarbodiimide SEQ ID NO:1 shows the amino acid sequence of a human protein of the present invention (matured), derived from human heart;

SEQ ID NO:2 shows the amino acid sequence of a human protein of the present invention (matured), derived from human kidney, wherein the 32 amino acids residues of 64th(Glu)–95th(Leu) in the amino acid sequence of SEQ ID NO:2 are inserted between the 63rd(Leu) and 64th(Val) in the amino acid sequence of SEQ ID NO:1;

SEQ ID NO:3 shows the amino acid sequence of a murine protein of the present invention (mature), derived from murine kidney;

SEQ ID NO:4 shows the amino acid sequence of a human protein of the present invention (mature), derived from human heart;

SEQ ID NO:5 shows the amino acid sequence of a human protein of the present invention (mature), derived from human kidney, wherein the 32 amino acids residues of 67th(Glu)–98th(Leu) in the amino acid sequence of SEQ ID NO:5 are inserted between the 66th(Leu) and 67th(Val) in the amino acid sequence of SEQ ID NO:4;

SEQ ID NO:6 shows the amino acid sequence of a human precursor protein of the present invention, derived from human heart;

SEQ ID NO:7 shows the amino acid sequence of a human precursor protein of the present invention, derived from human kidney, wherein the 32 amino acids residues of 97th(Glu)–128th(Leu) in the amino acid sequence of SEQ ID NO:7 are inserted between the 96th(Leu) and 97th(Val) in the amino acid sequence of SEQ ID NO:6;

SEQ ID NO:8 shows the amino acid sequence of a murine precursor protein of the present invention, derived from murine kidney;

SEQ ID NO:9 shows the amino acid sequence of a signal peptide of the present invention;

SEQ ID NO:10 shows the amino acid sequence of a signal peptide of the present invention;

SEQ ID NO:11 shows the amino acid sequence of a signal peptide of the present invention;

SEQ ID NO:12 shows the nucleotide sequence of a DNA coding for the human protein (mature) derived from a human heart having the amino acid sequence represented by SEQ ID NO:1 of the present invention;

SEQ ID NO:13 shows the nucleotide sequence of a DNA coding for the human protein (mature) derived from a human kidney having the amino acid sequence represented by SEQ ID NO:2 of the present invention;

SEQ ID NO:14 shows the nucleotide sequence of a DNA coding for the murine protein (mature) having the amino acid sequence represented by SEQ ID NO:3 of the present invention;

SEQ ID NO:15 shows the nucleotide sequence of a DNA coding for the human protein (mature) derived from a human heart having the amino acid sequence represented by SEQ ID NO:4 of the present invention;

SEQ ID NO:16 shows the nucleotide sequence of a DNA coding for the human protein (mature) derived from a human kidney having the amino acid sequence represented by SEQ ID NO:5 of the present invention;

SEQ ID NO:17 shows the nucleotide sequence of a DNA coding for the human protein derived from a human heart having the amino acid sequence represented by SEQ ID NO:6 of the present invention;

SEQ ID NO:18 shows the nucleotide sequence of a DNA coding for the human protein derived from a human kidney having the amino acid sequence represented by SEQ ID NO:7 of the present invention;

SEQ ID NO:19 shows the nucleotide sequence of a DNA coding for the human protein derived from a murine kidney having the amino acid sequence represented by SEQ ID NO:8 of the present invention;

SEQ ID NO:20 shows the nucleotide sequence of a DNA coding for the signal peptide having the amino acid sequence represented by SEQ ID NO:9 of the present invention;

SEQ ID NO:21 shows the nucleotide sequence of a DNA coding for the signal peptide having the amino acid sequence represented by SEQ ID NO:10 of the present invention;

SEQ ID NO:22 shows the nucleotide sequence of a DNA coding for the signal peptide having the amino acid sequence represented by SEQ ID NO:11 of the present invention;

SEQ ID NO:23 shows the partial nucleotide sequence of a DNA coding for the human protein of the present invention which is used for a cloning of the full length of DNA coding for the human protein of the present invention as shown in Example 1;

SEQ ID NO:24 shows the nucleotide sequence of a synthetic primer used for cloning of the DNA coding for the human protein of the present invention as shown in the Example 1;

SEQ ID NO:25 shows the nucleotide sequence of a synthetic primer used for cloning of the DNA coding for the human protein of the present invention as shown in the Example 1;

SEQ ID NO:26 shows the nucleotide sequence of a synthetic primer used for cloning of the DNA coding for the human protein of the present invention as shown in the Example 1;

SEQ ID NO:27 shows the nucleotide sequence of a synthetic primer used for cloning of the DNA coding for the murine protein of the present invention as shown in the Example 2;

SEQ ID NO:28 shows the nucleotide sequence of a synthetic primer used for cloning of the DNA coding for the murine protein of the present invention as shown in the Example 2;

SEQ ID NO:29 shows the partial nucleotide sequence of a DNA coding for the human protein of the present invention which is used for a cloning of the full length of DNA coding for the murine protein of the present invention as shown in Example 2;

SEQ ID NO:30 shows the nucleotide sequence of a synthetic primer used for cloning of the DNA coding for the murine protein of the present invention as shown in the Example 2;

SEQ ID NO:31 shows the nucleotide sequence of a synthetic primer used for cloning of the DNA coding for the murine protein of the present invention as shown in the Example 2;

SEQ ID NO:32 shows the nucleotide sequence of a synthetic primer used for cloning of the DNA coding for the murine protein of the present invention as shown in the Example 2;

SEQ ID NO:33 shows the nucleotide sequence of a synthetic primer used for cloning of the genomic DNA coding for the human protein of the present invention as shown in the Example 3;

SEQ ID NO:34 shows the nucleotide sequence of a synthetic primer used for cloning of the genomic DNA coding for the human protein of the present invention as shown in the Example 3;

SEQ ID NO:35 shows the nucleotide sequence of an adapter used for cloning of the genomic DNA coding for the human protein of the present invention as shown in the Example 3;

SEQ ID NO:36 shows the nucleotide sequence of a synthetic primer used for cloning of the genomic DNA coding for the human protein of the present invention as shown in the Example 3;

SEQ ID NO:37 shows the nucleotide sequence of a synthetic primer used for cloning of the genomic DNA coding for the human protein of the present invention as shown in the Example 3;

SEQ ID NO:38 shows the nucleotide sequence of 5' flanking (a promoter sequence) of the genomic DNA coding for the human protein of the present invention;

SEQ ID NO:39 shows the amino acid sequence of the chemically synthesized partial peptide of human LCAT-like protein of the present invention as shown in the Example 5;

SEQ ID NO:40 shows the amino acid sequence of the chemically synthesized partial peptide of human LCAT-like protein of the present invention as shown in the Example 5;

SEQ ID NO:41 shows the nucleotide sequence of the primer for synthesizing the FLAG peptide as shown in the Example 7;

SEQ ID NO:42 shows the nucleotide sequence of the primer for synthesizing the FLAG peptide as shown in the Example 7;

SEQ ID NO:43 shows the amino acid sequence of the partial peptide as shown in the Example 11.

The transformant strain of *Escherichia coli* DH10B/pTB1972, which is obtained in the Example 1 mentioned hereinafter, is on deposit under the terms of the Budapest Treaty from Apr. 7, 1997, with the NIBH under the Accession Number of FERM BP-5900. It is also on deposit from Apr. 9, 1997 with the IFO under the Accession Number of IFO 16072.

The transformant strain of *Escherichia coli* DH10B/pTB1973, which is obtained in the Example 1 mentioned hereinafter, is on deposit under the terms of the Budapest Treaty form Apr. 7, 1997, with the NIBH under the Accession Number of FERM BP-5901. It is also on deposit from Apr. 9, 1997 with the IFO under the Accession Number of IFO 16073.

The transformant strain of *Escherichia coli* DH10B/pTB2010, which is in the Example 2 mentioned hereinafter, is on deposit under the terms of the Budapest Treaty from Jul. 8, 1997, with the NIBH under the Accession Number of FERM BP-6011. It is also on deposit from Jul. 9, 1997 with the IFO under the Accession Number of IFO 16111.

The transformant strain of *Escherichia coli* DH5α/pTB2022, which is obtained in the Example 4 mentioned hereinafter, is on deposit under the terms of the Budapest Treaty from Jan. 20, 1998, with the NIBH under the Accession Number of FERM BP-6227. It is also on deposit from Jan. 19, 1998 with the IFO under the Accession Number of IFO 16154.

BRIEF DESCRIPTION OF THE DRAWINGS

FIG. 1 shows the nucleotide sequence of the DNA coding for the human protein derived from human heart of the present invention and the amino acid sequence of the human protein derived from human heart of the present invention as deduced from the nucleotide sequence;

FIG. 2 shows the nucleotide sequence of the DNA coding for the human protein derived from human kidney of the present invention and the amino acid sequence of the human protein derived from human kidney of the present invention as deduced from the nucleotide sequence;

FIG. 3 shows the nucleotide sequence of the DNA coding for the murine protein derived from murine kidney of the present invention and the amino acid sequence of the murine protein derived from murine kidney of the present invention as deduced from the nucleotide sequence;

FIG. 4 shows the comparative amino acid sequences between the human protein derived from a human heart and the murine protein derived from murine kidney. hCLP shows the human protein derived from human heart. mCLP shows the murine protein derived from murine kidney. The black parts show the different amino acid between the two amino acid sequences.

FIG. 5 shows the 5' flanking region (the promoter region) of the nucleotide sequence of the DNA coding for the human LCAT-like protein of the present invention.

FIG. 6 shows the 1st to 1500th of the nucleotide sequence of the 5' flanking region (the promoter region) of the nucleotide sequence of the DNA coding for the human LCAT-like protein of the present invention which contains adaptor sequence, the 1st to 36th of the nucleotide sequence.

FIG. 7 shows the 1501st to 2867th of the nucleotide sequence of the 5' flanking region (the promoter region) of the nucleotide sequence of the DNA coding for the human LCAT-like protein of the present invention which contains the initiation codon ATG, the 2868th to 2870th of the nucleotide sequence.

FIG. 14 shows the UV absorbance and the results of the Western blotting in the Example 12.

BEST MODE FOR CARRYING OUT THE PRESENT INVENTION

EXAMPLES

Figure 8:
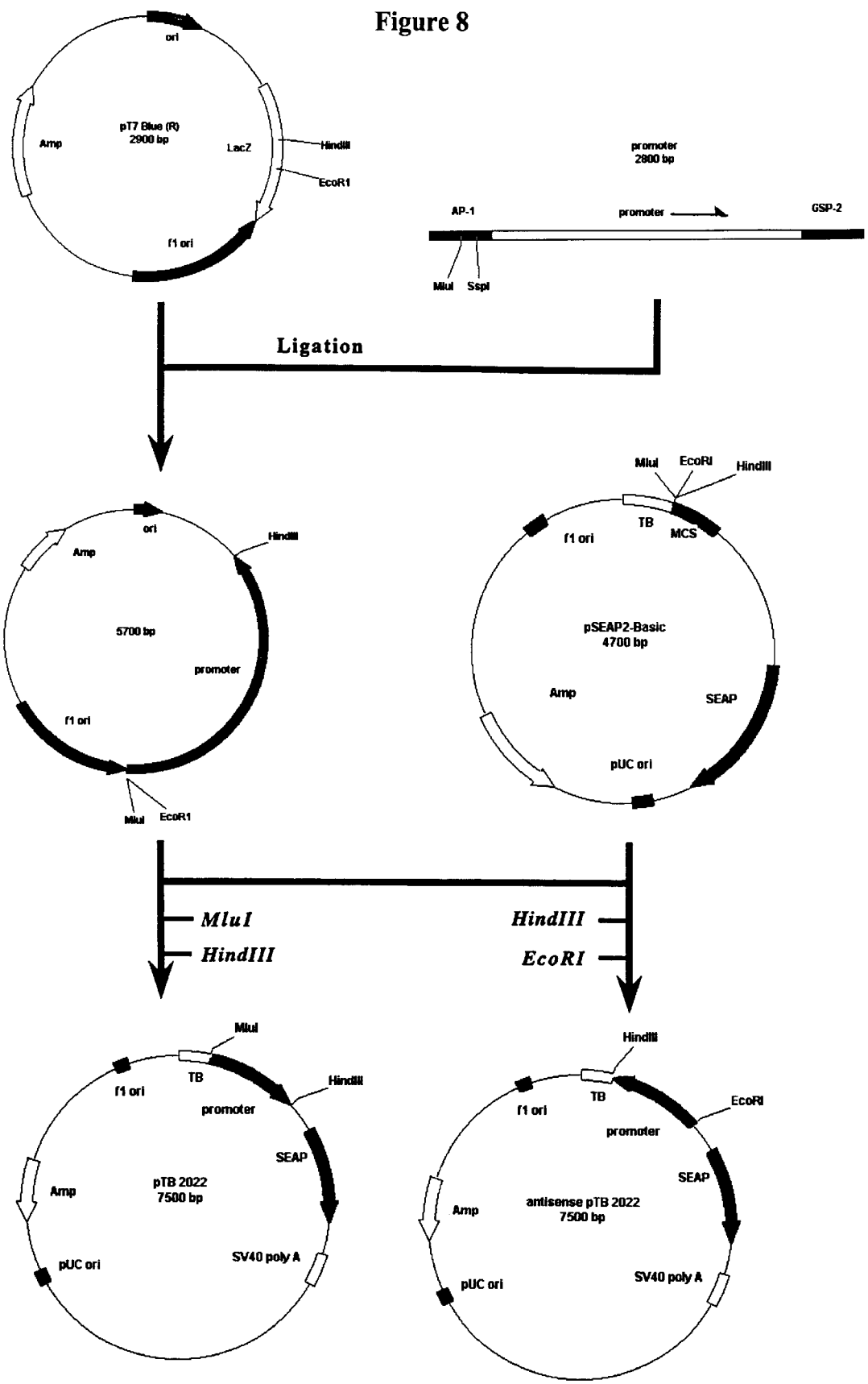
FIG. 8 shows the construction scheme for the plasmids pTB 2022 and antisence pTB 2022 obtained by the method described in the Example 4.

The following examples are intended to describe the present invention in further detail and should by no means be interpreted as defining the scope of the present invention. The gene manipulation using *Escherichia coli* was carried out in accordance with the procedure described in Molecular Cloning.

Example 1

Cloning of the Gene Coding for the Human LCAT-like Protein of the Invention (1) Subtractive Concentration of mRNA Differing in the Amount of Expression Between the Foam Cells Prepared From the THP-1 Cells Made Macrophage-like by Two Methods The preparation of foam cells from THP-1 cells (Dainippon Pharmaceutical) was carried out principally according to the method of A. Rodriguez et al. (Journal of Lipid Research, 35, 1909, 1994). Thus, THP-1 cells were made macrophage-like by 3-day treatment with 400 ng/ml of phorbol myristate acetate (PMA) and then exposed to 0.2 mg TC (total cholesterol)/ml of β VLDL (very low density lipoprotein) for 1 day. The resultant cholesterol-loaded cells were used as a 400 ng PMA-treated THP-1-derived foam cell sample. Similarly, the same monocytes as used above were treated with 5 ng/ml of PMA for 5 days and the resultant macrophage-like cells were exposed to 0.2 mg TC/ml of β VLDL for one day to prepare a 5 ng PMA-treated THP-1-derived foam cell sample.

From both samples, the total RNA was extracted with guanidine isothiocyanate (Pharmacia) and the poly(A)+ RNA was purified by means of an oligo-dT cellulose column (Pharmacia). Starting with 2 µg of each poly(A)+RNA, a subtractive PCR was carried out using PCR-Select cDNA Subtraction Kit (Clontech) to collect a cDNA fragment (a PCR amplification product of a portion of the cDNA) specifically expressed in the 5 ng PMA-treated foam cell sample.

The adapter sequences added for subtraction were cleaved off from both ends of the PCR product fragment by using the restriction enzyme RsaI and the blunt-ended DNA fragment thus obtained was subcloned in pCR-Script (Stratagene). The nucleotide sequences of the subcloned cDNA fragments were determined, and based on the sequences thus found, a homology search was made using the BLAST N program against Genemble Database, a public database. As a result, Clone 4S-086 (SEQ ID NO:23) was found to have a novel DNA nucleotide sequence having approximately 61% similarity with the known human LCAT (Biochimica et Biophysica Acta, 910, 142–148, 1987).

(2) Isolation of the Full-length cDNA Based on Clone 4S-086 cDNA Fragment

Using the above Clone 4S-086 as a probe, Northern analysis was performed with a commercial MTN membrane (Clontech). This analysis revealed that the particular gene had been expressed mainly in the heart, placenta, skeletal muscle, kidney, and testis. Therefore, it was decided to isolate this full-length cDNA from human heart and human kidney cDNA libraries.

Cloning of the cDNA was performed using Gene Trapper Positive Selection System (Gibco BRL).

*Escherichia coli* DH12S strains from the human heart and human kidney cDNA libraries (Gibco BRL) were respectively cultured in Terrific Broth (12 g/l bacto-tryptone (Difco), 24 g/l bacto-yeast extract (Difco), 2.3 g/l monopotassium phosphate, 12.5 g/l dipotassium phosphate) at 30° C. for 16 hours, and using Quiagen Plasmid Isolation Kit (Quiagen), plasmid cDNA libraries were extracted and purified. The purified plasmid cDNA libraries were respectively digested with GeneII and ExoIII (both from Gibco BRL) to construct single-stranded cDNA libraries.

The following synthetic oligonucleotide was used as a probe in the screening of cDNA libraries.

5'-GCTGCTGCCCTACAACTACACAT-3' (SEQ ID NO:24)

The 3' end of the probe was labeled with TdT tailed with biotin-14-dCTP (Gibco BRL). Each single-stranded cDNA library was incubated at 95° C. for 1 minute and quenched on ice. Then, the biotinylated probe was added and 1-hour prehybridization at 37° C. and hybridization at room temperature were carried out. After hybridization, Gene Trapper Positive Selection System Magnetic Beads (Gibco BRL) were added and the system was incubated for 30 minutes at room temperature with stirring at 2-minute intervals. Then, the system was placed in Gene Trapper Positive Selection System Magnet Track (Gibco BRL) and allowed to stand for 2 minutes. The supernatant was discarded and the Magnetic Beads were washed with Gene Trapper Positive Selection System Wash Buffer. This washing with Wash Buffer was carried out 3 times. After standing in Magnetic Track, the supernatant was discarded. Then, Gene Trapper Positive Selection System Elution Buffer was added and the system was allowed to stand at room temperature for 5 minutes. After 5 minutes'0 standing in the Magnetic Track, the supernatant DNA solution was harvested.

As a primer, the synthetic oligonucleotide:

5'-GCTGCTGCCCTACAACTACACAT-3' (SEQ ID NO:24) was added to the harvested DNA solution and the mixture was incubated at 95° C. for 1 minute. Then, Gene Trapper Positive Selection System Repair Enzyme was added and the system was incubated at 70° C. for 15 minutes to synthesize a double-stranded DNA. Using an electropolator (Bio-Rad), the double-stranded DNA synthesized above was used to transform *Escherichia coli* DH10B.

A screening for the positive transformants by colony-PCR using the following two oligonucleotides as primers was carried out.

5'-TATCCGGGCCTTCGTGTCA-3' (SEQ ID NO:25)

5'-TCAAAGCCGATGTCCTGGAAGAACTTGC-3' (SEQ ID NO:26)

By detecting the colonies showing a PCR product of about 220 bp as positive clones, 2 clones each, or a total of 4 clones, were selected from the human heart and human kidney cDNA libraries.

The selected *E. coli* cells were respectively cultured and the DNA was extracted and subjected to a cycling reaction using ABI PRISH Dye Terminator Cycle Sequence Ready Reaction Kit with AmpliTaq DNA polymerase, FS (Perkin-Elmer) and the nucleotide sequence of each cDNA fragment was determined using 377 DNA Sequencer (Perkin-Elmer). Then, based on the nucleotide sequences so determined, an alignment search was made. As a result, the two clones derived from the human heart cDNA library and one of the two clones derived from the human kidney cDNA library were found to harbor a 1271-base nucleotide sequence containing the sequence of SEQ ID NO:17. The remaining one clone derived from the human kidney cDNA library harbored a 1335-base nucleotide sequence containing the sequence of SEQ ID NO:18, which corresponded to the insertion of 96 bases into the sequence harbored by the above-mentioned 2 clones from the human heart cDNA library.

In the former cDNA fragment, 412 amino acids of SEQ ID NO:6 and, in the latter cDNA fragment, 444 amino acids of SEQ ID NO:7 were respectively encoded, and both had novel LCAT-like proteins encoded.

The plasmids pTB1972 and pTB1973 harboring the DNAs coding for the two novel LCAT-like proteins of the invention were respectively used to transform *Escherichia coli* DH10B to obtain two transformants, *E. coli* DH10B/pTB1972 and DH10B/pTB1973.

Example 2

Cloning of the cDNA Coding for a Novel Murine LCAT-like Protein

Cloning of a partial sequence of the novel murine LCAT-like protein was performed by PCR. *Escherichia coli* DH12S from a murine kidney cDNA library (Gibco BRL) was cultured in Terrific Broth (12 g/l bacto-tryptone (Difco), 24 g/l bacto-yeast extract (Difco), 2.3 g/l monopotassium phosphate, 12.5 g/l dipotassium phosphate) at 30° C. for 16 hours, and using Quiagen Plasmid Kit (Quiagen), a plasmid cDNA library was constructed and used as a template.

Based on the sequence data on the novel human LCAT-like proteins, the following two synthetic oligonucleotides were synthesized and used as primers.

5'-GTGGTGCTGGTCCCTGGTGATTTG-3' (SEQ ID NO:27)

5'-GGTGGCCCTGGATGTTTTGTTG-3' (SEQ ID NO:28)

Using a thermal cycler (GeneAmp PCR System 2400, Perkin-Elmer), PCR reaction was carried out in a system containing TaKaRa Ex Taq (Takara Shuzo) in 30 cycles of 30 seconds at 94° C., 30 seconds at 55° C., one minute at 72° C., and extension at 4° C.

The resultant PCR product was inserted into pT7 Blue-T-Vector (Novagen) using DNA Ligation Kit Version 2 (Takara Shuzo) and subcloned into *Escherichia coli* DH5α.

From the transformant thus obtained, the plasmid DNA was extracted and subjected to a cyclizing reaction with Dye Terminator Cycle Sequence FS Ready Reaction Kit (Perkin-Elmer), and the nucleotide sequence of the cDNA fragment was determined with 377 DNA Sequencer (Perkin-Elmer).

The harvested clone had a 198-base nucleotide sequence of SEQ ID NO:29. Therefore, it was decided to obtain this full-length cDNA from the murine kidney cDNA library.

Cloning of the cDNA was performed using Gene Trapper Positive Selection System (Gibco BRL).

The plasmid cDNA library used above was digested with GeneII and ExoIII (both from Gibco) to construct a single-stranded cDNA library.

On the other hand, the following synthetic oligonucleotide was used as a probe in the screening of the cDNA library.

5'-GGTTGTACACTACCTTTGCTCCAAG-3' (SEQ ID NO:30)

The 3' end of the probe was labeled by biotinylation using TdT/biotin-14-dCTP (Gibco BRL). The single-stranded cDNA library was denatured at 95° C. for 1 minute and quenched on ice and the biotinylated probe was added. Prehybridization was performed at 37° C. for 1 hour, followed by hybridization at room temperature. After hybridization, Gene Trapper Positive Selection System Magnetic Beads were added and the system was allowed to stand for 30 minutes at room temperature with stirring at 2-minute intervals. Then, the system was put in Gene Trapper Positive Selection System Magnetic Track (Gibco BRL) and allowed to stand for 2 minutes. The supernatant was discarded and the Magnetic Beads were washed with Gene Trapper Positive Selection System Wash Buffer. This washing with Wash Buffer was carried out 3 times. After standing in the Magnetic Track, the supernatant was discarded. Then, Gene Trapper Positive Selection System Elution Buffer was added and the system was allowed to stand at room temperature for 5 minutes. After 5 minutes' standing in the Magnetic Track, the supernatant DNA solution was recovered.

As a primer, the synthetic oligonucleotide:

5'-GGTTGTACACTACCTTTGCTCCAAG-3' (SEQ ID NO:30) was added to the above DNA solution and the mixture was incubated at 95° C. for 1 minute. Then, Gene Trapper Positive Selection System Repair Enzyme was added and the system was incubated at 70° C. for 15 minutes to synthesize a double-stranded DNA. Using an electropolator (Bio-Rad), the double-stranded DNA synthesized above was used to transform *Escherichia coli* DH10B.

A screening for the positive transformants by colony-PCR using the following two oligonucleotides as primers was carried out.

5'-GGTAACCAGTTGGAAGCAAAG-3' (SEQ ID NO:31)

5'-ATCCAGCAGTCAATGATAACA-3' (SEQ ID NO:32)

By detecting the colonies showing a PCR product fragment of about 130 bp as positive clones, a total of 3 clones were selected from the murine kidney cDNA library.

The selected *E. coli* cells were respectively cultured and the DNA were respectively extracted and subjected to a cycling reaction using ABI PRISH Dye Terminator Cycle Sequence Ready Reaction Kit with AmpliTaq DNA polymerase, FS (Perkin-Elmer) and the nucleotide sequence of each cDNA fragment was determined using 377 DNA Sequencer (Perkin-Elmer). Then, based on the nucleotide sequences so determined, an alignment search was made. As a result, the three clones obtained were found to harbor the same DNA fragment and had a 2734-base nucleotide sequence containing the sequence of SEQ ID NO:19. This cDNA fragment had 412 amino acids of SEQ ID NO:8 encoded, and a novel murine LCAT-like protein was encoded.

This novel murine LCAT-like protein had 85.0% similarity at the base level and 88.1% similarity at the amino acid level with the novel-human LCAT-like protein having the amino acid sequence of SEQ ID NO:1 as obtained in Example 1 [FIG. 4]. The plasmid pTB2010 harboring the DNA coding for the novel murine LCAT-like protein of the invention was used to transform *Escherichia coli* DH10B to provide a transformant, *Escherichia coli* DH10B/pTB2010.

Example 3

Cloning of the Genomic DNA of the Novel Human LCAT-like Protein

Using Promoter Finder DNA Working Kit (Clontech), the sequence around the initiation codon of the DNA coding for the human protein of the invention was analyzed. The human genomic DNA was digested with Ssp I restriction enzyme and an adapter sequence [5'-GTAATACGACTCACTATAGGGCACGCGTGGTCG ACGGCCCGGGCTGGT-3' (SEQ ID NO:35)] available with Primer AP 1 [5'-GTAATACGACTCACTATAGGGC-3' (SEQ ID NO:33) (Clontech)] and Primer AP 2 [5'-ACTATAGGGCACGCGTGGT-3' (SEQ ID NO:34) (Clontech)] was ligated to its 5' and 3' ends.

The oligonucleotides GSP 1 [5'-ATCCGGGAGCAGCCCCACACGGTAGG-3' (SEQ ID NO:36)] and GSP 2 [5'-GGTGTACGACGGTCGCCGCAGGTC-3' (SEQ ID NO:37)], which sequences are complementary to those from base +45 to base +20 and from base -1 to base -24 of the 5' flanking sequence (FIG. 5) of the cDNA coding for the novel human LCAT-like protein, respectively, were synthesized as PCR primers.

The primary PCR was performed using the above human genomic DNA solution, TaKaRa LA PCR Kit Version 2 (Takara Shuzo), AP 1, and synthetic oligonucleotide GSP 1 on a thermal cycler (GeneAmpR PCR System 2400, Perkin-Elmer) in 30 cycles of 10 seconds at 95° C., 30 seconds at 65° C., and 5 minutes at 72° C. This reaction mixture was diluted 50-fold with sterilized water and subjected to the secondary PCR. The secondary PCR was carried out using the above primary PCR product dilution, TaKaRa LA PCR Kit Version 2 (Takara Shuzo), AP 2, and synthetic nucleotide GSP 2 on a thermal cycler (GeneAmpR PCR System 2400, Perkin-Elmer) in 25 cycles of 10 seconds at 95° C., 30 seconds at 65° C., and 5 minutes at 72° C.

The about 2.9 kbp amplified fragment obtained from the Ssp I-digested genomic DNA solution was inserted into pT7 Blue-T-Vector (Novagen) using DNA Ligation Kit Version 2 (Takara Shuzo) and introduced into *Escherichia coli* DH5α to construct a transformant. From this transformant, the plasmid DNA was extracted and subjected to a cycling reaction using Dye Terminator Cycle Sequence FS Ready Reaction Kit (Perkin-Elmer) and the nucleotide sequence of the amplified product was determined with 377 DNA Sequencer (Perkin-Elmer). The sequence is shown in FIGS. 6 and 7.

The clone thus obtained showed the existence of a sequence in complete agreement with the base -81 to base -25 of the 5' flanking sequence of the cDNA of the novel human LCAT-like protein in the base 2788-base 2843 region of the sequence shown in FIGS. 6 and 7, indicating that this sequence is the sequence of the 5' flanking region of the novel human LCAT-like protein gene. Analysis for the cis element in this flanking sequence was made using GENE-TYX Bio Database Software Ver. 32.0 (Software Development) and by inventor's eyes.

Example 4

Assay of the Promoter Activity of the Novel Human LCAT-like Protein Gene

To confirm that the genomic DNA fragment cloned in Example 3 has promoter activity, the promotor activity detection system was constructed using alkaline phosphatase gene as a reporter. The method for construction of a plasmid with alkaline phosphatase gene as the reporter gene under the control of the genomic DNA fragment obtained in Example 3 is illustrated in FIG. 8.

First, from the plasmid with a sequence of about 2.9 kbp from the base 1 to base 2867 of the nucleotide sequence shown in FIGS. 6 and 7 as cloned in pT7 Blue-T-Vector, the 2.9 kbp fragment was isolated using Mlu I-Hind III and introduced into the flanking Mlu I-Hind III site of the pSEAP-Basic (Clontech) alkaline phosphatase gene. This gene was then introduced into *Escherichia coli* DH5α to construct an expression plasmid pTB-2022. At the same time, the 2.9 kbp fragment was isolated with Hind III-EcoR I and inserted in the flanking Hind III-EcoR I site of the pSEAP-Basic alkaline phosphatase gene to construct a reverse-inserted expression plasmid as well. This plasmid was used as a negative control.

Introduction of the plasmid into the WI38 VA13 cell line was carried out by the lipofectin method using Trans IT™-LT1 (Mirus). Thus, the cells seeded at a density of $1 \times 10^5$ cells/962 mm² (a 6-well plate) were cultured for 24 hours. After serum-free medium was substituted, 3 μg/well of each plasmid and 10 μl/μg DNA of Trans IT-LTI were added and the plate was incubated for 4 hours. After transfection, the cells were cultured in DMEM medium containing 10% FBS (fetal bovine serium) and the supernatant was pooled after 72 hours. Using this cell supernatant, alkaline phosphatase activity was determined.

Figure 9:
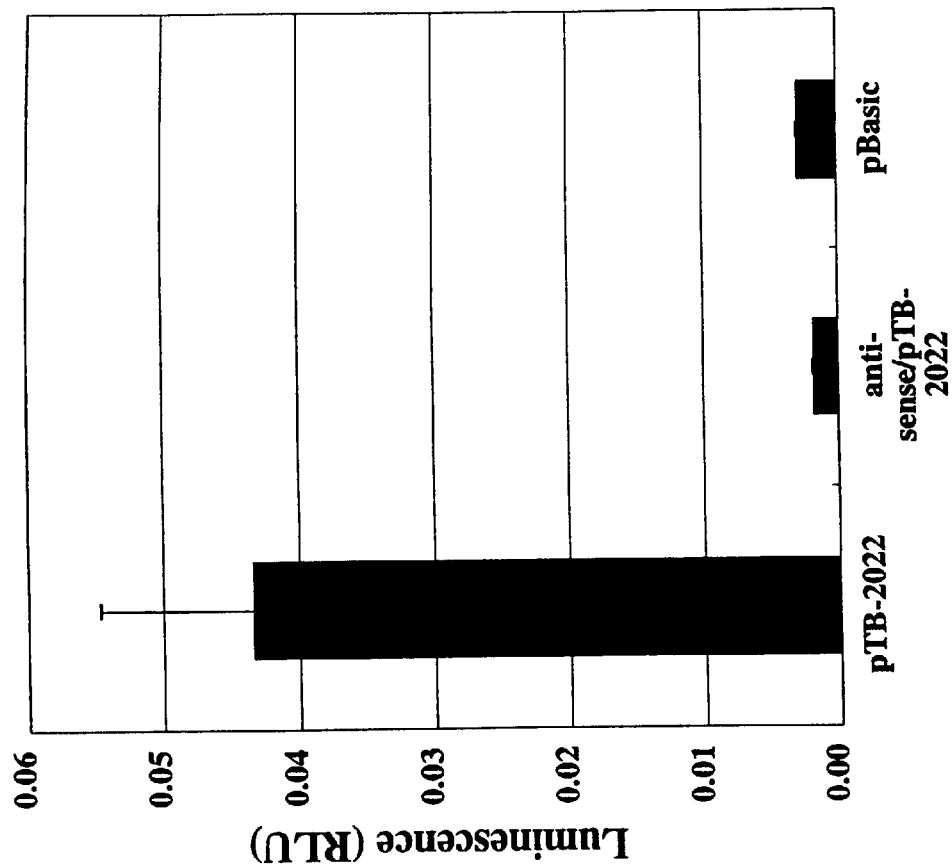
FIG. 9 shows the results of promoter activity assay of the transformant cells having pTB 2022.

The assay of alkaline phosphatase activity was performed (n=3) using Great EscAPeTMSEAP Reporter System 2 (Clontech) in accordance with the manual. Thus, 10 μl of the cell supernatant obtained by 10 minutes' centrifuging at 12000×g was diluted 20-fold with 1×dilution buffer and incubated at 65° C. for 30 minutes. This sample, 60 μl, was put in a 96-well microtiter plate and 60 μl of Assay Buffer and 60 μl of CSPD Chemiluminescent Substrate were added. After 15 minutes of reaction, alkaline phosphatase activity was determined with Luminoscan/RS (LaboSystems). Then, to correct for the error due to transfection efficiency, pGV-C2 (Nippon Gene) was transfected simultaneously with the respective expression plasmids and cultured for 72 hours and the cell extract was gently centrifuged and diluted 10-fold. To 20 μl of the dilution was added 100 μl of Pick-a-Gene Luminescent Substrate (Nippon Gene) and the luciferase activity was assayed with Luminoscan/RS (LaboSystems). Therefore, promoter activity was expressed in terms of alkaline phosphatase activity divided by luciferase activity (Luminescence, RLU). The results are shown in FIG. 9. As can be seen in FIG. 9, whereas the transformant obtained by inserting the plasmid in the reverse direction and the transformant obtained by inserting pSEAP-Basic gene plasmid showed no promoter activity, the transformant obtained using the expression plasmid pTB-2022 showed significant promoter activity. Therefore, the existence of a DNA fragment having functional promoter activity in this genomic DNA fragment was confirmed.

Example 5

Immunization and Crude Purification of Rabbit Polyclonal Antibody

The partial peptide [Peptide-I, H-CEDVRGAPYDWRRAPNENGP-OH (SEQ ID NO:39)] and partial peptide [Peptide-II, H-PVIGPLKIREQQRSAVSTC-NH₂ (SEQ ID NO:40)] of human LCAT-like protein were chemically synthesized and conjugated with KLH in the routine manner. Freund's complete adjuvant (FCA) was then admixed with a solution of 500 μg of each peptide in saline to prepare a homogeneous emulsion. Those emulsions were injected subcutaneously at the back of 2 rabbits (NZW) each. Two weeks later, as a booster immunizing dose, a homogeneous emulsion prepared by admixing Freund's incomplete adjuvant (FIA) with a saline solution of each peptide-KLH conjugate was injected subcutaneously at the back of rabbits.

The antibody titer was determined as follows. Four weeks after the last immunization, blood was drawn from the auricular vein of rabbits, incubated at 37° C. for 30 minutes, allowed to stand at 4° C. for 24 hours, and then centrifuged to harvest an antiserum. The individual antiserum was serially diluted and added in 100 μl aliquots to a polystyrene 96-well microtiter plate coated with saturating levels of the biotinylated form of the peptide I or II immobilized on an avidin coated plate and incubated at 4° C. for 24 hours. The antiserum was then discarded, the wells were washed, and HRP-labeled goat anti-rabbit IgG antibody was added and incubated at 20° C. for 1 hour. After the wells were sufficiently washed, the substrate was added for visualization. The enzymatic reaction was stopped by adding 100 μl of the reaction stop solution and by using a microplate calorimeter, the absorbance at 450 nm was measured.

The antibodies were prepared as follows. The anti-Peptide I antiserum was loaded onto a Peptide-I-Sepharose 6B column and the anti-Peptide-II antiserum onto a Peptide II-Sepharose 6B column, and after the respective columns were washed with PBS buffer (10 mm, pH 7.2) and saline, elution was carried out with glycine HCl buffer (100 mM, pH 2.5). Each eluate was neutralized with 0.1 M sodium hydroxide/H₂O and used as a purified antibody.

Example 6

Figure 10:
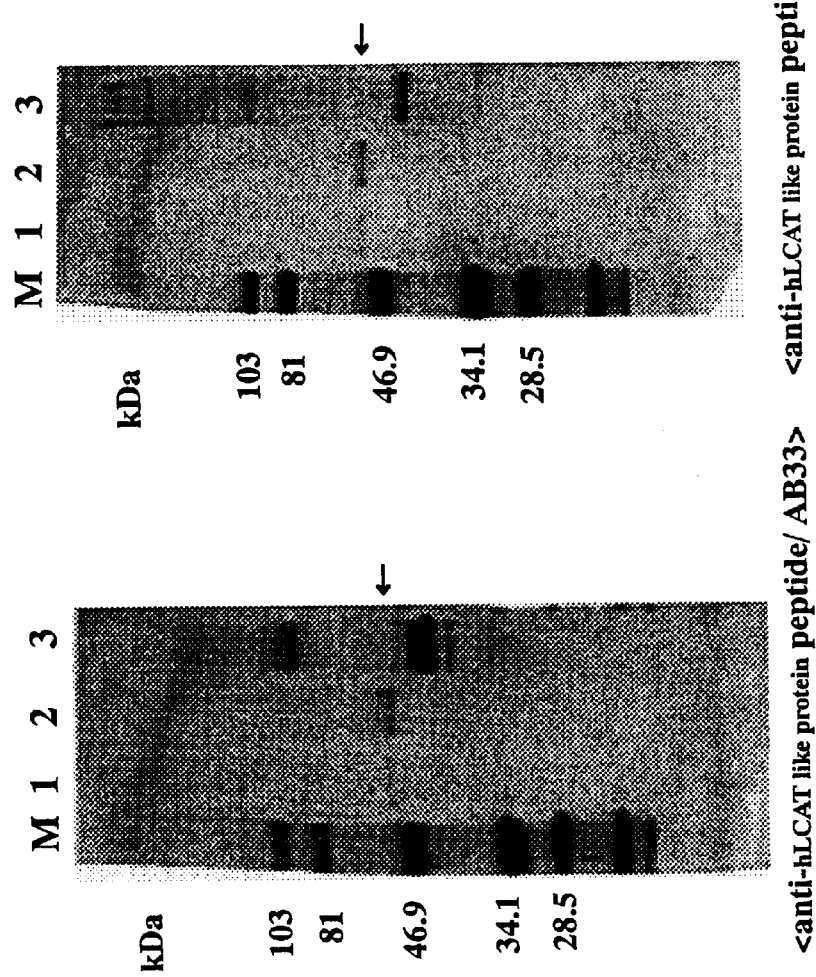
FIG. 10 shows the results of the Western blotting analysis in the Example 6, wherein the lane 1 shows hHDL (12.75 µg), the lane 2 shows hHDL (25.5 µg) and the lane 3 shows Baculoviral hLCAT-like protein.
Figure 11:
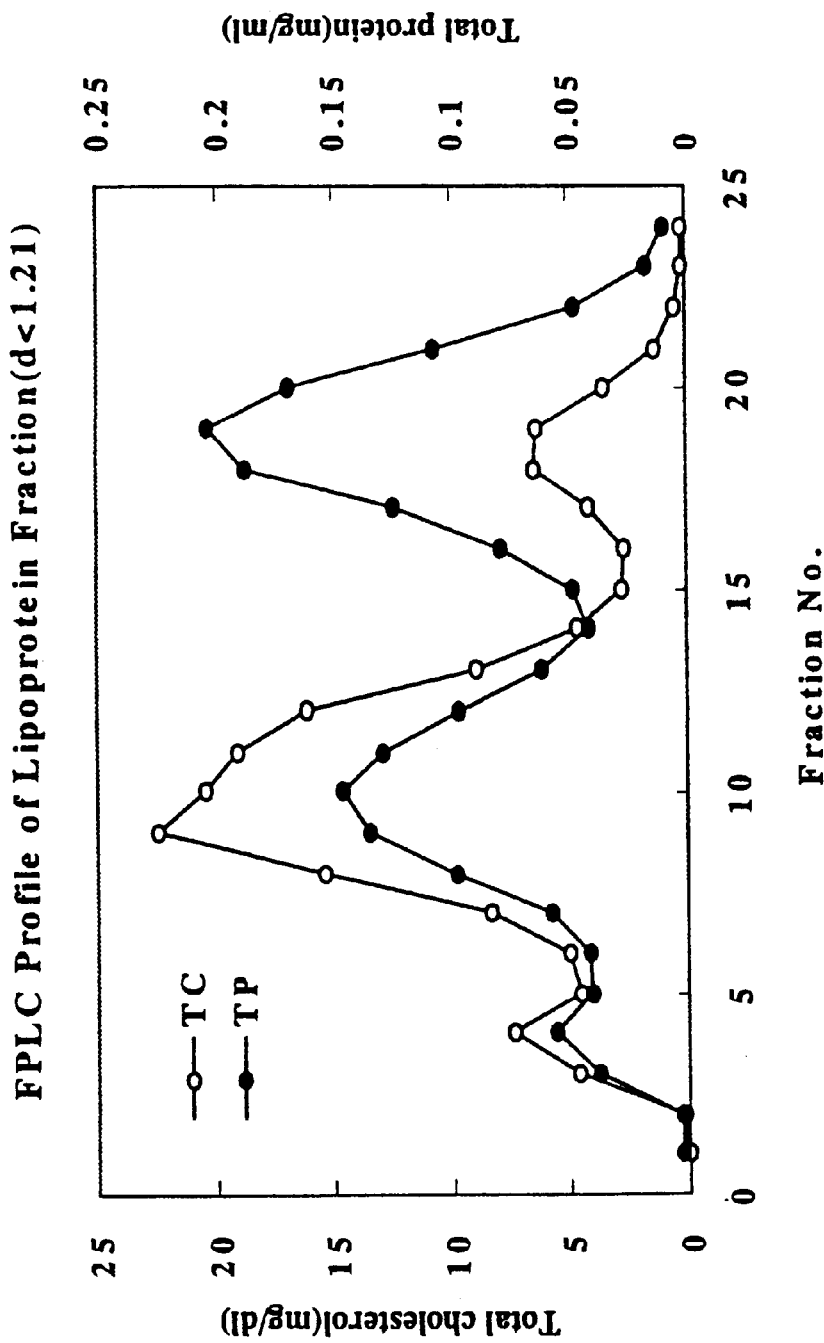
FIG. 11 shows the results of the elution pattern in the Example 6.
Figure 12:
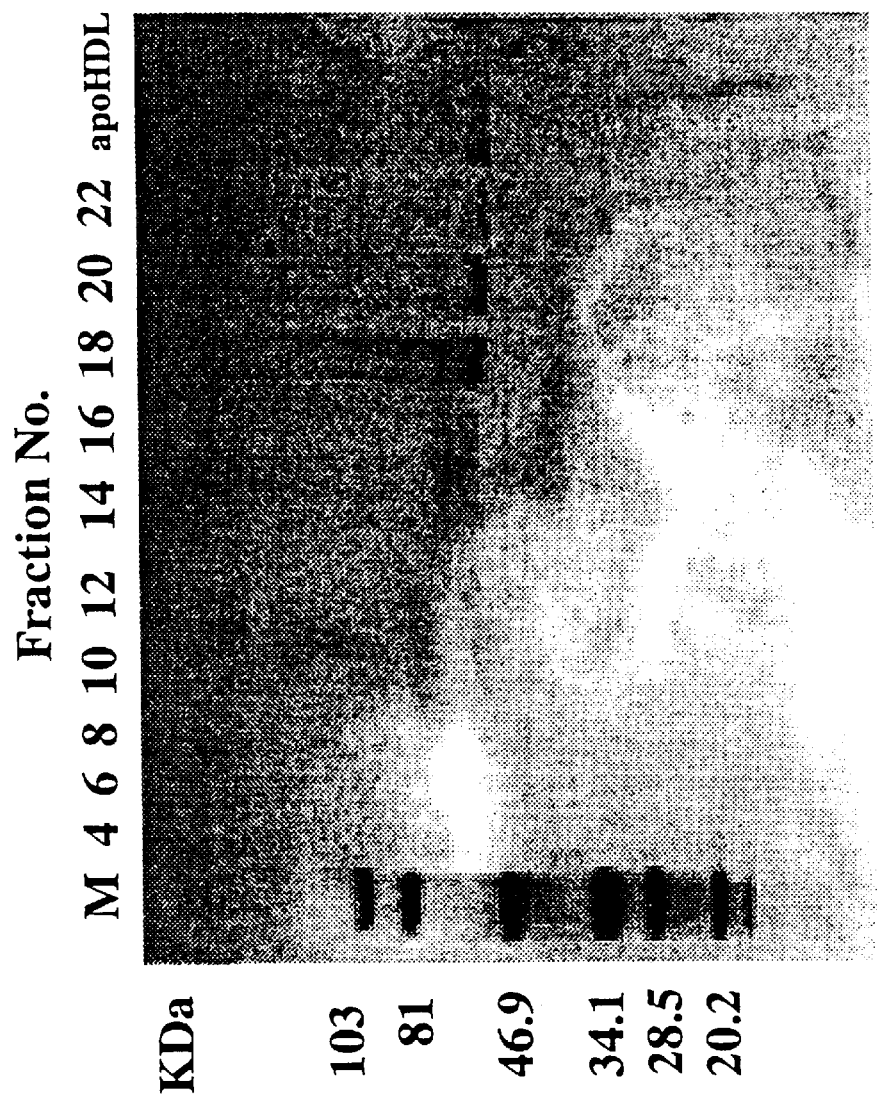
FIG. 12 shows the results of the Western blotting analysis in the Example 6, wherein the lanes 4, 6 show apo VLDL fractions, the lanes 8, 10 and 12 show apo LDL fractions, the lanes 16, 18, 20 and 22 show apo HDL fractions.

Localization of LCAT-like Protein in a Human Apolipoprotein Fraction by Rabbit Polyclonal Anti-LCAT-like Protein-peptide Antibodies By using two kind of IgG antibodies prepared by the procedure described in Example 5, the occurrence of LCAT-like protein in human apolipoprotein fractions was investigated. The P 1.063–1.21 g/ml fraction was isolated following preparative ultracentrifugation of human plasma in KBr solution, and dialyzed against TBS buffer (10 mM Tris-HCl, pH 7.4, 150 mM NaCl), and defatted with ethanol/ether. This sample as apoHDL protein (12.8 mg/ml) was checked by Western blotting analysis with the two kind of IgG antibodies. As a result, there was detected a product with a molecular mass of about 50000 which was recognized by both the antibodies (FIG. 10). For investigating the occurrence in other lipoprotein fractions, human plasma was adjusted for specific gravity with KBr and ultracentrifuged and a fraction less than 1.21 g/ml in density (lipoprotein fraction) was isolated, dialyzed, and purified by FPLC on Superose 6HR (Pharmacia). The elution pattern is presented in FIG. 11. Each fraction was precipitated with TCA, defatted with acetone, and analyzed by Western blotting using anti-Peptide-II antibody. As a result, as shown in FIG. 12, a product with a molecular weight of about 50000 was detected only in the apoHDL protein fraction and not found in other fractions such as apoVLDL and apoLDL protein fractions.

Example 7

Figure 13:
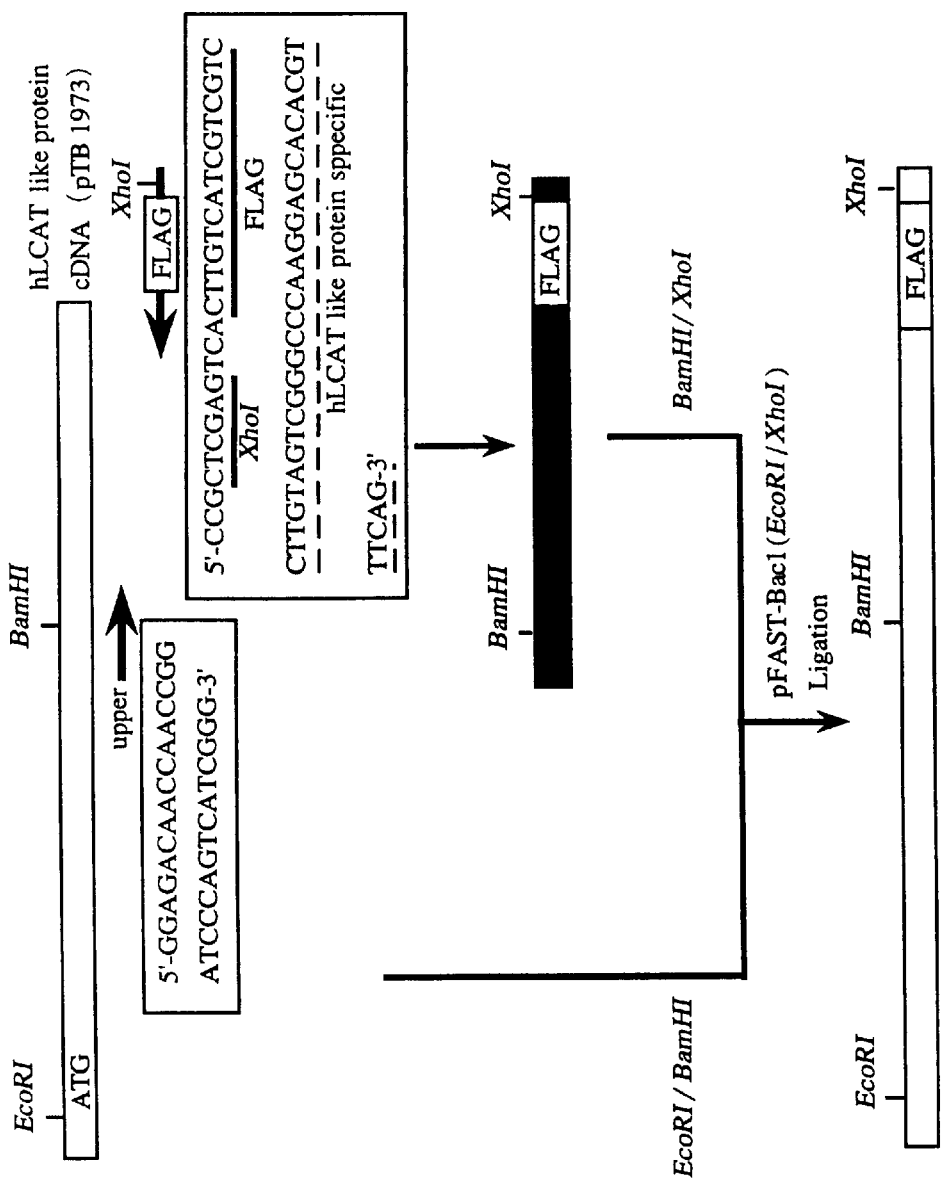
FIG. 13 shows the construction method of the donor plasmid in the Example 7.

Construction of a Recombinant DNA for Expression of Human LCAT-like Protein/FLAG Fusion Gene in Insect Cells To prepare the protein with FLAG peptide fused at C-terminus, a primer [Primer I, 5'-CCGCTCGAGTCACTTGTCATCGTCGTCCTT GTAGTCGGGCCCAAGGAGCACACGTTTCAG-3' (SEQ ID NO:41)] which was complementary to the upper strand and consisting of the sequence encoding FLAG peptide and the Xho I linker sequence added at 5'-end and a primer [Primer II, 5'-GGAGACAACCAACCGGATCCCAGTCATCGGG-3' (SEQ ID NO:42)] for the upper strand upstream of BamHI site were constructed and, as shown in FIG. 13, PCR was carried out using Plasmid pTB1973 as the template to obtain a DNA fragment coding for the C-terminal sequence of said protein and its nucleotide sequence was confirmed. Then, a DNA fragment coding for the N-terminal sequence available on EcoRI-BamHI digestion of pTB1973 was prepared and the two fragments were ligated with pFAST Bac I (Gibco BRL) to provide the objective donor plasmid.

Example 8

Construction of a Recombinant DNA for Expression of Human LCAT-like Protein Gene in Insect Cells A 1.5 kb (approx.) DNA fragment coding for the full length of human LCAT-like protein gene as obtained by digesting plasmid pTB1973 with EcoRI and XbaI was isolated and this fragment was ligated with a similar EcoRI and XbaI digest of pFAST Bac 1 to provide the objective donor plasmid.

Example 9

Expression of the Human LCAT-like Protein/FLAG Fusion Gene in Insect Cells

Using the donor plasmid described in Example 7, a recombinant virus was acquired from the insect cell line Sf9 in accordance with the manual of Bac-To-Bac Baculovirus Expression System (GIBCO BRL). With m.o.i. (number of virus particles per cell) set to 0.1, Sf9 cells were infected with the recombinant virus and cultured for 3 days. The culture supernatant was recovered and analyzed by Western blotting. As a result, a specific band reacting with both the anti-Peptide II antibody obtained in Example 5 and the anti-FLAG M2 monoclonal antibody (mouse, Cosmo Bio) was identified near the molecular size of 47000.

Example 10

Expression of Human LCAT-like Protein Gene in Insect Cells

Using the donor plasmid described in Example 8, a recombinant virus was acquired from the insect cell line Sf9 in accordance with the manual of Bac-To-Bac Baculovirus Expression System (GIBCO BRL). With m.o.i. (number of virus particles per cell) set to 0.1, Sf9 cells were infected with the recombinant virus and cultured for 3 days. The culture supernatant was recovered and analyzed by Western blotting. As a result, a specific band reacting with the anti-Peptide II antibody obtained in Example 5 was identified near the molecular size of 45000.

Example 11

Purification of Human LCAT-like Protein/FLAG Fusion Protein and Determination of the N-terminal Amino Acid Sequence One milliliter of the human LCAT-like protein/FLAG fusion protein-producing recombinant virus obtained in Example 9 was added to the insect cell line High Five ($2.4 \times 10^6$ cells/ml) grown in 50 ml of Excell 400 (JRH) medium. After this infection, the cells were cultured in a spinner culture flask at 27° C. for 3 days. The culture supernatant was recovered (this and subsequent procedures were performed at 4° C.), filtered through a 0.22 $\mu$m filter to remove the cells and the filtrate was dialyzed against TBS buffer (10 mM Tris-HCl, 150 mM NaCl, pH 7.5) overnight and applied onto an anti-FLAG M2 affinity column (0.7×10 cm) (Cosmo Bio). After the column was washed with 30 ml of TBS buffer, elution was carried out with solutions of FLAG peptide in TBS buffer (25–75 $\mu$g/ml) to provide about 170 $\mu$g of the objective protein. A portion of this solution was subjected to SDS-PAGE and stained with CBB. As a result, the protein was detected as a single band near a molecular size of 47000 in agreement with the band detected by Western blotting analysis using anti-FLAG M2 monoclonal antibody. Another portion of the above solution was subjected to SDS-PAGE and transferred onto an PVDF (polyvinylidene difluorile) membrane (MILLIPORE) and the amino acid sequence was determined. Analysis with Peptide Sequencer (HP G1005A) gave SEQ ID NO:43 (AGRHPPVVLV), indicating that the N-terminal sequence of this protein was identical to the sequence available upon cleavage between the 33rd and 34th positions of the precursor protein of SEQ ID NO:6.

Example 12

Crude Purification of Human LCAT-like Protein

One milliliter of the human LCAT-like protein-producing recombinant virus obtained in Example 10 was added to the insect cell line High Five ($2.0 \times 10^5$ cells/ml) cultured in 50 ml of Excell 400 (JRH) medium. After this infection, the cells were cultured in a spinner culture flask at 27° C. for 3 days. The culture supernatant was recovered (this and subsequent procedures were carried out at 4° C.), filtered through a 0.22 $\mu$m filter to remove cells and the filtrate was dialyzed against the buffer (4 mM sodium phosphate, 0.5 M NaCl, pH 7.4) overnight and loaded onto a Phenyl-Sepharose HP column (1.5×10 cm) (Pharmacia) equilibrated with the same buffer. After the column was washed with 100 ml of the same buffer, the objective protein was eluted in 2 ml fractions using about 25 ml of water. The elution patterns detected by UV absorbance and analyzed by Western blotting using anti-Peptide II antibody are shown in FIG. 14. It is clear that the product reacting with the antibody obtained in Example 5 (a molecular size of about 45000) was concentrated in the eluate.

Example 13

Figure 15:
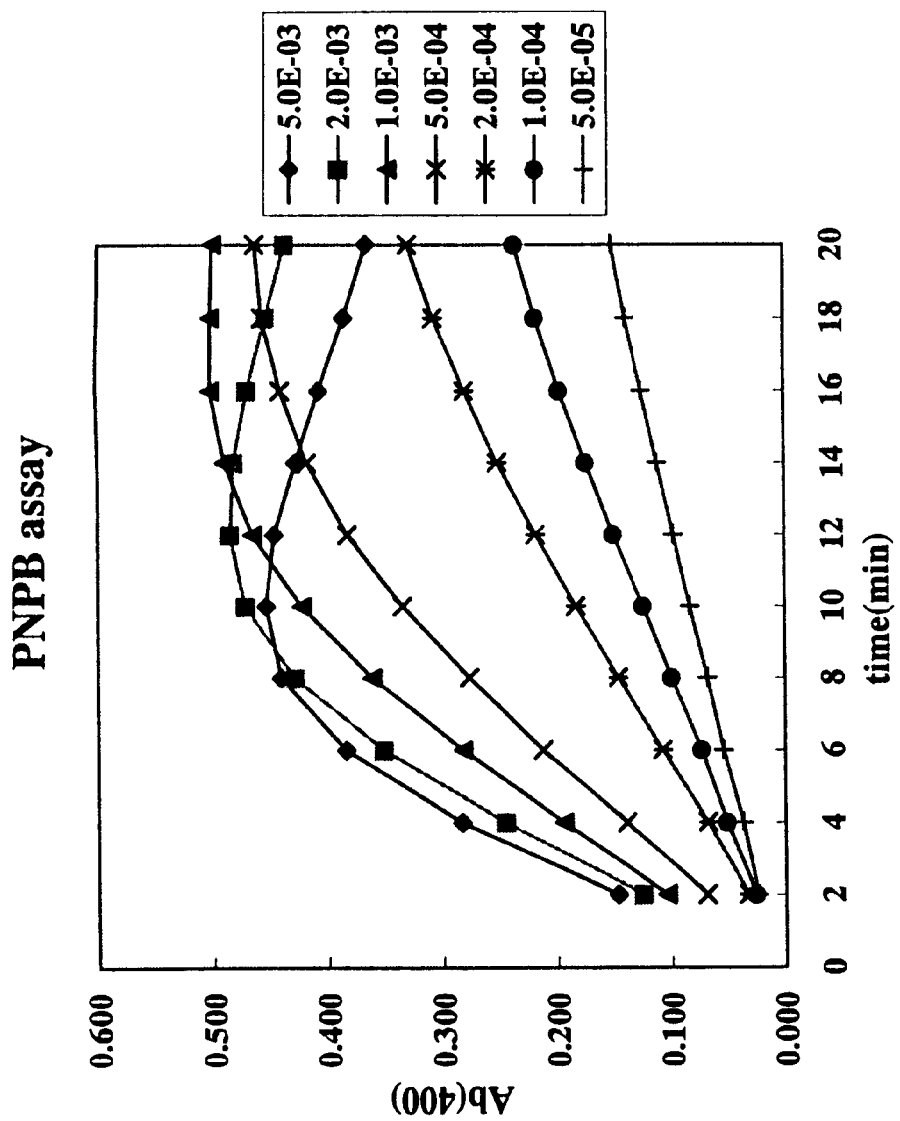
FIG. 15 shows the results of PNPB assay in the Example 13, wherein -♦- shows 5.0E-03, -■- shows 2.0E-03, -Δ- shows 1.0E-03, -x- shows 5.0E-04, -★- shows 2.0E-04, -●- shows 1.0E-04 and + shows 5.0E-05.
Figure 16:
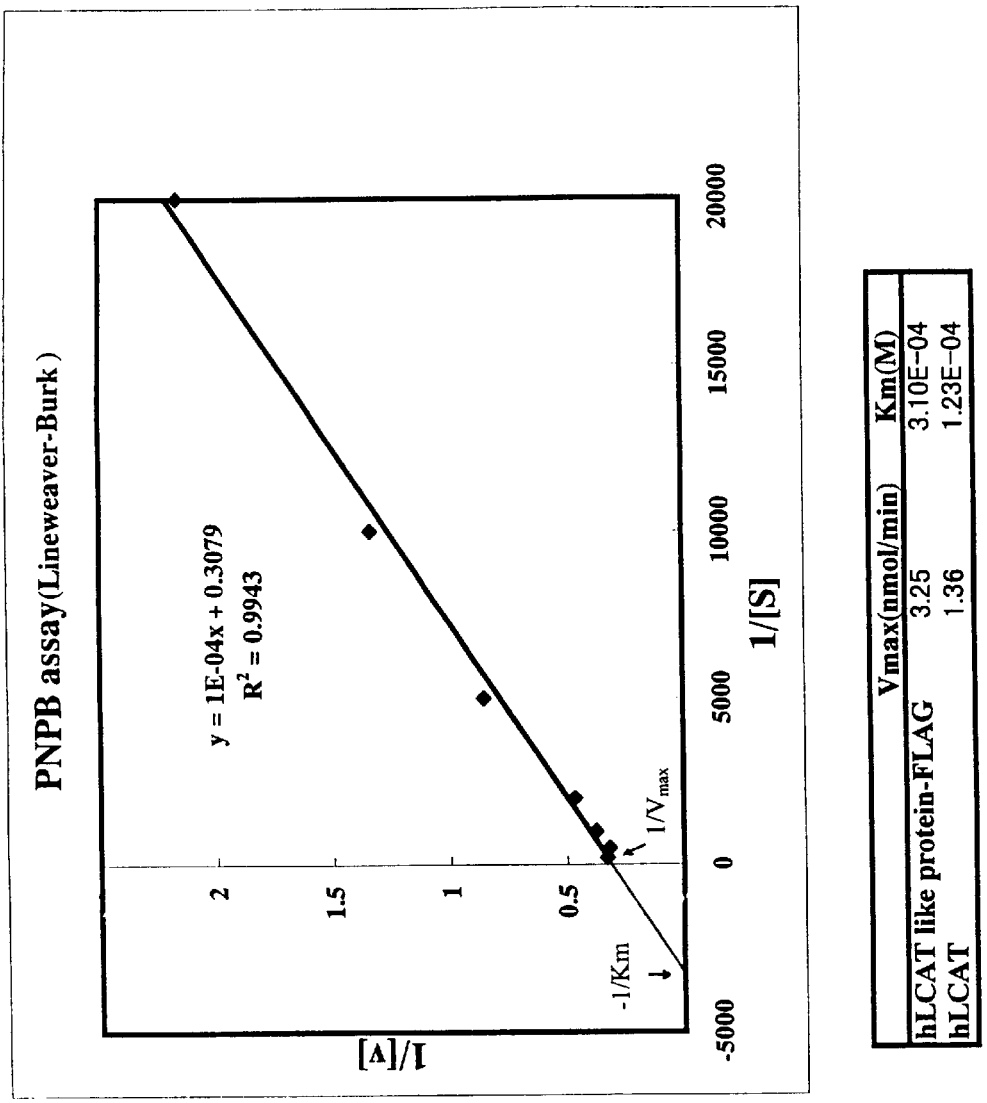
FIG. 16 shows the Vmax (nmol/min) and the Km(M) of the human LCAT like protein/FLAG fusion protein and human LCAT, calculated in accordance with the lineweaver-Burk method in the Example 13.
Figure 17:
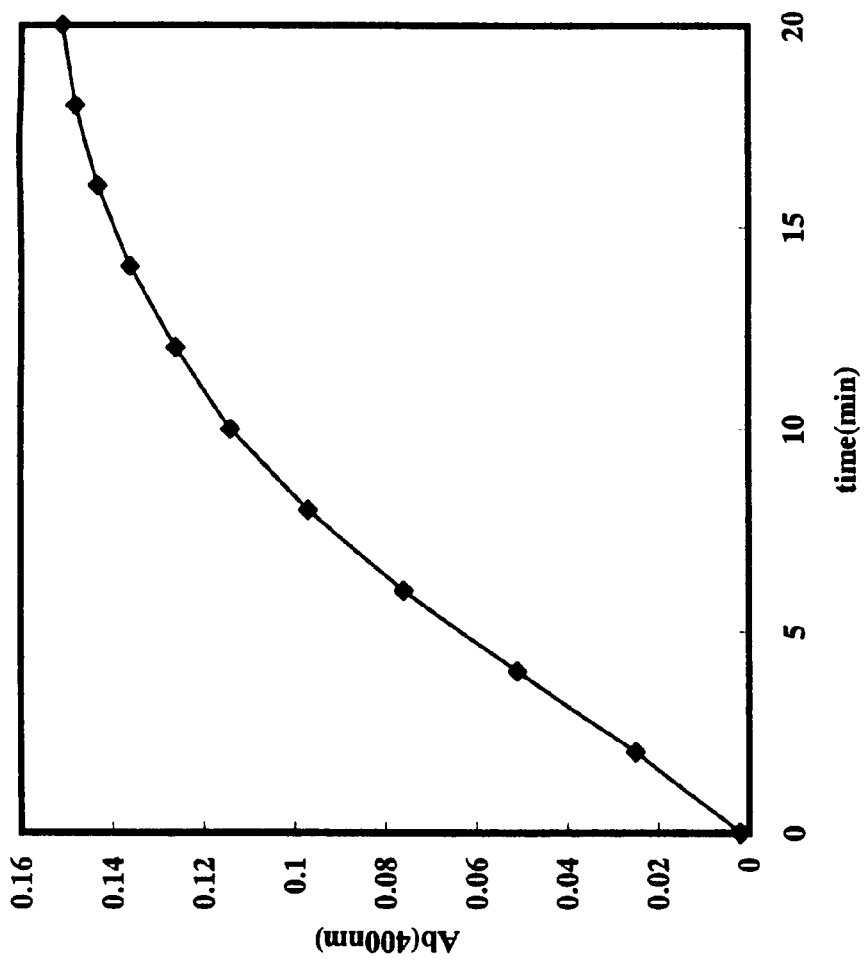
FIG. 17 shows the results of PNPB assay in the Example 13, wherein -♦- shows 1.0E-04.

Assay of the Esterase Activities of Human LCAT-like Protein/FLAG Fusion Protein and Human LCAT-like Protein Using a Fatty Acid Ester Assays were carried out in accordance with the method of Bonelli, F. S. and Jonas, A. [Journal of Biological Chemistry, 264, 14723–14728, 1989]. Thus, to the reaction buffer (10 mM Tris, pH 7.4, 150 mM NaCl, 0.01% EDTA, 1 mM NaN$_3$) was added a graded solution of p-nitrophenyl butyrate (PNPB) in acetonitrile (final concentration: 5 mM–50 gM) as the substrate. Then, the human LCAT-like protein/FLAG fusion protein obtained in Example 9 was added (final concentration: 3.4 $\mu$g/ml) to make 1 ml. The mixture was incubated at 37° C. for 20 minutes and the absorbance at 400 nm was measured at 2-minute intervals. The results are shown in FIG. 15. From the percent changes in absorbance at the respective substrate concentrations, initial velocity was calculated, and according to the Lineweaver-Burk method, Vmax and Km were calculated (FIG. 16). Both the values agreed with the values of human plasma LCAT on an order basis. Using 50 $\mu$l of the semi-purified enzyme solution of fractions 6 and 7 (4 ml) obtained in Example 12 (FIG. 14), a similar activity assay was carried out at a substrate concentration of 100 $\mu$M. As a result, the above enzyme solution was confirmed to have esterase activity (FIG. 17).

Example 14

Figure 18:
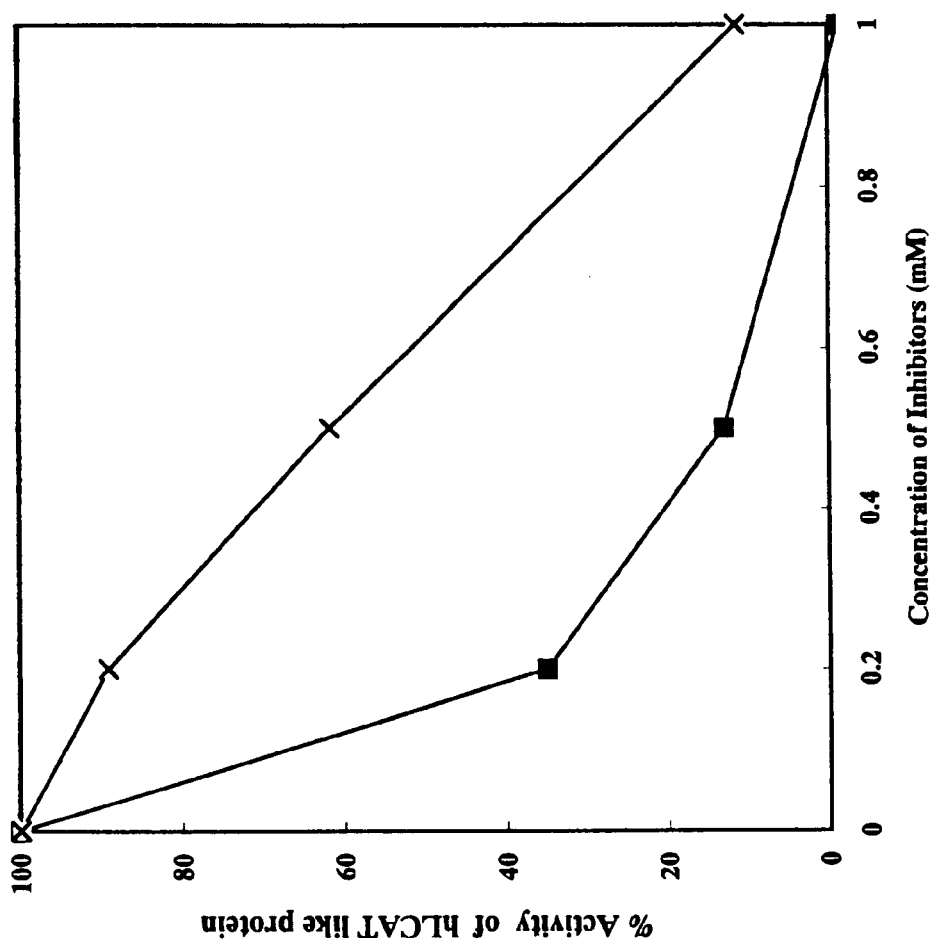
FIG. 18 shows the comparison of the esterase activities between human LCAT like protein after the chemical modification of serine and cysteine residues respectively, in the Example 14, wherein -■- shows DFP treatment, -x- shows DTNB treatment.

Influence of DFP and DTNB on the Esterase Activity of Human LCAT-like Protein/FLAG Fusion Protein as Assayed with PNPB Prior to addition of the substrate in the procedure of Example 13, DFP (diisopropyl fluorophosphate) or DTNB (5,5'-dithiobis(2-nitrobenzoic acid)] was added to the reaction mixture without the substrate and the system was incubated at 25° C. for 1 hour to investigate whether the activity was inhibited or not. The substrate concentration was 500 μM and the final concentration of human LCAT-like protein/FLAG fusion protein was 3.4 μg/ml. As a result, the activity was inhibited by both the inhibitors (FIG. 18), suggesting that both serine and cysteine residues are associated with this esterase activity.

Industrial Applicability

The protein of the present invention, or the DNA coding for the protein of the present invention is useful for an agent for treating or preventing various diseases such as arteriosclerosis, atherosclerosis, hyperlipidemia, hypercalorism, obesity, hypertriglyceridemia, senescence, diseases of brain or renal disorder etc.

The protein of the present invention is also useful as a reagent for the screening for compounds capable of promoting or inhibiting a LCAT-like activity of the protein of the present invention.

Further, the antibody against the protein of the present invention can be used in the assay of the protein in a test sample.

What is claimed is:

1. An isolated protein comprising an amino acid sequence represented by SEQ ID NO:1, a precursor protein thereof or a salt thereof.

2. An isolated protein or precursor protein according to claim 1 which possesses lecithin-cholesterol acyltransferase activity, phospholipase activity, lysophosphatidylcholine to phosphatidylcholine esterification activity, phospholipid-cholesterol acyltransferase activity, lysophospholipase activity, PAF hydrolysis/transesterification activity, fatty acid ester hydrolyzing activity, phospholipid oxide hydrolyzing and cholesterol oxide esterification activity, high-density lipoprotein metabolism regulation activity or lipase activity.

3. An isolated DNA which comprises a DNA having a nucleotide sequence coding for the protein or precursor protein according to claim 1.

4. An isolated DNA according to claim 3, which comprises a nucleotide sequence represented by SEQ ID NO:12.

5. A recombinant vector comprising the DNA according to claim 3.

6. A host cell which is transformed by the recombinant vector according to claim 5.

7. A method for producing the protein or the precursor protein according to claim 1, or the salt thereof, which comprises cultivating a transformed host cell according to claim 6 to produce and accumulate the protein or the precursor protein according to claim 1, and collecting said protein.

8. An isolated antibody which specifically binds to the protein or the precursor protein according to claim 1, or a salt thereof.

9. A method for screening for a compound which promotes or inhibits a lecithin-cholesterol acyltransferase activity, phospholipase activity, lysophosphatidylcholine to phosphatidylcholine esterification activity, phospholipid-cholesterol acyltransferase activity, lysophospholipase activity, PAF hydrolysis/transesterification activity, fatty acid ester hydrolyzing activity, phospholipid oxide hydrolyzing and cholesterol oxide esterification activity, high-density lipoprotein metabolism regulation activity or lipase activity of the protein according to claim 1, or a salt thereof, which comprises measuring and comparing a lecithin-cholesterol acyltransferase activity, in cases that (i) the protein according to claim 1, or a salt thereof is contacted with a lecithin and a non-esterified cholesterol, and (ii) the protein according to claim 1, or a salt thereof is contacted with a lecithin, a non-esterified cholesterol and a test compound.

10. A kit for screening for a compound which promotes or inhibits a lecithin-cholesterol acyltransferase activity, phospholipase activity, lysophosphatidylcholine to phosphatidylcholine esterification activity, phospholipid-cholesterol acyltransferase activity, lysophospholipase activity, PAF hydrolysis/transesterification activity, fatty acid ester hydrolyzing activity, phospholipid oxide hydrolyzing and cholesterol oxide esterification activity, high-density lipoprotein metabolism regulation activity or lipase activity of the protein according to claim 1, or a salt thereof, which comprises the protein according to claim 1, or a salt thereof and instructions for screening the component thereof.

11. A protein or the precursor thereof according to claim 1, which comprises ① an amino acid sequence wherein 1 to 30 contiguous amino acid residues are deleted from either the carboxy terminal or amino terminal end of the amino acid sequence represented by SEQ ID NO:1, ② an amino acid sequence wherein 1 to 30 contiguous amino acid residues are added to either the carboxy terminal or amino terminal end of the amino acid sequence represented by SEQ ID NO:1, ③ an amino acid sequence wherein 1 to 30 contiguous amino acid residues are inserted into the amino acid sequence represented by SEQ ID NO:1, ④ an amino acid sequence wherein 1 to 30 amino acid residues in the amino acid sequence represented by SEQ ID NO:1 are conservatively substituted with 1 to 30 amino acid residues, or ⑥ combinations thereof, and possesses lecithin-cholesterol acyltransferase activity, phospholipase activity, lysophosphatidylcholine to phosphatidylcholine esterification activity, phospholipid-cholesterol acyltransferase activity, lysophospholipase activity, PAF hydrolysis/transesterification activity, fatty acid ester hydrolyzing activity, phospholipid oxide hydrolyzing and cholesterol oxide esterification activity, high-density lipoprotein metabolism regulation activity or lipase activity.

12. An isolated peptide which comprises at least one amino acid sequence selected from the group consisting of amino acid sequences of the 3rd–25th residues, 27th–36th residues, 43rd–66th residues, 68th–86th residues, 92nd–98th residues, 107th–153rd residues, 155th–168th residues, 172nd–180th residues, 189th–240th residues, 256th–262nd residues, 268th–275th residues, 277th–287th residues, 295th–306th residues, 308th–332nd residues, 336th–347th residues and/or 351st–377th residues of the amino acid sequence represented by SEQ ID NO:1.

* * * * *